US009433576B2

(12) United States Patent
Lipp et al.

(10) Patent No.: US 9,433,576 B2
(45) Date of Patent: *Sep. 6, 2016

(54) CATIONIC DRY POWDERS

(75) Inventors: Michael M. Lipp, Framingham, MA (US); Jean C. Sung, Cambridge, MA (US)

(73) Assignee: Pulmatrix, Inc., Lexington, MA (US)

(*) Notice: Subject to any disclaimer, the term of this patent is extended or adjusted under 35 U.S.C. 154(b) by 87 days.

This patent is subject to a terminal disclaimer.

(21) Appl. No.: 13/876,315

(22) PCT Filed: Sep. 29, 2011

(86) PCT No.: PCT/US2011/053833
§ 371 (c)(1),
(2), (4) Date: Jun. 4, 2013

(87) PCT Pub. No.: WO2012/050945
PCT Pub. Date: Apr. 19, 2012

(65) Prior Publication Data
US 2013/0243828 A1 Sep. 19, 2013

Related U.S. Application Data

(63) Continuation-in-part of application No. PCT/US2011/049435, filed on Aug. 26, 2011.

(60) Provisional application No. 61/387,855, filed on Sep. 29, 2010.

(51) Int. Cl.
| *A61K 9/00* | (2006.01) |
| *A61K 9/16* | (2006.01) |
| *A61K 31/198* | (2006.01) |
| *A61K 33/14* | (2006.01) |
| *A61K 33/06* | (2006.01) |

(52) U.S. Cl.
CPC ........... *A61K 9/0075* (2013.01); *A61K 9/1611* (2013.01); *A61K 31/198* (2013.01); *A61K 33/06* (2013.01); *A61K 33/14* (2013.01)

(58) Field of Classification Search
None
See application file for complete search history.

(56) References Cited

U.S. PATENT DOCUMENTS

| 4,233,405 A | 11/1980 | Neubeck |
| 4,637,815 A | 1/1987 | Lemole |
| 4,828,844 A | 5/1989 | Rontgen-Odenthal et al. |
| 5,175,152 A | 12/1992 | Singh |
| 5,230,884 A | 7/1993 | Evans et al. |
| 5,466,680 A | 11/1995 | Rudy |
| 5,571,535 A | 11/1996 | Flowers et al. |
| 5,612,053 A | 3/1997 | Baichwal et al. |
| 5,633,003 A | 5/1997 | Cantor |
| 5,654,007 A | 8/1997 | Johnson et al. |
| 5,709,202 A | 1/1998 | Lloyd et al. |
| 5,785,049 A | 7/1998 | Smith et al. |
| 5,817,028 A | 10/1998 | Anderson |
| 5,855,913 A | 1/1999 | Hanes et al. |
| 5,883,084 A | 3/1999 | Peterson et al. |
| 5,898,037 A | 4/1999 | Marx |
| 5,981,559 A | 11/1999 | Nagaoka et al. |
| 5,985,309 A | 11/1999 | Edwards et al. |
| 6,083,922 A | 7/2000 | Montgomery |
| 6,165,463 A | 12/2000 | Platz et al. |
| RE37,053 E | 2/2001 | Hanes et al. |
| 6,214,536 B1 | 4/2001 | Boucher |
| 6,254,854 B1 | 7/2001 | Edwards et al. |
| 6,447,752 B2 | 9/2002 | Edwards et al. |
| 6,451,352 B1 | 9/2002 | Yvin et al. |
| 6,475,523 B1 | 11/2002 | Staniforth |
| 6,572,849 B2 | 6/2003 | Shahinian, Jr. |
| 6,582,728 B1 | 6/2003 | Platz et al. |
| 6,635,283 B2 | 10/2003 | Edwards et al. |
| 6,732,732 B2 | 5/2004 | Edwards et al. |
| 6,749,835 B1 * | 6/2004 | Lipp .................... A61K 9/0073 424/46 |
| 6,830,764 B2 | 12/2004 | Inui et al. |
| 7,008,644 B2 | 3/2006 | Batycky et al. |
| 7,112,572 B2 | 9/2006 | Deadman et al. |
| 7,182,961 B2 | 2/2007 | Batycky et al. |
| 7,192,919 B2 | 3/2007 | Tzannis et al. |
| 7,306,787 B2 | 12/2007 | Tarara et al. |
| 7,384,649 B2 | 6/2008 | Batycky et al. |
| 7,556,798 B2 | 7/2009 | Edwards et al. |
| 7,575,761 B2 | 8/2009 | Bennett et al. |
| 7,838,532 B2 | 11/2010 | Surber et al. |
| 7,879,358 B2 | 2/2011 | Jackson et al. |

(Continued)

FOREIGN PATENT DOCUMENTS

| CN | 1240349 | 1/2000 |
| CN | 1446877 | 10/2003 |

(Continued)

OTHER PUBLICATIONS

International Search Report dated Feb. 9, 2012 from corresponding PCT Application No. PCT/US2011/053833.
Jagdeep et al., "Cospray-Dried Unfractionated Heparin With L-Leucine as a Dry Powder Inhaler Mucolytic for Cystic Fibrosis Therapy," Journal of Pharmaceutical Sciences, 97:4857-4868 (2008).
Adi, et al., "Agglomerate strength and dispersion of pharmaceutical powders," Journal of Aerosol Science, 42:285-294, 2011.
Adjei and Garren, "Pulmonary delivery of peptide drugs: effect of partical size on bioavailability of leuprolide acetate in healthy male volunteers", J.Pharm. Res., 7:565-569 (1990).
Aldrich Catalog pp. 1502, 1998-1999.
Anderson, et al., "Effect of cystic fibrosis on inhaled aerosol boluses" Am. Rev. Respir. Dis., 140: 1317-1324 (1989).
Bergeron, et al., "Controlling droplet deposition with polymer additives" Nature. 405:772-775 (2000).

(Continued)

*Primary Examiner* — Robert A Wax
*Assistant Examiner* — Caralynne Helm
(74) *Attorney, Agent, or Firm* — McDermott Will & Emery LLP

(57) ABSTRACT

The invention relates to respirable dry particles that contain one or more divalent metal cations, such as calcium, in an amount of less than 3% by weight, and to dry powders that contain the respirable particles. The dry particles can further contain an active agent, or can be used as carrier particles to deliver an active agent.

19 Claims, 4 Drawing Sheets

(56) References Cited

U.S. PATENT DOCUMENTS

| | | | |
|---|---|---|---|
| 8,187,637 B2 | 5/2012 | Edwards et al. | |
| 8,591,866 B2 | 11/2013 | Edwards et al. | |
| 2001/0008632 A1 | 7/2001 | Freund et al. | |
| 2001/0038858 A1 | 11/2001 | Roser et al. | |
| 2002/0034477 A1* | 3/2002 | Edwards et al. | 424/43 |
| 2002/0177562 A1 | 11/2002 | Weickert et al. | |
| 2003/0055034 A1 | 3/2003 | Montgomery | |
| 2003/0129139 A1* | 7/2003 | Batycky et al. | 424/46 |
| 2003/0138403 A1 | 7/2003 | Drustrup | |
| 2003/0186894 A1 | 10/2003 | Kuo et al. | |
| 2003/0232019 A1* | 12/2003 | Basu et al. | 424/46 |
| 2004/0009128 A1 | 1/2004 | Rabinowitz et al. | |
| 2004/0047810 A1 | 3/2004 | Staniforth et al. | |
| 2004/0105821 A1 | 6/2004 | Bernstein et al. | |
| 2005/0004020 A1 | 1/2005 | Yu et al. | |
| 2005/0054682 A1 | 3/2005 | Phillips | |
| 2005/0123509 A1 | 6/2005 | Lehrman et al. | |
| 2005/0211244 A1 | 9/2005 | Nilsson et al. | |
| 2005/0220720 A1 | 10/2005 | Edwards et al. | |
| 2005/0255049 A1 | 11/2005 | Slowey et al. | |
| 2005/0276845 A1 | 12/2005 | Roser et al. | |
| 2005/0281740 A1 | 12/2005 | Gong et al. | |
| 2006/0073173 A1 | 4/2006 | Banach et al. | |
| 2006/0142208 A1 | 6/2006 | Boucher | |
| 2006/0147520 A1 | 7/2006 | Ruegg | |
| 2006/0276483 A1 | 12/2006 | Surber et al. | |
| 2007/0053844 A1 | 3/2007 | Watanabe et al. | |
| 2007/0092535 A1 | 4/2007 | Watts | |
| 2007/0104657 A1 | 5/2007 | Batycky et al. | |
| 2007/0202051 A1 | 8/2007 | Schuschnig | |
| 2007/0270502 A1 | 11/2007 | Edwards et al. | |
| 2007/0275091 A1 | 11/2007 | King et al. | |
| 2007/0292454 A1 | 12/2007 | Bell et al. | |
| 2008/0038207 A1 | 2/2008 | Edwards et al. | |
| 2008/0063722 A1* | 3/2008 | Ward | A61K 9/0075 424/489 |
| 2008/0127972 A1 | 6/2008 | Morton | |
| 2008/0152764 A1 | 6/2008 | Kremer et al. | |
| 2008/0190424 A1 | 8/2008 | Lucking et al. | |
| 2009/0208999 A1 | 8/2009 | Groenendaal et al. | |
| 2009/0232744 A1 | 9/2009 | Keller et al. | |
| 2010/0159007 A1 | 6/2010 | Staniforth | |
| 2010/0285142 A1 | 11/2010 | Staniforth et al. | |
| 2011/0192397 A1 | 8/2011 | Saskar et al. | |
| 2011/0236492 A1 | 9/2011 | Morton | |
| 2012/0070417 A1 | 3/2012 | Batycky | |
| 2012/0107414 A1 | 5/2012 | Lipp | |
| 2013/0004542 A1 | 1/2013 | Martyn | |

FOREIGN PATENT DOCUMENTS

| | | |
|---|---|---|
| CN | 1694689 A | 11/2005 |
| CN | 101237853 | 3/2007 |
| CN | 101106975 | 1/2008 |
| EP | 0367723 | 5/1990 |
| EP | 0652011 | 5/1995 |
| EP | 0681833 | 11/1995 |
| EP | 1466610 | 10/2004 |
| JP | 05123398 | 5/1993 |
| JP | 2004-503482 | 2/2004 |
| JP | 2004-532217 | 10/2004 |
| KR | 1020050056622 | 6/2005 |
| NZ | 328476 | 5/1999 |
| NZ | 305168 | 8/1999 |
| NZ | 530123 | 1/2007 |
| WO | 9206695 | 4/1992 |
| WO | 9612470 | 5/1996 |
| WO | 96/31221 | 10/1996 |
| WO | 9736574 | 10/1997 |
| WO | 9744013 | 11/1997 |
| WO | 98/16205 | 4/1998 |
| WO | 9951096 | 10/1999 |
| WO | 9964014 | 12/1999 |
| WO | 0013677 | 3/2000 |
| WO | 0066206 | 11/2000 |
| WO | 01/13892 | 3/2001 |
| WO | WO01/13892 | 3/2001 |
| WO | WO0113892 | 3/2001 |
| WO | 0185136 | 11/2001 |
| WO | 0185137 | 11/2001 |
| WO | 0195874 | 12/2001 |
| WO | 0209574 | 2/2002 |
| WO | 02083079 | 10/2002 |
| WO | 03035028 | 5/2003 |
| WO | 03103632 | 12/2003 |
| WO | 2004/002551 | 1/2004 |
| WO | WO2004/030659 A1 | 4/2004 |
| WO | 2004096204 | 11/2004 |
| WO | 2005004852 | 1/2005 |
| WO | 2005041921 | 5/2005 |
| WO | 2005041922 | 5/2005 |
| WO | 2005092289 | 10/2005 |
| WO | 2006102438 | 9/2006 |
| WO | WO2007/057714 | 5/2007 |
| WO | 2008025560 | 6/2008 |
| WO | WO 2009037503 A2 * | 3/2009 |
| WO | WO 2009140587 A1 * | 11/2009 |
| WO | 2010111640 | 9/2010 |
| WO | 2010111641 | 9/2010 |
| WO | 2010111644 | 9/2010 |
| WO | WO2010/111650 | 9/2010 |
| WO | WO2010/111680 | 9/2010 |
| WO | 2011048379 | 4/2011 |
| WO | 2012-030645 | 3/2012 |
| WO | 2012030647 | 3/2012 |
| WO | 2012030664 | 3/2012 |
| WO | WO2013/104892 | 7/2013 |

OTHER PUBLICATIONS

Boren, "The development of a molecular model of lung" Arch Intern Med 126(3):491-495 (1970).

Broadhead, et al., The Spray Drying of Pharmaceuticals, Drug Development and Industrial Pharmacy, 18 (11&12):1169-1206, 1992.

Bromberg and Klibanov, "Transport of proteins dissolved in organic solvents across biomimetic membranes", Proc. Natl. Acad. Sci. USA, 92(5):1262-6 (1995).

Bucca, C. and G. Rolla, "Nebulised magnesium in asthma: the right solution for an old remedy?" The Lancet, 361:2095-2096 (2003).

Burg, et al., "Cellular Response to Hyperosmotic Stresses," Am. Physiological Soc., 87:1441-1474 (2007).

Cataldo, et al., "Induced sputum: comparison between isotonic and hypertonic saline solution inhalation in patients with asthma" Chest, 120(6):1815-21 (2001).

Chan, H., "Spray Dried Powders and Powder Blends of Recombinant Human Deoxyribonuclease (rhDNase) for Aerosol Delivery," Pharmaceutical Research, 14(4): 431-437, 1997.

Jaffari, et al., "Rapid characterisation of the inherent dispersibility of respirable powders using dry dispersion laser diffraction," International Journal of Pharmaceutics, 447:124-131, 2013.

Chiou, et al., "A novel production method for inhalable cyclosporine A powders by confined liquid impinging jet precipitation," Journal of Aerosol Science, 39:500-509, 2008.

Choi, et al., "Inhalation delivery of proteins from ethanol suspensions" Proc. Natl. Acad. Sci. 98:11103-11107 (2001).

Clarke, et al., "Resistance to two-phase-gas-liquid flow in airways" J. Appl. Physiol.29(4):464-471 (1970).

Copp, et al., "Hypertonic Shock Inhibits Growth Factor Receptor Signaling, Induces Caspase-3 Activation, and Causes Reversible Fragmentation of the Mitochondrial Network," Am. J. Physiol, 288:C403-C415 (2005).

Costello, B., et al., "Use of the Du Nouy Ring with a Rotational Rheometer to Measure Interfacial Rheology Properties", Annual Transactions of the Nordic Rheology Society. 2006, 14.

Crowder, et al., "2001: An Odyssey in Inhaler Formulation and Design," Pharmaceutical Technology, 99-113, Jul. 2001.

Davis, et al., "Charged Polymers Modulate Retrovirus Transduction via Membrane Charge Neutralization and Virus Aggregation", Biophys J,86:1234-1242 (2004).

(56) References Cited

OTHER PUBLICATIONS

Dawson, et al., "Enhanced viscoelasticity of human cystic fibrotic sputum correlates with increasing microheterogeneity in particle transport", J. of Biol. Chem., 278(50):50393-50401 (2003).
Denn, M.M., "Viscoelasticity", In Process Fluid Mechanics, Prentice-Hall, Englewood Cliffs, New Jersey, pp. 358-373 (1980).
Edwards, et al., "Inhaling to mitigate exhaled bioaerosols," PNAS (2004), vol. 101, pp. 17383-17388.
Edwards, "The macrotransport of aerosol particles in the lung: aerosol deposition phenomena" J. Aerosol Sci., 26:293-317 (1995).
Edwards, et al., "Novel Inhalents for Control and Protection Against Airborne Infections," Respiratory Drug Delivery, 2006, pp. 41-48.
Eng PA, et al., "Short-term efficacy of ultrasonically nebulized hypertonic saline in cystic fibrosis," Pediatr. Pulmonol., 21:77-83 (1996).
"European Search Report from corresponding EP Appl. No. 11177874 dated Nov. 21, 2011".
Evrensel, et al., "Viscous airflow through a rigid tube with compliant lining: A simple model for the air-mucus interaction in pulmonary pathways", J.Biomech. Eng., 115:262-267 (1993).
Feng, et al., "Improved clearability of cystic fibrosis sputum with dextran treatment in vitro," Am. J. Respir. Crit. Care Med., 157(3):710-714 (1998).
Ferguson, et al., "Transmission intensity and impact of control policies on the foot and mouth epidemic in Great Britain", Nature, 414(6861):329 (2001).
Fiegel et al., "Airborne Infectious Disease and the Suppression of Pulmonary Bioaeroso!s," DDT, Jan. 2006, 11 (1/2), pp. 51-57.
French, et al., "The influence of formulation on emission, deaggregation and deposition of dry powders for inhalation", J. Aerosol Sci., 27:769-783 (1996).
Friedmen, et al. "A Randomized, Prospective, Double-Blind Study on the Efficacy of Dead Sea Salt Nasal Irrigations," The Laryngoscope, 2006, pp. 878-882, 116.
Fuge, et al., "The geochemistry of iodine—a review", Environmental Geochemistry and Health, 8(2):31-54 (1986).
Gad-El-Hak, et al., "On the interaction of compliant coatings with boundary layer flows", J. Fluid Mech., 140:257-280 (1984).
Ganderton, "The generation of respirable clouds from coarse powder aggregates", Biopharmaceutical Sciences,3:101-105 (1992).
Geller, et al., "Development of a DPI Tobramycin Formulation using Pulmosphere Technology," J. of Aerosol Medicine and Pulmonary Drug Delivery, 24:175-182, 2011.
Ghoroi, et al., "A novel production method for inhalable cyclosporine A powders by confined liquid impinging jet precipitation," 85:11-24, 2013.
Goldberg, et al., "Mechanism of enhancement of microbial cell hydrophobicity by cationic polymers", J. Bacteriology, 172:5650-5654 (1990).
Gonda, "Aerosols for delivery of therapeutic and diagnostic agents to the respiratory tract", Critical Reviews in Therapeutic Drug Carrier Systems, 6:273-313 (1990).
Guo-Zhong Tao, et al., "Hyposmotic Stress Induces Cell Growth Arrest Via Proteasome Activation and Cyclin/Cyclin-Dependent Kinase Degradation," J. Biological Chemistry, 277(22): 19295-19303 (2002).
Hardy, et al. "Sensitivity of aerosol bolus behavior to methacholine-induced bronchoconstriction", Chest, 114 (2):404-10 (1998).
Hatch, G.E., "Comparative Biochemistry of Airway Lining Fluid," In: Parent, R.A., Ed., Treatise on Pulmonary Toxicology, vol. 1: Comparative Biology of the Normal Lung, CRC Press, Boca Raton, Florida (1992).
Hawley's Condensed Chemical Dictionary, 14th edition John Wiley & Sons, 2001, pp. 161 and 977.
Heyder J., et al., "Deposition of particles in the human respiratory tract in the size range 0.005-15μm" J. Aerosol Sci., 17:811-825 (1986).
Hirschman, et al., "Inhibition of human immunodeficiency virus type 1 replication by nonionic block polymer surfactants" J. Med. Virol. 42(3):249-54 (1994).
Hsu, et al., "Role of Viscoelasticity in Tube Model of Airway Reopening. I. Nonnewtonian Sols.", J. Appl Physiol. 76 (6):2481-2489 (1994).
Im, et al., "In vivo determination of surface tension in the horse trachea and in vitro model studies", Respir. Physiol., 109:81-93 (1997).
Iwasaki, et al., "Exacerbation of influenzavirus pneumonia by intranasal administration of surfactant in a mouse model" Arch. Virol., 144:675-685 (1999).
Kaye, et al., "Simultaneously Manufactured Nano-In-Micro(SIMANIM) Particles for Dry-Powder Modified-Release Delivery of Antibodies," Pharmaceutics, Preformulations and Drug Delivery, 98:11:4055-4068, 2009.
Kilpatrick, et al., "Calcium Chloride and Adrenaline as Bronchial Dilators Compared by Sequential Analysis," British Medical Journal (1954), pp. 1388-1391.
King, "Rheology of cystic fibrosis sputum after in vitro treatment with hypertonic saline alone and in combination with recombinant human deoxyribonuclease I" Am. J. Respir. Crit. Care Med., 156(1):173-7 (1997).
King and Tarsitamo, "The effect of structured and unstructured pre-operative teaching: a replication", Nurs. Res., 31(6):324-9 (1982).
King, et al., "The role of mucus gel viscosity, spinnability, and adhesive properties in clearance by simulated cough", Biorheology, 26:737-745 (1989).
King, M., et al., "Mucomodulator Therapy in Cystic Fibrosis: Balancing Mucus Clearability Against the Spread of Airborne Pathogens," Pediatric Pulmonolgy, 2004, pp. 77-79, Supp. 26.
Kirkness, et al., "Decreased surface tension of upper airway mucosal lining liquid increases upper airway patency in anaesthetised rabbits", J. Physiol., 547(Pt 2):603-11(2003).
Kurashima, et al., "A pilot study of surfactant inhalation for the treatment of asthmatic attack" Arerugi, 40(2):160-3 (1991).
Lipp, et al., "Solving medical problems with chemical engineering", Chemtech, 42-57 (Mar. 1997).
Macosko, C.W., "Linear Viscoelasticity", in Rheology. Principles, Measurements, and Applications, Wiley-VCH, New York, pp. 109-133 (1994).
Mai, X.-M, et al., "Hypertonic saline challenge tests in the diagnosis of bronchial hyperresponsiveness and asthma in children," Pediatric Allergy & Immunology, Oct. 2002, 13(5), pp. 361-267.
Makker, et al., "Relation of hypertonic saline responsiveness of the airways to exercise induced asthma symptom severity and to histamine or methacholine reactivity," Thorax, 1993, 48, pp. 142-147.
Marriott, et al., "Changes in the Gel Properties of Tracheal Mucus Induced by Divalent Cations," Biorheology, 1979, pp. 331-337, vol. 16.
The Merck Index, 12th edition, Merck &Co., Inc., Whitehouse Station, NJ, p. 1089. 1996, pp. 177 & 1614-1615.
Merck Manual Home Edition, "Asthma: Lung and Airway Disorders," accessed at www.merck.com/mmhe/print/sec04/ch044a/html accessed on May 5, 2010, 10 pages.
Merck Manual Home Edition, "Chronic Obstructive Pulmonary Disease," accessed at www.merck.com/mmhe/print/sec04/ch045a/html accessed on Mar. 21, 2010, 7 pages.
Merck Manual Home Edition, "Acute Respiratory Distress Syndrome (ARDS)," accessed on Nov. 17, 2011 at www.merckmanuals.com/home/lung_and_airway_disorders/respiratory_filure_and_acute_respiratory_distress_syndrome/acute_respiratory_distress_syndrome_ards.html#v727948, 3 pages.
The Online Merck Manual Medical Second Home Edition article, entitled, "Influenza"—accessed on Feb. 22, 2010 at www.merck.com/mmhe/print/sec17/ch198/ch198d.html, 6 pages.
Miller, M.J., "Assessing the use of Pharmacokinetic Models in Risk Assessments on Inhaled Toxicants", School of Public Health Sciences, Environmental Health, and Toxicology (1992). 6 parts.
Modler, "Calcium as an Adjuvant for Spray-Drying Acid Whey," Journal of Dairy Science, 61:294-299, 1978.
Morrison, F.A., "Introduction, How Much Do I Need to Learn about Rheology?" In Understanding Rheology, Oxford University Press, New York, pp. 1-11 (2001).

(56) References Cited

OTHER PUBLICATIONS

Mouro, D., et al. "Enhancement of Xcelodose Capsule-Filling Capabilities Using Roller Compaction," Pharmaceutical Technology, Feb. 2006.
Nanaumi, et al., "Properties of mixed monolayers of DPCC and viscoelasticity-giving substances", Colloids & Surfaces B: Bioinformatics, 17:167-174 (2000).
Nannini, L.J., et al., "Magnesium Sulfate as a Vehicle for Nebulized Salbutamol in Acute Asthma", Am. J. Med., 108:193-197 (2000).
Oneda, et al., "The Effect of Formulation Variables on the Dissolution and Physical Properties of Spray-Dried Microspheres Containing Organic Salts," Powder Technology, 130:377-384, 2003.
Papineni and Rosenthal, "The size distribution of droplets in the exhaled breath of healthy human subjects", J. Aerosol Med., 10(2):105-116 (1997).
Patton and Platz, "Pulmonary delivery of peptides and proteins for systemic action", Adv. Drug Del. Rev., 8:179-196 (1992).
Paul, Fundamental Immunology, Raven Press, New York, pp. 699-716, 1984.
Perry's Chemical Engineers' Handbook, 7th ed., 1997, pp. 2-10, 2-11, 2-120, 2-121.
Piret, et al., "Sodium lauryl sulfate, a microbicide effective against enveloped and nonenveloped viruses" Curr. Drug Targets. 3(1):17-30 (2002).
Rabbini, et al., "The Influence of formulation components on the aerosolisation properties of spray dried powders," J. of Controlled Release, 110:130-140, 2005.
Raynal, et al., "Calcium-dependent Protein Interactions in MUC5B Provide Reversible Cross-links in Salivary Mucus," The Journal of Biological Chemistry, Aug. 2003, pp. 28703-28710, vol. 278 (31).
Riedler, J., et al. "Inhaled hypertonic saline increases sputum expectoration in cystic fibrosis," J. Pediatr Child Health, 32:48-50 (1996).
Robinson, M., et al., "Effect of hypertonic saline amiloride, and cough on mucociliary clearance in patients with cystic fibrosis," Am J. Respir. Crit. Care Med., 153:1503-1509 (1996).
Robinson, M., et al., "Effect of increasing doses of hypertonic saline on mucociliary clearance in patients with cystic fibrosis," Thorax, 52:900-903 (1997).
Robinson, M., et al., The effect of inhaled mannitol on bronchial mucus clearance in cystic fibrosis patients: a pilot study, Eur. Respir. J., 14:678-685 (1999).
Rosenblum, E. E. ("fish." Grolier Multimedia Encyclopedia, 2006, Grolier Online, accessed Nov. 21, 2006 (gme.grolier.com/cgi-bin/article?assetid=0106750-0), 1 page.
Rudt and Muller, "In vitro Phagocytosis Assay of Nano- and Microparticles by chemiluminescence. I. Effect of Analytical Parameters, Particle Size and Particle Concentration", J. Controlled Release, 22:263-272 (1992).
Sanders, et al., "Cystic fibrosis sputum: a barrier to the transport of nanospheres", Am J Respir Crit Care Med., 162:1905-1911 (2000).
Sarrell, et al., "Nebulized 3% Hypertonic Saline Solution Treatment in Ambulatory Children with Viral Bronchiolitis Decreases Symptoms," Chest, 2002, 122, pp. 2015-2020.
Schelling G., et al., Biophysical Journal, 66:134-140 (1994).
Schurch, et al., "Surfactant displaces particles toward the epithelium in airways and alveoli", Respir Physiol., 80:17-32 (1990).
Serrano, P., et al., "New Data on Pharmacological Properties and Indications of Magnesium," In New Perspectives in Magnesium Research, Springher-Verglag, London, pp. 127-139 (2007).
Seville, et al., "Spray-Dried Powders for Pulmonary Drug Delivery," Crit. Rev. in Therapeutic Drug Carrier Systems, 24(4), 307-360, 2007.
Shigeta, et al. "Synergistic Anti-Influenza Virua A (H1N1) Activities of PM-523 (Polyoxometalate) and Ribavarin In Vitro and In Vivo," Antimicrobial Agents & Chemotherapy, 1997, 41, pp. 1423-1427.
Suara, et al., "Effect of Zinc Salts on Respiratory Syncytial Virus Replication," Antimicrobial Agents and Chemotherapy, Mar. 2004, pp. 783-790, vol. 48 (3).

Tabata and Ikada, "Macrophage phagocytosis of biodegradable microspheres composed of L-lactic acid/glycolic acid homo- and copolymers", J. Biomed. Mater. Res., 22:837-858 (1988).
Takebayashi, et al., "Role of tachykinins in airway responses to ozone in rats" J Appl Physiol 85:442-450 (1998).
Tansey, "The challenges in the development of metered dose inhalation aerosols using ozone-friendly propellants" Spray Technol. Market. 4:26-29 (1994).
Tibby, et al., "Exogenous surfactant supplementation in infants with respiratory syncytial virus bronciolitis" Am J Respir Crit Care Med., 162(4 Pt 1):1251 (2000).
Timsina, et al., Drug Delivery to the respiratory tract using dry powder inhalers Int. J. Pharm., 101:1-13 (1995).
Tsurumi et al., "Effect of high salt treatment on influenza B viral protein synthesis in MDCK cells," Microbiology and immunology, 1983, 27(6), pp. 519-529 (Full document).
Ulcerative Colitis: Inflammatory bowel Disease (n.d.) retrieved from http://adam.about.com/reports/000069_1.htm.
Vehring, "Pharmaceutical Particle Engineering via Spray Drying" Pharma. Res., vol. 25, No. 5, May 2008.
Vinnikov, et al., "Aerosol Inhalations of Calcium Chloride in Combination Therapy of Pulmonary Tuberculosis," Kazanskii Meditsinskii Zhurnal (1962), vol. 4, pp. 7-9 (translation included).
Visser, "Van der Waals and other cohesive forces affecting powder fluidization", Powder Technology, 58:1-10 (1989).
Vollenbroich, et al., "Mechanism of inactivation of enveloped viruses by the biosurfactin from Bacillus subtilis" Biologicals, 25(3):289-97 (1997).
Wade, C.E., "Hypertonic saline resuscitation in sepsis," Critical Care, Oct. 2002, 6(5), 397-398.
Wark, Rab, McDonald V. Nebulized hypertonic saline for cystic fibrosis (Cochrane Review). In: The Cochrane Library. Oxford, UK: Update Software, 2005.
Watanabe et al., "Why Inhaling Salt Water Changes What We Exhale," Journal of Colloid and Interface Science, 2007, 307, pp. 71-78.
Watanabe, et al., "Immunogenicity and protective efficacy of replication-incompetent influenza virus-like particles" Journal of Virology 76(2):767-773 (2002).
Wikipedia, "Hypertonic" Wikipedia, 2006, accessed Nov. 21, 2006 (en.wikipedia.org/wiki/Hypertonic), 2 pages.
Williams, "Portal to the interior: viral pathogenesis and natural compounds that restore mucosal immunity and modulate inflammation", Alternative Medicine Review, 8(4):395-409 (2003).
Zanen and Lamm, "The optimal particle size for parasymathicolytic aerosols in mild asthmatics", J. Int. J. Pharm., 114:111-115 (1995).
Zasadzinski, et al., "The physics and physiology of lung surfactants", Current Opinion in Colloid & Interface Science, 6:506-513 (2001).
Zayas, et al., "A new paradigm in respiratory hygiene: modulating respiratory secretions to contain cough bioaerosol without affecting mucus clearance," BMC Pulm. Med., 11 (2007). I had marked it pink but no date.
Sung, et al., "iSPERSE™: Formulation and In Vitro Characterization of a Novel Dry Powder Drug Delivery Technology," RDD Europe 2011 Meeting, Abstract, (May 3, 2011).
Sung, et al., "iSPERSE™: Formulation and In Vitro Characterization of a Novel Dry Powder Drug Delivery Technology," RDD Europe 2011 Meeting, Poster, (May 3, 2011).
Arold, et al., "Efficacy of Fluticasone and Salmeterol in a Novel Dry Powder Delivery Platform," ATS 2011 Meeting, Abstract #C22 (May 15, 2011).
Arold, et al., "A Novel Inhaled Dry Powder Delivery Platform; Efficacy of Fluticasone and Salmeterol during Allergic Asthma," ISAM 2011 Meeting, Poster (Apr. 6, 2011).
Arold, et al., "A Novel Inhaled Dry Powder Delivery Platform; Efficacy of Fluticasone and Salmeterol during Allergic Asthma," ISAM 2011 Meeting, Abstract (Apr. 6, 2011).
Sung, "A Novel Platform for DP Inhalation Drugs," 2011 Manufacturing Chemist J article Nov. 7, 2011, accessed online on Jan. 11, 2013.

(56) References Cited

OTHER PUBLICATIONS

Arold, et al., "iSPERSE: A Novel Inhaled Dry Powder Delivery Platform for the Delivery of Large Molecule Drugs to the Lung for Local and Systemic Treatments," ATS 2012 Meeting, Abstract (May 18, 2012).

Sung, et al., "Pulmonary Delivery of Combination Drug Products via a Novel Dry Powder Delivery Technology," US-Japan Drug Delivery Symposium 2011, Abstract (Dec. 16, 2011).

Sung, et al., "Pulmonary Delivery of Combination Drug Products via a Novel Dry Powder Delivery Technology," US-Japan Drug Delivery Symposium 2011, Poster (Dec. 16, 2011).

Manzanedo, et al., "Formulation Characterization of a Novel Levofloxacin Pulmonary Dry Powder Drug Delivery Technology," RDD 2012 Meeting, Abstract (May 13, 2012).

Manzanedo, et al., "Formulation Characterization of a Novel Levofloxacin Pulmonary Dry Powder Drug Delivery Technology," RDD 2012 Meeting, Poster (May 13, 2012).

Lawlor, et al., "Development of iSPERSE™ Based Platform for the Delivery of Macromolecules via Dry Powder Formulations," RDD 2012 Meeting, Abstract (May 13, 2012).

Lawlor, et al., "Development of iSPERSE™ Based Platform for the Delivery of Macromolecules via Dry Powder Forthulations," RDD 2012 Meeting, Poster (May 13, 2012).

Manzanedo, et al., "Novel Respiratory Dry Powder Drug Delivery Technology for High Drug Load LABA/LAMA," AAPS 2012 Meeting, Poster (May 21, 2012).

Sung, "A Next-Generation Inhaled Dry Powder Delivery Platform," Drug Development & Delivery, Jul./Aug. 2012, journal article.

"Sung, "New Formulation Expands Potential for Pulmonary and Systemic Therapies," Pharmaceutical Formulation & Quality (PFQ), Dec. 2011/Jan. 2012, Journal Article, accessed online Jan. 11, 2013."

Lawlor, "A High Load Macromolecule Delivery Platform for Pulmonary Dry Powder Drug Delivery," AAPS 2012 Meeting, Poster (May 21, 2012).

Problemy Tuberkuleza, 58(1):40-41 (1980).

* cited by examiner

Gravimetric ACI8 at 60LPM (n=3). Formulation I

Gravimetric ACI8 at 60LPM (n=3). Formulation II

CATIONIC DRY POWDERS

RELATED APPLICATIONS

This application is the U.S. National Stage of International Application No. PCT/US2011/053833, filed Sep. 29, 2011, published in English, which claims the benefit of U.S. Provisional Application No.61/387,855, filed on Sep. 29, 2010 and PCT/US 11/49435, filed on Aug. 26, 2011, the entire teachings of these applications are incorporated herein by reference.

BACKGROUND OF THE INVENTION

Pulmonary delivery of therapeutic agents can offer several advantages over other modes of delivery. These advantages include rapid onset of drug action, the convenience of patient self-administration, the potential for reduced drug side-effects, ease of delivery, the elimination of needles, and the like. With these advantages, inhalation therapy is capable of providing a drug delivery system that is easy to use in an inpatient or outpatient setting.

Metered dose inhalers (MDIs) are used to deliver therapeutic agents to the respiratory tract. MDIs are generally suitable for administering therapeutic agents that can be formulated as solid respirable dry particles in a volatile liquid under pressure. Opening of a valve releases the suspension at relatively high velocity. The liquid then volatilizes, leaving behind a fast-moving aerosol of dry particles that contain the therapeutic agent. MDIs are reliable for drug delivery to the upper and middle airways but are limited because they typically deliver only low doses per actuation. However, it is the bronchioles and alveoli that are often the site of manifestation of pulmonary diseases such as asthma and respiratory infections.

Liquid aerosol delivery is one of the oldest forms of pulmonary drug delivery. Typically, liquid aerosols are created by an air jet nebulizer, which releases compressed air from a small orifice at high velocity, resulting in low pressure at the exit region due to the Bernoulli effect. See, e.g., U.S. Pat. No. 5,511,726. The low pressure is used to draw the fluid to be aerosolized out of a second tube. This fluid breaks into small droplets as it accelerates in the air stream. Disadvantages of this standard nebulizer design include relatively large primary liquid aerosol droplet size often requiring impaction of the primary droplet onto a baffle to generate secondary splash droplets of respirable sizes, lack of liquid aerosol droplet size uniformity, significant recirculation of the bulk drug solution, and low densities of small respirable liquid aerosol droplets in the inhaled air.

Ultrasonic nebulizers use flat or concave piezoelectric disks submerged below a liquid reservoir to resonate the surface of the liquid reservoir, forming a liquid cone which sheds aerosol particles from its surface (U.S. 2006/0249144 and U.S. Pat. No. 5,551,416). Since no airflow is required in the aerosolization process, high aerosol concentrations can be achieved, however the piezoelectric components are relatively expensive to produce and are inefficient at aerosolizing suspensions, requiring active drug to be dissolved at low concentrations in water or saline solutions. Newer liquid aerosol technologies involve generating smaller and more uniform liquid respirable dry particles by passing the liquid to be aerosolized through micron-sized holes. See, e.g., U.S. Pat. Nos. 6,131,570; 5,724,957; and 6,098,620. Disadvantages of this technique include relatively expensive piezoelectric and fine mesh components as well as fouling of the holes from residual salts and from solid suspensions.

Dry powder inhalation has historically relied on lactose blending to allow for the dosing of particles that are small enough to be inhaled, but aren't dispersible enough on their own. This process is known to be inefficient and to not work for some drugs. For example, the drug loading in the overall dry powder is low due to the presence of the lactose carrier which is typically large and bulky. Several groups have tried to improve on these shortcomings by developing dry powder inhaler (DPI) formulations that are respirable and dispersible and thus do not require lactose blending. Dry powder formulations for inhalation therapy are described in U.S. Pat. No. 5,993,805 to Sutton et al.; U.S. Pat. No. 6,921,6527 to Platz et al.; WO 0000176 to Robinson et al.; WO 9916419 to Tarara et al.; WO 0000215 to Bot et al; U.S. Pat. No. 5,855,913 to Hanes et al.; and U.S. Pat. Nos. 6,136,295 and 5,874,064 to Edwards et al.

Broad clinical application of dry powder inhalation delivery has been limited by difficulties in generating dry powders of appropriate particle size, particle density, and dispersibility, in keeping the dry powder stored in a dry state, and in developing a convenient, hand-held device that effectively disperses the respirable dry particles to be inhaled in air. In addition, the particle size of dry powders for inhalation delivery is inherently limited by the fact that smaller respirable dry particles are harder to disperse in air. Dry powder formulations, while offering advantages over cumbersome liquid dosage forms and propellant-driven formulations, are prone to aggregation and low flowability which considerably diminish dispersibility and the efficiency of dry powder-based inhalation therapies. For example, interparticular Van der Waals interactions and capillary condensation effects are known to contribute to aggregation of dry particles. Hickey, A. et al., "Factors Influencing the Dispersion of Dry Powders as Aerosols", Pharmaceutical Technology, Aug. 1994.

The propensity for particles to aggregate or agglomerate increases as particle size decreases. In order to deaggregate particles of a smaller size, a relatively larger dispersion energy is needed. This can be described as inhaled flowrate dependency since the degree of dispersion of the agglomerated particles is a function of inhaled flowrate. What this means to a clinician and a patient is that the dose the patient receives varies depending on their inspiratory flowrate.

One example of how the art has dealt with the need for a high dispersion energy is to require the patient to inhale on a passive dry powder inhaler (DPI) at a high inspiratory flow rate. In Anderson, et al, (European Respiratory Journal, 1997, Nov; 10(11):2465-73) micronized sodium chloride was delivered to patients to cause broncho-provocation. Patients were required to breathe forcefully on the DPI in order to receive the broncho-provocative dose. Flowrates of greater than or equal to 50 LPM on a standard DPI and greater than 28 LPM on a high-resistance DPI were required, both produce higher dispersion energies.

Requiring a patient to inspire at a high flowrate is not always possible, or predictable, e.g., due to patient's disease state or physical condition. Previously, the problem of delivering active agents to the respiratory tract at a relatively constant dose across various flowrates was addressed i) by adding large carrier particles (e.g., typically with an average particle size in excess of 40 µm), such as lactose, ii) by manufacturing particles that are large and porous (e.g., tap density of less than 0.4 g/cc), or iii) by using active dry powder devices that apply significant force to disperse the powders. The first method is still subject to significant variability at varying inspiratory flowrates. The second method requires large volumes of powder to delivery a relatively large dose of powder. The third method requires an expensive inhaler to be purchased, that may also be subject to technical failure. Lipp et al. in U.S. Pat. No. 7,807,200 discuss the production of dry particles having low tap densities to avoid aggregation, e.g., tap densities of less than about 0.4 g/cc and preferably less than about 0.1 g/cc.

To overcome interparticle adhesive forces, Batycky et al. in U.S. Pat. No. 7,182,961 teach production of so called "aerodynamically light respirable particles," which have a volume median geometric diameter (VMGD) of greater than 5 microns (µm) as measured using a laser diffraction instrument such as HELOS (manufactured by Sympatec, Princeton, N.J.) and a tap density of less than 0.4 g/cc. See Batycky et al., column 7, lines 42-65. Another approach to improve dispersibility of respirable particles of average particle size of less than 10 µm, involves the addition of a water soluble polypeptide or addition of suitable excipients (including amino acid excipients such as leucine) in an amount of 50% to 99.9% by weight of the total composition. Eljamal et al., U.S. Pat. No. 6,582,729, column 4, lines 12-19 and column 5, line 55 to column 6, line 31. However, this approach reduces the amount of active agent that can be delivered using a fixed amount of powder. Therefore, an increased amount of dry powder is required to achieve the intended therapeutic results, for example, multiple inhalations and/or frequent administration may be required. Still other approaches involve the use of devices that apply mechanical forces, such as pressure from compressed gasses, to the small particles to disrupt interparticular adhesion during or just prior to administration. See, e.g., U.S. Pat. Nos. 7,601,336 to Lewis et al., 6,737,044 to Dickinson et al., 6,546,928 to Ashurst et al., or U.S. Pat. Applications 20090208582 to Johnston et al.

A further limitation that is shared by each of the above methods is that the aerosols produced typically include substantial quantities of inert carriers, solvents, emulsifiers, propellants, and other non-drug material. In general, large quantities of non-drug material are required for effective formation of respirable dry particles small enough for alveolar delivery (e.g., less than 5 microns and preferably less than 3 microns). However, these amounts of non-drug material also serve to reduce the purity and amount of active drug substance that can be delivered. Thus, these methods remain substantially incapable of introducing large active drug dosages accurately to a patient for systemic delivery.

Therefore, there remains a need for the formation of small particle size aerosols that are highly dispersible. In addition, methods that produce aerosols comprising greater quantities of drug and lesser quantities of non-drug material are needed. Finally, a method that allows a patient to administer a unit dosage rapidly with one or two, small volume breaths is needed.

SUMMARY OF THE INVENTION

The invention relates to respirable dry particles that contain a divalent metal cation salt, such as calcium ($Ca^{2+}$), in an amount of less than 3% by weight, and to dry powders that contain the respirable particles. The invention also relates to respirable dry powders that comprise dry particles that contain less than 3% by weight divalent metal cation, one or more monovalent cations, and an active agent. The divalent cation is generally present in the dry powders and dry particles in the form of one or more salts, which can independently be crystalline, amorphous or a combination of crystalline and amorphous. The dry powders and dry particles can optionally include additional monovalent salts (e.g., sodium salts), therapeutically active agents or pharmaceutically acceptable excipients. In one aspect, the respirable dry particles may be small and highly dispersible. In another aspect, the respirable dry particles may be large or small, e.g., a geometric diameter (VMGD) between 0.5 microns and 30 microns. Optionally, the MMAD of the particles may be between 0.5 and 10 microns, more preferably between 1 and 5 microns.

In some aspects, the respirable dry powders have a volume median geometric diameter (VMGD) of about 10 microns or less and a dispersibility ratio (ratio of VMGD measured at dispersion pressure of 1 bar to VMGD measured at 4 bar (1/4 bar)) of less than about 2 as measured by laser diffraction (RODOS/HELOS system), and contain a calcium salt that provides divalent metal cation in an amount less than 3% by weight of the dry powder. The respirable dry powders can further comprise a monovalent salt that provides monovalent cation, such as $Na^+$, in an amount of about 6% or more by weight of the powders.

The respirable dry powders can have a Fine Particle Fraction (FPF) of less than 5.6 microns of at least 45% of the total dose, FPF of less than 3.4 microns of at least 30% of the total dose, and/or FPF of less than 5.0 microns of at least 45% of the total dose. Alternatively or in addition, the respirable dry powders can have a mass median aerodynamic diameter (MMAD) of about 5 microns or less. The molecular weight ratio of divalent metal cation to the divalent metal cation salt contained in the respirable dry particle can be greater than about 0.1 and/or greater than about 0.16.

The respirable dry powder compositions can include a pharmaceutically acceptable excipient, such as leucine, maltodextrin or mannitol.

The divalent metal cation salt present in the respirable dry powders can be a beryllium salt, a magnesium salt, a calcium salt, a strontium salt, a barium salt, a radium salt and a ferrous salt. For example, the divalent metal cation salt can be a calcium salt, such as calcium lactate, calcium sulfate, calcium citrate, calcium chloride or any combination thereof. The monovalent salt that is optionally present in the respirable dry particle can be a sodium salt, a lithium salt, a potassium salt or any combination thereof.

In certain aspects, the respirable dry powder contains a divalent metal cation salt and a monovalent salt, and contains an amorphous divalent metal cation phase and a crystalline monovalent salt phase. The glass transition temperature of the amorphous phase can be least about 80° C. These respirable dry particles can optionally contain an excipient, such as leucine, maltodextrin and mannitol, which can be amorphous, crystalline or a mixture of forms. The respirable dry particle can have a heat of solution between about −10 kcal/mol and 10 kcal/mol.

Preferably, the divalent metal cation salt is a calcium, and the monovalent salt is a sodium salt. The calcium salt can be calcium citrate, calcium lactate, calcium sulfate, calcium chloride or any combination thereof, and the sodium salt can be sodium chloride. Alternatively, the calcium salt can be calcium carbonate. In another aspect, the divalent metal cation is a magnesium salt. In this aspect, the presence is a monovalent salt is optional.

In other aspects, the respirable dry powder contains a divalent metal salt that provides a cation in an amount less than 3% by weight of the dry powder, the respirable dry powder has a Hausner Ratio of greater than 1.5 and a dispersibility ratio of 1/4 bar or 0.5/4 bar of 2 or less.

The invention also relates to methods for treating a respiratory disease, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of the respirable dry particles or dry powder. The invention also relates to methods for the treatment or prevention of acute exacerbations of chronic pulmonary diseases, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of the respirable dry particles or dry powder.

The invention also relates to methods for treating, preventing and/or reducing contagion of an infectious disease of the respiratory tract, comprising administering to the respiratory tract of a subject in need thereof an effective amount of the respirable dry particles or dry powder.

The invention also relates to a respirable dry powder or dry particle, as described herein, for use in therapy (e.g., treatment, prophylaxis, or diagnosis). The invention also relates to the use of a respirable dry particle or dry powder, as described herein, for use in treatment, prevention or reducing contagion as described herein, and in the manufacture of a medicament for the treatment, prophylaxis or diagnosis of a respiratory disease and/or infection as described herein.

The invention relates to respirable dry particles that contain one or more divalent metal cations, such as calcium or magnesium, in an amount of less than 3% by weight of respirable dry particle, and to dry powders that contain these respirable particles. The dry particles and the dry powders can further contain one or more pharmaceutically active agent(s), e.g., therapeutic and/or prophylactic agents. For example, the dry particles can contain one or more active agent(s) in a co-formulation. The dry particles and active agent(s) can be co-formulated, e.g., by spray drying, freeze-drying, super critical fluids, etc. In another example, the dry particles are not co-formulated and can be used as carrier particles to deliver one or more active agent(s). The carrier particles may be blended together with the one or more active agent(s) to produce a dry powder. The active agent(s) may be in micronized form. Alternatively or in addition, the dry particles may be co-formulated with an active agent(s) (e.g., comprising a first, second, etc. active agent) and subsequently used as carrier particles for additional active agent(s) (e.g., a second, third, fourth, etc. active agent). The co-formulated dry particles may be blended with the one or more additional active agent(s). The resulting dry powder contains both the co-formulated dry particles and the blended active agent. The one or more additional active agent(s) can be the same active agent(s) that are co-formulated in the dry particle, different active agents, or a combination thereof.

Suitable active agents include, but are not limited to, mucoactive or mucolytic agents, surfactants, antibiotics, antivirals, antihistamines, cough suppressants, bronchodilators, anti-inflammatory agents, steroids, vaccines, adjuvants, expectorants, macromolecules, or therapeutics that are helpful for chronic maintenance of cystic fibrosis (CF). Preferred active agents include, but are not limited to, LABAs (e.g., formoterol, salmeterol), short-acting beta agonists (e.g., albuterol), corticosteroids (e.g., fluticasone), LAMAs (e.g., tiotropium), antibiotics (e.g., levofloxacin, tobramycin), antibodies (e.g., therapeutic antibodies), hormones (e.g., insulin), chemokines (e.g., cytokines), growth factors, and combinations thereof. When the dry powders are intended for treatment of CF, preferred additional active agents are short-acting beta agonists (e.g., albuterol), antibiotics (e.g., levofloxacin), recombinant human deoxyribonuclease I (e.g., dornase alfa, also known as DNase), sodium channel blockers (e.g., amiloride), and combinations thereof.

The respirable dry particles of the invention are small and dispersible, and can be used to administer active agents to the lungs, including the deep lung, for local action in the lung or for absorption through the lung and systemic action. Optionally, the MMAD of the dry powder may be between 0.5 and 10 microns, more preferably between 1 and 5 microns, between 1 and 3 microns or between 3 and 5 microns.

In one aspect, the respirable dry powders and dry particles of the invention may be active agent dense, small and dispersible. For example, the dry particles can contain a high percentage of one or more pharmaceutically active agents. For example, as described herein, the active agent may comprise 5% or more, 10% or more, 20% or more, 30% or more, 40% or more, 50% or more, 60% or more, 70% or more, 80% or more, 90% or more, 95% or more, or 97% or more by weight of the dry particle.

In another aspect, the respirable dry particles are mass dense (e.g., have a tap density or envelope mass density of greater than about 0.4 g/cc, or at least about 0.45 g/cc or greater, about 0.5 g/cc or greater, about 0.55 g/cc or greater, about 0.6 g/cc or greater, about 0.7 g/cc or greater or about 0.8 g/cc or greater), small, and dispersible.

The respirable dry particles are generally small, e.g., they possess a geometric diameter (VMGD) between 0.5 microns and 10 microns, or between 1 micron and 7 microns. Optionally, the MMAD of the dry powder may be between 0.5 and 10 microns, more preferably between 1 and 5 microns. The particles optionally have a tap density or envelope mass density greater than 0.4 g/cc, between 0.45 g/cc and 1.2 g/cc, or between 0.55 g/cc and 1.0 g/cc.

The respirable dry particles may also be large, e.g., they posses a (VMGD) between 10 microns and 30 microns, or between 10 microns and 20 microns. Optionally, the MMAD of the dry powder may be between 0.5 and 10 microns, more preferably between 1 and 5 microns. The particles optionally have a tap density or envelope mass density between 0.01 g/cc and 0.4 g/cc, or between 0.05 g/cc and 0.25 g/cc. They are also generarally dispersible.

Respirable dry powders that contain small particles and that are dispersible in air, and preferably dense (e.g., dense in active agent) are a departure from the conventional wisdom. It is well known that the propensity for particles to aggregate or agglomerate increases as particle size decreases. See, e.g., Hickey, A. et al., "Factors Influencing the Dispersion of Dry Powders as Aerosols", Pharmaceutical Technology, Aug. 1994.

As described herein, the invention provides respirable dry powders that contain respirable particles that are small and dispersible in air without additional energy sources beyond the subject's inhalation. Thus, the respirable dry powders and respirable dry particles can be used therapeutically, without including large amounts of non-active components (e.g., excipients such as lactose carrier particles) in the particles or powders, or by using devices that apply mechanical forces to disrupt aggregated or agglomerated particles during or just prior to administration. Rather, devices, such as a passive dry powder inhaler, may be used to deliver the dry powder or dry particles described herein.

In some embodiments, the respirable dry powders and respirable dry particles do not include any excipient (e.g., leucine) in the particles or powders.

The respirable dry powders and respirable particles of the invention can be dense in active agent(s). Suitable active agents include, but are not limited to, mucoactive or mucolytic agents, surfactants, antibiotics, antivirals, antihistamines, cough suppressants, bronchodilators, anti-inflammatory agents, steroids, vaccines, adjuvants, expectorants, macromolecules, or therapeutics that are helpful for chronic maintenance of cystic fibrosis (CF). Preferred active agents include, but are not limited to, LABAs (e.g., formoterol, salmeterol), short-acting beta agonists (e.g., albuterol), corticosteroids (e.g., fluticasone), LAMAs (e.g., tiotropium), antibiotics (e.g., levofloxacin, tobramycin), antibodies (e.g., therapeutic antibodies), hormones (e.g., insulin), chemokines, cytokines, growth factors, and combinations thereof. When the dry powders are intended for treatment of CF, preferred additional active agents are short-acting beta agonists (e.g., albuterol), antibiotics (e.g., levofloxacin), recombinant human deoxyribonuclease I (e.g., dornase alfa, also known as DNase), sodium channel blockers (e.g., amiloride), and combinations thereof.

Accordingly, for respirable dry powders and respirable particles that are dense in active agent(s), a smaller amount of powder will need to be administered to a subject (e.g., a patient) in order to deliver the desired dose of active agent, in comparison to conventional dry powders, such as powders that contain lactose carrier particles. For example, the desired dose of active agent may be delivered with one or two inhalations from a capsule-type or blister-type inhaler using the active agent dense dry powders or particles described herein, whereas three, four or more inhalations may be necessary to administer to a subject an active agent that is present in conventional large porous particles. Hence, respirable dry particles and dry powders that are small, dispersible and dense (e.g., dense in active agent, and/or mass dense) provide significant advantages over the powders commonly used in the art.

DETAILED DESCRIPTION OF THE INVENTION

Figure 1A:
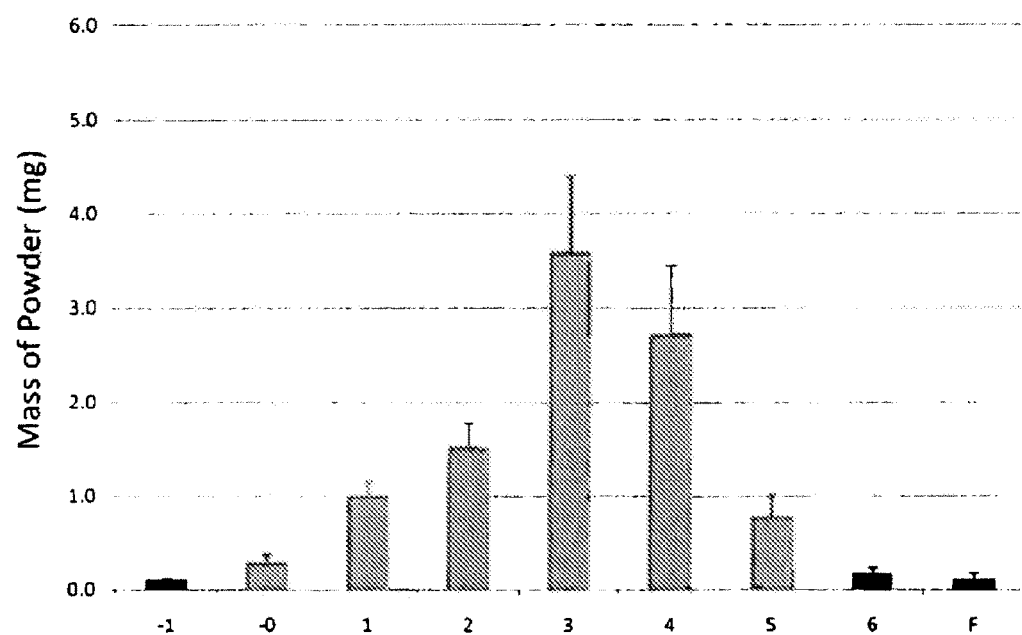
FIGS. 1A-1E are graphs illustrating the aerodynamic particle size distribution of exemplary dry powders of the invention as measured by an eight stage Anderson cascade impactor (ACI). The graphs indicate that all five dry powders were of a respirable size.

The invention relates to respirable dry particles that contain one or more divalent metal cations, such as calcium, in an amount of less than 3% by weight, and to dry powders that contain the respirable particles. The dry particles can further contain an active agent (such as mucoactive or mucolytic agents, surfactants, antibiotics, antivirals, antihistamines, cough suppressants bronchodilators anti-inflammatory agents, steroids, vaccines, adjuvants, expectorants, macromolecules, or therapeutics that are helpful for chronic maintenance of cystic fibrosis (CF)), or can be used as carrier particles to deliver an active agent. The respirable dry particles of the invention are small and dispersible, and can be used to administer active agents to the lungs, including the deep lung, for local action in the lung or for absorbtion through the lung and systemic action.

In one aspect, the respirable dry powders and dry particles of the invention may be active agent dense, small and dispersible. Optionally, the MMAD of the dry powder may be between 0.5 and 10 microns, more preferably between 1 and 5 microns.

Respirable dry powders that contain small particles and that are dispersible in air, and preferably dense (e.g., dense in active agent) are a departure from the conventional wisdom. It is well known that the propensity for particles to aggregate or agglomerate increases as particle size decreases. See, e.g., Hickey, A. et al., "Factors Influencing the Dispersion of Dry Powders as Aerosols", Pharmaceutical Technology, Aug. 1994.

As described herein, the invention provides respirable dry powders that contain respirable particles that are small and dispersible in air without additional energy sources beyond the subject's inhalation. Thus, the respirable dry powders and respirable dry particles can be used therapeutically, without including large amounts of non-active components (e.g., excipients such as lactose carrier particles) in the particles or powders, or by using devices that apply mechanical forces to disrupt aggregated or agglomerated particles during or just prior to administration. In some embodiments, the respirable dry powders and respirable dry particles do not include any excipient (e.g., leucine) in the particles or powders.

The respirable dry powders and respirable particles of the invention can be dense in active agent(s), e.g., mucoactive or mucolytic agents, surfactants, antibiotics, antivirals, antihistamines, cough suppressants, bronchodilators, anti-inflammatory agents, steroids, vaccines, adjuvants, expectorants, macromolecules, or therapeutics that are helpful for chronic maintenance of CF.

For example, as described herein, when an excipient is included in the respirable dry powder or particles, the excipient may comprise about 50% or less by weight, or about 40% or less by weight, or about 30% or less by weight, or about 20% or less by weight, about 12% or less by weight, about 10% or less by weight, about 8% or less by weight). Thus, in one aspect, the respirable particles are not only small and highly dispersible, but can contain a large amount of active ingredient. Accordingly, a smaller amount of powder will need to be administered in order to deliver the desired dose of active agent, in comparison to conventional dry powders, such as powders that contain lactose carrier particles. For example, the desired dose of active agent may be delivered with one or two inhalations from a capsule-type or blister-type inhaler.

DEFINITIONS

The term "dry powder" as used herein refers to a composition that contains finely dispersed respirable dry particles that are capable of being dispersed in an inhalation device and subsequently inhaled by a subject. Such a dry powder may contain up to about 25%, up to about 20%, or up to about 15% water or other solvent, or be substantially free of water or other solvent, or be anhydrous.

The term "dry particles" as used herein refers to respirable particles that may contain up to about 25%, up to about 20%, or up to about 15% water or other solvent, or be substantially free of water or other solvent, or be anhydrous.

The term "respirable" as used herein refers to dry particles or dry powders that are suitable for delivery to the respiratory tract (e.g., pulmonary delivery) in a subject by inhalation. Respirable dry powders or dry particles have a mass median aerodynamic diameter (MMAD) of less than about 10 microns, preferably about 5 microns or less.

The term "small" as used herein to describe respirable dry particles refers to particles that have a volume median geometric diameter (VMGD) of about 10 microns or less, preferably about 5 microns or less.

As used herein, the terms "administration" or "administering" of respirable dry particles refers to introducing respirable dry particles to the respiratory tract of a subject.

As used herein, the term "respiratory tract" includes the upper respiratory tract (e.g., nasal passages, nasal cavity, throat, and pharynx), respiratory airways (e.g., larynx, tranchea, bronchi, and bronchioles) and lungs (e.g., respiratory bronchioles, alveolar ducts, alveolar sacs, and alveoli).

The term "dispersible" is a term of art that describes the characteristic of a dry powder or dry particles to be dispelled into a respirable aerosol. Dispersibility of a dry powder or dry particles is expressed herein as the quotient of the volume median geometric diameter (VMGD) measured at a dispersion (i.e., regulator) pressure of 1 bar divided by the VMGD measured at a dispersion (i.e., regulator) pressure of 4 bar, or VMGD at 0.5 bar divided by the VMGD at 4 bar as measured by HELOS/RODOS laser diffraction system. These quotients are referred to herein as "1 bar/4 bar," and "0.5 bar/4 bar," respectively, and dispersibility correlates with a low quotient. For example, 1 bar/4 bar refers to the VMGD of respirable dry particles or powders emitted from the orifice of a RODOS dry powder disperser (or equivalent technique) at about 1 bar, as measured by a HELOS or other laser diffraction system, divided the VMGD of the same respirable dry particles or powders measured at 4 bar by HELOS/RODOS. Thus, a highly dispersible dry powder or dry particles will have a 1 bar/4 bar or 0.5 bar/4 bar ratio that is close to 1.0. Highly dispersible powders have a low tendency to agglomerate, aggregate or clump together and/or, if agglomerated, aggregated or clumped together, are easily dispersed or de-agglomerated as they emit from an inhaler and are breathed in by the subject. Dispersibility can also be assessed by measuring the size emitted from an inhaler as a function of flowrate. As the flow rate through the inhaler decreases, the amount of energy in the airflow available to be transferred to the powder to disperse it decreases. A highly dispersible powder will have its size distribution as characterized aerodynamically by its mass median aerodynamic diameter (MMAD) or geometrically by its VMGD, not substantially decrease over a range of flow rates typical of inhalation by humans, such as from about 15 to about 60 LPM (L/min or liters per minute).

The terms "FPF (<5.6)," "FPF (<5.6 microns)," and "fine particle fraction of less than 5.6 microns" as used herein, refer to the fraction of a sample of dry particles that have an aerodynamic diameter of less than 5.6 microns. For example, FPF (<5.6) can be determined by dividing the mass of respirable dry particles deposited on the stage one and on the collection filter of a two-stage collapsed Andersen Cascade Impactor (ACI) by the mass of respirable dry particles weighed into a capsule for delivery to the instrument. This parameter may also be identified as "FPF_TD(<5.6)," where TD means total dose. A similar measurement can be conducted using an eight-stage ACI. The eight-stage ACI cutoffs are different at the standard 60 L/min flowrate, but the FPF_TD(<5.6) can be extrapolated from the eight-stage complete data set. The eight-stage ACI result can also be calculated by the USP (United States Pharmacopeia convention) method of using the dose collected in the ACI instead of what was in the capsule to determine FPF.

The terms "FPF (<3.4)," "FPF (<3.4 microns)," and "fine particle fraction of less than 3.4 microns" as used herein, refer to the fraction of a mass of respirable dry particles that have an aerodynamic diameter of less than 3.4 microns. For example, FPF (<3.4) can be determined by dividing the mass of respirable dry particles deposited on the collection filter of a two-stage collapsed ACI by the total mass of respirable dry particles weighed into a capsule for delivery to the instrument. This parameter may also be identified as "FPF_TD(<3.4)," where TD means total dose. A similar measurement can be conducted using an eight-stage ACI. The eight-stage ACI result can also be calculated by the USP method of using the dose collected in the ACI instead of what was in the capsule to determine FPF.

The terms "FPF (<5.0)," "FPF (<5.0 microns)," and "fine particle fraction of less than 5.0 microns" as used herein, refer to the fraction of a mass of respirable dry particles that have an aerodynamic diameter of less than 5.0 microns. For example, FPF (<5.0) can be determined by using an eight-stage ACI at the standard 60 L/min flowrate by extrapolating from the eight-stage complete data set. This parameter may also be identified as "FPF_TD(<5.0)," where TD means total dose. When used in conjunction with a geometric size distribution such as those given by a Malvern Spraytec, Malvern Mastersizer or Sympatec HELOS particle sizer, "FPF (<5.0)" refers to the fraction of a mass of respirable dry particles that have a geometric diameter of less than 5.0 micrometers.

The terms "FPD(<4.4)", "FPD<4.4 μm", "FPD(<4.4 microns)" and "fine particle dose of less than 4.4 microns" as used herein, refer to the mass of respirable dry powder particles that have an aerodynamic diameter of less than 4.4 micrometers. For example, FPD<4.4 μm can be determined by using an eight-stage ACI at the standard 60 L/min flowrate and summing the mass deposited on the filter, and stages 6, 5, 4, 3, and 2 for a single dose of powder actuated into the ACI.

As used herein, the term "emitted dose" or "ED" refers to an indication of the delivery of a drug formulation from a suitable inhaler device after a firing or dispersion event. More specifically, for dry powder formulations, the ED is a measure of the percentage of powder that is drawn out of a unit dose package and that exits the mouthpiece of an inhaler device. The ED is defined as the ratio of the dose delivered by an inhaler device to the nominal dose (i.e., the mass of powder per unit dose placed into a suitable inhaler device prior to firing). The ED is an experimentally-measured parameter, and can be determined using the method of USP Section 601 Aerosols, Metered-Dose Inhalers and Dry Powder Inhalers, Delivered-Dose Uniformity, Sampling the Delivered Dose from Dry Powder Inhalers, United States Pharmacopia convention, Rockville, Md, $13^{th}$ Revision, 222-225, 2007. This method utilizes an in vitro device set up to mimic patient dosing.

The term "capsule emitted powder mass" or "CEPM" as used herein, refers to the amount of dry powder formulation emitted from a capsule or dose unit container during an inhalation maneuver. CEPM is measured gravimetrically, typically by weighing a capsule before and after the inhalation maneuver to determine the mass of powder formulation removed. CEPM can be expressed either as the mass of powder removed, in milligrams, or as a percentage of the initial filled powder mass in the capsule prior to the inhalation maneuver.

The term "effective amount," as used herein, refers to the amount of active agent needed to achieve the desired therapeutic or prophylactic effect, such as an amount that is sufficient to reduce pathogen (e.g., bacteria, virus) uptake or pathogen burden, reduce symptoms (e.g., fever, coughing, sneezing, nasal discharge, diarrhea and the like), reduce occurrence of infection, reduce viral replication, or improve or prevent deterioration of respiratory function (e.g., improve forced expiratory volume in 1 second FEV1 and/or forced expiratory volume in 1 second FEV1 as a proportion of forced vital capacity FEV1/FVC), or produce an effective serum concentration of a pharmaceutically active agent. The actual effective amount for a particular use can vary according to the particular dry powder or dry particle, the mode of administration, and the age, weight, general health of the subject, and severity of the symptoms or condition being treated. Suitable amounts of dry powders and dry particles to be administered, and dosage schedules for a particular patient can be determined by a clinician of ordinary skill based on these and other considerations.

In certain preferred embodiments, the effective amount is sufficient to increase surface and/or bulk viscoelasticy of the respiratory tract mucus (e.g., airway lining fluid), increase gelation of the respiratory tract mucus (e.g., at the surface and/or bulk gelation), increase surface tension of the respiratory tract mucus, increasing elasticity of the respiratory tract mucus (e.g., surface elasticity and/or bulk elasticity), increase surface viscosity of the respiratory tract mucus (e.g., surface viscosity and/or bulk viscosity), reduce the amount of exhaled particles, and/or stimulate innate immunity of airway epithelium.

The term "pharmaceutically acceptable excipient" as used herein means that the excipient can be taken into the lungs with no significant adverse toxicological effects on the lungs. Such excipients are generally regarded as safe (GRAS) by the U.S. Food and Drug Administration.

All references to salts herein include anhydrous forms and all hydrated forms of the salt.

All weight percentages are given on a dry basis.

Dry Powders and Dry Particles

The invention relates to respirable dry powders and dry particles that contain one or more divalent metal cations in an amount of less than 3% by weight of dry particle, and optionally, one or more monovalent metal cation salts.

The respirable dry powder and dry particles of the invention contain a low percentage of divalent metal cation (e.g., calcium, magnesium). The dry particles contain less than 3% divalent metal cation by weight. For example, the dry particles can contain between about 0.1% and 2.9% divalent metal cation by weight.

In a preferred aspect of the invention, the respirable dry powders or respirable dry particles are suitable for administering an active agent to a patient. The dry particles can i) contain one or more active agent(s) in a co-formulation, ii) the dry particles can be used as carrier particles to deliver one or more active agent(s), or iii) the dry particles can be co-formulated with one or more active agent(s) (e.g., first, second, etc. active agent) and used as carrier particles to deliver one or more additional active agent(s) (e.g., second, third, fourth, etc. active agent). Active agents include, but are not limited to, mucoactive or mucolytic agents, surfactants, antibiotics, antivirals, antihistamines, cough suppressants, bronchodilators, anti-inflammatory agents, steroids, vaccines, adjuvants, expectorants, macromolecules, or therapeutics that are helpful for chronic maintenance of cystic fibrosis (CF). Preferred active agents include, but are not limited to, LABAs (e.g., formoterol, salmeterol), short-acting beta agonists (e.g., albuterol), corticosteroids (e.g., fluticasone), LAMAs (e.g., tiotropium), antibiotics (e.g., levofloxacin, tobramycin), antibodies (e.g., therapeutic antibodies), hormones (e.g., insulin), chemokines, cytokines, growth factors, and combinations thereof. When the dry powders are intended for treatment of CF, preferred additional active agents are short-acting beta agonists (e.g., albuterol), antibiotics (e.g., levofloxacin), recombinant human deoxyribonuclease I (e.g., dornase alfa, also known as DNase), sodium channel blockers (e.g., amiloride), and combinations thereof.

The dry particles and active agent(s) can be co-formulated. Co-formulating an active agent into a solution or suspension that contains the divalent cation and, optionally, other components, and then processing the solution or suspension into dry particles e.g., by spray drying, freeze drying, etc., is a preferred aspect of the invention.

Alternatively, the divalent cation salt, optionally with one or more monovalent salt(s) and/or excipients, can be manufactured (e.g., via spray drying) to make dry particles. These dry particles can subsequently be combined with an active agent, e.g., by blending the dry particle with one or more (micronized) therapeutic agents. The dry particles may act as carrier particles in the dry powder when blended together with the (micronized) active agent.

Alternatively or in addition, co-formulated dry particles (containing active agent(s)) can further be blended with additional (micronized) active agents resulting in a dry powder containing co-formulated dry particles (containing active agent(s)) and additional (micronized) active agent(s) in a blend. The co-formulated dry particles may act as carrier particles for the (micronized) active agent in the dry powder.

Chemical Composition

In one aspect, the respirable dry particles of the invention contain one or more divalent metal cation salts (e.g., a calcium salt and/or a magnesium salt), and optionally one or more monovalent metal cation salts (e.g., a sodium salt and/or a potassium salt) and/or an excipient, but do not contain an active agent. These types of respirable dry particles can be blended with a (micronized) active agent to produce a dry powder of the invention. This type of respirable dry particle can be used as carrier particles to deliver an active agent to the respiratory tract (e.g., lungs) for local or systemic delivery.

In another, preferred aspect, the respirable dry particles of the invention contain one or more divalent metal cation salts (e.g., a calcium salt and/or a magnesium salt), and optionally one or more monovalent metal cation salts (e.g., a sodium salt and/or a potassium salt) and/or an excipient, and further contain an active agent in a co-formulation. These types of respirable dry particles can be prepared, for example, by spray drying a feed stock that contains the divalent metal cation salt, the active agent and optionally a monovalent metal cation salt and/or an excipient, as described herein. The co-formulated dry particles can be used to deliver a pharmaceutically active agent to the respiratory tract (e.g., lungs) for local or systemic delivery.

Alternatively or in addition, the co-formulated particle containing a first active agent can then be used as a carrier particle for a second active agent in the dry powder, e.g., when the co-formulated dry particle is blended with the second active agent (e.g., an agent in micronized form). This type of co-formulated respirable dry particle can be used also as a carrier particle to deliver an active agent to the respiratory tract (e.g., lungs) for local or systemic delivery.

It is generally preferred that the one or more divalent metal cations that are present in the dry particle in a total amount of less than 3% by weight of dry particle do not produce a prophylactic or therapeutic effect in the absence of an active agent when the dry particles are administered to a subject. However, without wishing to be bound by any particular theory, it is believed that in some circumstances such dry particles may be administered to a subject in a quantity (dose) sufficient for the one or more divalent metal cations that are present in the dry particle to provide a prophylactic and/or therapeutic effect. It is also believed that the divalent metal cation present in the dry particle may beneficially affect the activity of the active agent, for example, the one or more divalent metal cations may potentiate the prophylactic or therapeutic activity of the active agent.

Preferably, the prophylactic and/or therapeutic effect is a biological activity selected from anti-bacterial activity, anti-viral activity, anti-inflammatory activity, mucociliary clearance, and combinations thereof. Whether a metal cation, on its own, has such a prophylactic and/or therapeutic effect can be evaluated using the in vivo models described herein and those known in the art.

Suitable divalent metal cations include beryllium ($Be^{2+}$), magnesium, ($Mg^{2+}$), calcium ($Ca^{2+}$) strontium ($Sr^{2+}$), barium ($Ba^{2+}$), radium ($Ra^{2+}$), zinc ($Zn^{2+}$) or iron (ferrous ion, $Fe^{2+}$). The divalent metal cation (e.g., calcium) is generally present in the dry powders and dry particles in the form of a salt, which can be crystalline or amorphous. In one aspect, the divalent metal cation can be present in the dry powders and dry particles in the form of a salt, including hydrates or solvates thereof, which can be crystalline or amorphous. The dry powders and dry particles can optionally include additional salts (e.g., monovalent salts, such as sodium salts, potassium salts, and lithium salts.), therapeutically active agents or pharmaceutically acceptable excipients.

In some aspects, the respirable dry powder and dry particles contain one or more salts of a group IIA element (i.e., one or more beryllium salts, magnesium salts, calcium salts, barium salts, radium salts or any combination of the foregoing). In more particular aspects, the respirable dry powder and dry particles contain one or more calcium salts, magnesium salts or any combination of the foregoing. In particular embodiments, the respirable dry powder and dry particles contain one or more calcium salts. In other particular embodiments, respirable dry powder and dry particles contain one or more magnesium salts.

Preferred divalent metal salts (e.g., calcium salts) have one, preferably two or more of the following characteristics: (i) can be processed into a respirable dry particle, (ii) possess sufficient physicochemical stability in dry powder form to facilitate the production of a powder that is dispersible and physically stable over a range of conditions, including upon exposure to elevated humidity, (iii) undergo rapid dissolution upon deposition in the lungs, for example, half of the mass of the cation of the divalent metal can dissolved in less than 30 minutes, less than 15 minutes, less than 5 minutes, less than 2 minutes, less than 1 minute, or less than 30 seconds, and (iv) do not possess properties that can result in poor tolerability or adverse events, such as a significant exothermic or endothermic heat of solution ($\Delta H$), for example, a $\Delta H$ lower than of about −10 kcal/mol or greater than about 10 kcal/mol. Rather, a preferred $\Delta H$ is between about −9 kcal/mol and about 9 kcal/mol, between about −8 kcal/mol and about 8 kcal/mol, between about −7 kcal/mol and about 7 kcal/mol, between about -6 kcal/mol and about 6 kcal/mol,between about -5 kcal/mol and about 5 kcal/mol, between about −4 kcal/mol and about 4 kcal/mol, between about −3 kcal/mol and about 3 kcal/mol, between about −2 kcal/mol and about 2 kcal/mol, between about −1 kcal/mol and about 1 kcal/mol, or about 0 kcal/mol.

Suitable beryllium salts include, for example, beryllium phosphate, beryllium acetate, beryllium tartrate, beryllium citrate, beryllium gluconate, beryllium maleate, beryllium succinate, sodium beryllium malate, beryllium alpha brom camphor sulfonate, beryllium acetylacetonate, beryllium formate or any combination thereof.

Suitable magnesium salts include, for example, magnesium fluoride, magnesium chloride, magnesium bromide, magnesium iodide, magnesium phosphate, magnesium sulfate, magnesium sulfite, magnesium carbonate, magnesium oxide, magnesium nitrate, magnesium borate, magnesium acetate, magnesium citrate, magnesium gluconate, magnesium maleate, magnesium succinate, magnesium malate, magnesium taurate, magnesium orotate, magnesium glycinate, magnesium naphthenate, magnesium acetylacetonate, magnesium formate, magnesium hydroxide, magnesium stearate, magnesium hexafluorsilicate, magnesium salicylate or any combination thereof.

Suitable calcium salts include, for example, calcium chloride, calcium sulfate, calcium lactate, calcium citrate, calcium carbonate, calcium acetate, calcium phosphate, calcium alginate, calcium stearate, calcium sorbate, calcium gluconate and the like.

Suitable strontium salts include, for example, strontium chloride, strontium phosphate, strontium sulfate, strontium carbonate, strontium oxide, strontium nitrate, strontium acetate, strontium tartrate, strontium citrate, strontium gluconate, strontium maleate, strontium succinate, strontium malate, strontium aspartate in either L and/or D-form, strontium fumarate, strontium glutamate in either L- and/or D-form, strontium glutarate, strontium lactate, strontium L-threonate, strontium malonate, strontium ranelate (organic metal chelate), strontium ascorbate, strontium butyrate, strontium clodronate, strontium ibandronate, strontium salicylate, strontium acetyl salicylate or any combination thereof.

Suitable barium salts include, for example, barium hydroxide, barium fluoride, barium chloride, barium bromide, barium iodide, barium sulfate, barium sulfide (S), barium carbonate, barium peroxide, barium oxide, barium nitrate, barium acetate, barium tartrate, barium citrate, barium gluconate, barium maleate, barium succinate, barium malate, barium glutamate, barium oxalate, barium malonate, barium naphthenate, barium acetylacetonate, barium formate, barium benzoate, barium p-t-butylbenzoate, barium adipate, barium pimelate, barium suberate, barium azelate, barium sebacate, barium phthalate, barium isophthalate, barium terephthalate, barium anthranilate, barium mandelate, barium salicylate, barium titanate or any combination thereof.

Suitable radium salts included, for example, radium fluoride, radium chloride, radium bromide, radium iodide, radium oxide, radium nitride or any combination thereof.

Suitable iron (ferrous) salts include, for example, ferrous sulfate, ferrous oxides, ferrous acetate, ferrous citrate, ferrous ammonium citrate, ferrous ferrous gluconate, ferrous oxalate, ferrous fumarate, ferrous maleate, ferrous malate, ferrous lactate, ferrous ascorbate, ferrous erythrobate, ferrous glycerate, ferrous pyruvate or any combination thereof.

As described herein, the respirable dry particles of the invention contain one or more divalent metal cations (e.g., calcium ($Ca^{2+}$) and/or magnesium ($Mg^{2+}$)) which are generally present in the form of a salt in an amount of less than 3% by weight of dry particle. Suitable calcium salts that can be present in the respirable dry particles of the invention include, for example, calcium chloride, calcium sulfate, calcium lactate, calcium citrate, calcium carbonate, calcium acetate, calcium phosphate, calcium alginite, calcium stearate, calcium sorbate, calcium gluconate and the like. In certain aspects, the dry powder or dry particles of the invention do not contain calcium phosphate, calcium carbonate, calcium alginate, calcium sterate or calcium gluconate. In another preferred aspect, the dry powder or dry particles of the invention include calcium citrate, calcium lactate, calcium chloride, calcium sulfate, or any combination of these salts. In another preferred aspect, the dry powder or dry particles include calcium citrate, calcium lactate, or any combination of these salts. In another preferred aspect, the dry powder or dry particles of the invention include calcium lactate, calcium sulfate, calcium carbonate, or any combination of these salts. In another aspect, the dry powder or dry particles of the invention do not contain calcium chloride or calcium phosphate. If desired, the respirable dry particles of the invention contain a divalent metal cation salt (e.g., a calcium salt) and further contain one or more additional salts, such as one or more non-toxic salts of the elements sodium, potassium, magnesium, calcium, aluminum, silicon, scandium, titanium, vanadium, chromium, cobalt, nickel, copper, manganese, zinc, tin, silver and the like. If desired, the dry particles contain at least one calcium salt and at least one monovalent cation salt (e.g., a sodium salt).

Suitable sodium salts that can be present in the respirable dry particles of the invention include, for example, sodium chloride, sodium citrate, sodium sulfate, sodium lactate, sodium acetate, sodium bicarbonate, sodium carbonate, sodium stearate, sodium ascorbate, sodium benzoate, sodium biphosphate, sodium phosphate, sodium bisulfite, sodium borate, sodium gluconate, sodium metasilicate and the like. In a preferred aspect, the dry powders and dry particles include sodium chloride, sodium citrate, sodium lactate, sodium sulfate, or any combination of these salts.

Suitable lithium salts include, for example, lithium chloride, lithium bromide, lithium carbonate, lithium nitrate, lithium sulfate, lithium acetate, lithium lactate, lithium citrate, lithium aspartate, lithium gluconate, lithium malate, lithium ascorbate, lithium orotate, lithium succinate or and combination thereof.

Suitable potassium salts include, for example, potassium chloride, potassium bromide, potassium iodide, potassium bicarbonate, potassium nitrite, potassium persulfate, potassium sulfite, potassium bisulfite, potassium phosphate, potassium acetate, potassium citrate, potassium glutamate, dipotassium guanylate, potassium gluconate, potassium malate, potassium ascorbate, potassium sorbate, potassium succinate, potassium sodium tartrate and any combination thereof.

Some respirable dry particles contain at least one calcium salt selected from the group consisting of calcium lactate, calcium citrate, calcium sulfate, and calcium chloride, and also contain sodium chloride. Other respirable dry particles contain at least one calcium salt selected from the group consisting of calcium lactate, calcium citrate and calcium sulfate, and also contain a sodium salt, e.g., sodium chloride. Further respirable dry particles or dry powders contain calcium carbonate. In certain embodiments, calcium carbonate can be blended with other components into a powder, or can be spray dried as a suspension with other components.

Calcium citrate, calcium sulfate and calcium lactate possess sufficient aqueous solubility to allow for their processing into respirable dry powders via spray-drying and to facilitate their dissolution upon deposition in the lungs, yet possess a low enough hygroscopicity to allow for the production of dry powders with high calcium salt loads that are relatively physically stable upon exposure to normal and elevated humidity. Calcium citrate, calcium sulfate and calcium lactate also have a significantly lower heat of solution than calcium chloride, which is beneficial for administration to the respiratory tract, and citrate, sulfate and lactate ions are safe and acceptable for inclusion in pharmaceutical compositions.

Accordingly, in addition to any combination of the features and properties described herein, the respirable dry particles of the invention can contain a total salt content (e.g., of monovalent and divalent cation salts) of at least about 51% by weight of the respirable dry particles. For example, the respirable dry particles of the invention can include one or more of the salts in a total amount of at least about 55%, at least about 60%, at least about 65%, at least about 70%, at least about 75%, at least about 80%, at least about 85%, at least about 90%, at least about 91%, at least about 92%, or at least about 95% by weight of the respirable dry particles, provided that the divalent metal cation is present at less than 3% by weight of respirable dry particle.

In another embodiment, the respirable dry particles of the invention can contain a total salt content (e.g., of monovalent and/or divalent cation salts) of less than about 51% by weight of the respirable dry particles. For example, the respirable dry particles of the invention can include one or more of the salts in a total amount of less than about 45%, less than about 40%, less than about 35%, less than about 30%, less than about 25%, less than about 20%, less than about 15%, less than about 10%, less than about 9%, less than about 8%, less than about 5%, or less than about 3% by weight of the respirable dry particles, provided that the divalent metal cation is present at less than 3% by weight of respirable dry particle.

Alternatively or in addition, the respirable dry particles of the invention contain a divalent metal cation salt and a monovalent cation salt, where the divalent cation, as a component of one or more salts, is present in an amount of less than 3% by weight of the dry particle, and the weight ratio of divalent cation to monovalent cation is about 50:1 (i.e., about 50 to about 1) to about 0.1:1 (i.e., about 0.1 to about 1). The weight ratio of divalent metal cation to monovalent cation is based on the amount of divalent metal cation and monovalent cation that are contained in the divalent metal cation salt and monovalent salts, respectively, that are contained in the dry particle. In particular examples, the weight ratio of divalent metal cation to monovalent cation is about 0.2:1, about 0.3:1, about 0.4:1, about 0.5:1, about 0.6:1, about 0.7:1, about 0.8:1, about 0.86:1, about 0.92:1, about 1:1; about 1.3:1, about 2:1, about 5:1, about 10:1, about 15:1, about 20:1, about 25:1, about 30:1, about 35:1, about 40:1, about 45:1, or about 50:1, about 20:1 to about 0.1:1, about 15:1 to about 0.1:1, about 10:1 to about 0.1:1, or about 5:1 to about 0.1:1.

Alternatively or in addition, the respirable dry particles of the invention can contain a divalent metal cation salt and a monovalent cation salt, in which the divalent metal cation salt and the monovalent cation salt contain chloride, lactate, citrate or sulfate as the counter ion, and the ratio of divalent metal cation (e.g., $Ca^{2+}$, $Be^{2+}$, $Mg^{2+}$, $Sr^{2+}$, $Ba^{2+}$, $Fe^{2+}$) to monovalent cation (e.g, $Na^+$, $Li^+$, $K^+$) mole:mole is about 50:1 (i.e., about 50 to about 1) to about 0.1:1 (i.e., about 0.1 to about 1), provided that the divalent metal cation is present at less than 3% by weight of respirable dry particle.

The molar ratio of divalent metal cation to monovalent cation is based on the amount of divalent metal cation and monovalent cation that are contained in the divalent metal cation salt and monovalent cation salt, respectively, that are contained in the dry particle. Preferably, divalent metal cation, as a component of one or more divalent metal cation salts, is present in an amount of less than 3% by weight of the respirable dry particle. In particular examples, divalent metal cation and monovalent cation are present in the respirable dry particles in a mole ratio of about 8.0:1, about 7.5:1, about 7.0:1, about 6.5:1, about 6.0:1, about 5.5:1, about 5.0:1, about 4.5:1, about 4.0:1, about 3.5:1, about 3.0:1, about 2.5:1, about 2.0:1, about 1.5:1, about 1.0:1, about 0.77:1, about 0.65:1, about 0.55:1, about 0.45:1, about 0.35:1, about 0.25:1, or about 0.2:1, about 8.0:1 to about 0.55:1, about 7.0:1 to about 0.55:1, about 6.0:1 to about 0.55:1, about 5.0:1 to about 0.55:1, about 4.0:1 to about 0.55:1, about 3.0:1 to about 0.55:1, about 2.0:1 to about 0.55:1, or about 1.0:1 to about 0.55:1. Alternatively, the ratio of divalent metal cation to monovalent cation is about 8.0:1 to about 1:1, about 7.0:1 to about 1:1, about 6.0:1 to about 1:1, about 5.0:1 to about 1:1, about 4.0:1 to about 1:1, about 4.0:1 to about 2.0:1, about 3.9:1 to about 1:1, or about 3.9:1 to about 2.0:1. In a preferred aspect, the ratio of divalent metal cation to monovalent metal cation is from about 8:1 to about 2:1, about 4:1 to about 2:1, or 3.9:1 to about 2:1.

Preferably, the ratio of divalent metal cation (e.g., $Ca^{2+}$, $Be^{2+}$, $Mg^{2+}$, $Sr^{2+}$, $Ba^{2+}$, $Fe^{2+}$) to monovalent cation (e.g, Na+, Li+, K+) mole:mole is about 16.0:1.0 to about 1.0:1.0, about 16.0:1.0 to about 2.0:1.0, about 8.0:1.0 to about 1.0:1.0, about 4.0:1.0 to about 1.0:1.0, about 4:0:1.0 to about 2.0:1.0. More preferably, the divalent metal cation and monovalent cation are present in the respirable dry particles in a mole ratio of about 8.0:1.0 to about 2.0:1.0 or about 4.0:1.0 to about 2.0:1.0. Most preferably, the divalent metal cation is $Ca^{2+}$ and the monovalent cation is $Na^{+}$.

If desired, the respirable dry particles described herein can include a physiologically or pharmaceutically acceptable excipient. For example, a pharmaceutically-acceptable excipient includes any of the standard carbohydrates, sugar alcohols, and amino acids that are known in the art to be useful excipients for inhalation therapy, either alone or in any desired combination. These excipients are generally relatively free-flowing particulates, do not thicken or polymerize upon contact with water, are toxicologically innocuous when inhaled as a dispersed powder and do not significantly interact with the active agent in a manner that adversely affects the desired physiological action.

Other suitable excipients can include, for example, sugars (e.g., lactose, trehalose, maltodextrin), dipalmitoylphosphosphatidylcholine (DPPC), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty, acids, sorbitan trioleate (Span 85), glycocholate, surfactin, poloxomers, sorbitan fatty acid esters, tyloxapol, phospholipids, alkylated sugars, sodium phosphate, maltodextrin, human serum albumin (e.g., recombinant human serum albumin), biodegradable polymers (e.g., PLGA), dextran, dextrin, citric acid, sodium citrate, and the like.

Carbohydrate excipients that are useful in this regard include the mono- and polysaccharides. Representative monosaccharides include carbohydrate excipients such as dextrose (anhydrous and the monohydrate; also referred to as glucose and glucose monohydrate), galactose, mannitol, D-mannose, sorbose and the like. Representative disaccharides include lactose, maltose, sucrose, trehalose and the like. Representative trisaccharides include raffinose and the like. Other carbohydrate excipients include maltodextrin and cyclodextrins, such as 2-hydroxypropyl-beta-cyclodextrin can be used as desired. Representative sugar alcohols include mannitol, sorbitol and the like.

Suitable amino acid excipients include any of the naturally occurring amino acids that form a powder under standard pharmaceutical processing techniques and include the non-polar (hydrophobic) amino acids and polar (uncharged, positively charged and negatively charged) amino acids, such amino acids are of pharmaceutical grade and are generally regarded as safe (GRAS) by the U.S. Food and Drug Administration. Representative examples of non-polar amino acids include alanine, isoleucine, leucine, methionine, phenylalanine, proline, tryptophan and valine. Representative examples of polar, uncharged amino acids include cystine, glycine, glutamine, serine, threonine, and tyrosine. Representative examples of polar, positively charged amino acids include arginine, histidine and lysine. Representative examples of negatively charged amino acids include aspartic acid and glutamic acid. These amino acids are generally available from commercial sources that provide pharmaceutical-grade products such as the Aldrich Chemical Company, Inc., Milwaukee, Wis. or Sigma Chemical Company, St. Louis, Mo.

Preferably, the excipients are chosen from one or more of the following; sugars (e.g., lactose, trehalose), polysaccharide (e.g., dextrin, maltodextrin, dextran, raffinose), sugar alcohols (e.g., mannitol, xylitol, sorbitol), and amino acids (e.g., glycine, alanine, leucine, isoleucine). More preferably, the excipients are chosen from one or more of the following: leucine, mannitol, and maltodextrin. In one aspect of the invention, the excipient is not a phospholipid, e.g., dipalmitoylphosphosphatidylcholine (DPPC), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC). In another aspect of the invention, the excipient is not a carboxylate acid or its salt form, e.g., citric acid or sodium citrate.

Preferred amino acid excipients, such as the hydrophobic amino acid leucine, can be present in the dry particles of the invention in an amount of about 99% or less by weight of respirable dry particles. For example, the respirable dry particles of the invention can contain the amino acid leucine in an amount of about 0.1% to about 10% by weight, 5% to about 30% by weight, about 10% to about 20% by weight, about 5% to about 20% by weight, about 11% to about 50% by weight, about 15% to about 50% by weight, about 20% to about 50% by weight, about 30% to about 50% by weight, about 11% to about 40% by weight, about 11% to about 30% by weight, about 11% to about 20% by weight, about 20% to about 40% by weight, about 51% to about 99% by weight, about 60% to about 99% by weight, about 70% to about 99% by weight, about 80% to about 99% by weight, about 51% to about 90% by weight, about 51% to about 80% by weight, about 51% to about 70% by weight, about 60% to about 90% by weight, about 70% to about 90% by weight, about 45% or less by weight, about 40% or less by weight, about 35% or less by weight, about 30% or less by weight, about 25% or less by weight, about 20% or less by weight, about 18% or less by weight, about 16% or less by weight, about 15% or less by weight, about 14% or less by weight, about 13% or less by weight, about 12% or less by weight, about 11% or less by weight, about 10% or less by weight, about 9% or less by weight, about 8% or less by weight, about 7% or less by weight, about 6% or less by weight, about 5% or less by weight, about 4% or less by weight, about 3% or less by weight, about 2% or less by weight, or about 1% or less by weight.

Preferred carbohydrate excipients, such as maltodextrin and mannitol, can be present in the dry particles of the invention in an amount of about 99% or less by weight of respirable dry particles. For example, the respirable dry particles of the invention can contain maltodextrin in an amount of about 0.1% to about 10% by weight, 5% to about 30% by weight by weight, about 10% to about 20% by weight by weight, about 5% to about 20% by weight, about 11% to about 50% by weight, about 15% to about 50% by weight, about 20% to about 50% by weight, about 30% to about 50% by weight, about 11% to about 40% by weight, about 11% to about 30% by weight, about 11% to about 20% by weight, about 20% to about 40% by weight, about 51% to about 99% by weight, about 60% to about 99% by weight, about 70% to about 99% by weight, about 80% to about 99% by weight, about 51% to about 90% by weight, about 51% to about 80% by weight, about 51% to about 70% by weight, about 60% to about 90% by weight, about 70% to about 90% by weight, about 45% or less by weight, about 40% or less by weight, about 35% or less by weight, about 30% or less by weight, about 25% or less by weight, about 20% or less by weight, about 18% or less by weight, about 16% or less by weight, about 15% or less by weight, about 14% or less by weight, about 13% or less by weight, about 12% or less by weight, about 11% or less by weight, about 10% or less by weight, about 9% or less by weight, about 8% or less by weight, about 7% or less by weight, about 6% or less by weight, about 5% or less by weight, about 4% or less by weight, about 3% or less by weight, about 2% or less by weight, or about 1% or less by weight.

In some preferred aspects, the dry particles contain an excipient selected from leucine, maltodextrin, mannitol and any combination thereof. In particular embodiments, the excipient is leucine, maltodextrin, or mannitol.

If desired, the dry particles or dry powders described herein can include one or more additional active agents, such as mucoactive or mucolytic agents, surfactants, antibiotics, antivirals, antihistamines, cough suppressants, bronchodilators, anti-inflammatory agents, steroids, vaccines, adjuvants, expectorants, macromolecules, or therapeutics that are helpful for chronic maintenance of cystic fibrosis (CF). Preferred active agents include, but are not limited to, LABAs (e.g., formoterol, salmeterol), short-acting beta agonists (e.g., albuterol), corticosteroids (e.g., fluticasone), LAMAs (e.g., tiotropium), antibiotics (e.g., levofloxacin, tobramycin), antibodies (e.g., therapeutic antibodies), hormones (e.g., insulin), cytokines, growth factors, and combinations thereof. When the dry powders are intended for treatment of CF, preferred additional active agents are short-acting beta agonists (e.g., albuterol), antibiotics (e.g., levofloxacin), recombinant human deoxyribonuclease I (e.g., dornase alfa, also known as DNase), sodium channel blockers (e.g., amiloride), and combinations thereof.

In some embodiments, the dry particles or dry powders described herein can contain an agent that disrupts and/or disperses biofilms. Suitable examples of agents to promote disruption and/or dispersion of biofilms include specific amino acid stereoisomers, e.g., D-leucine, D-methionine, D-tyrosine, D-tryptophan, and the like. (Kolodkin-Gal, I., D. Romero, et al. "D-amino acids trigger biofilm disassembly." Science 328(5978): 627-629.) For example, all or a portion of the leucine in the dry powders described herein which contain leucine can be D-leucine.

Examples of suitable mucoactive or mucolytic agents include MUC5AC and MUC5B mucins, DNase, N-acetylcysteine (NAC), cysteine, nacystelyn, dornase alfa, gelsolin, heparin, heparin sulfate, P2Y2 agonists (e.g., UTP, INS365), nedocromil sodium, hypertonic saline, and mannitol.

Suitable surfactants include L-alpha-phosphatidylcholine dipalmitoyl ("DPPC"), diphosphatidyl glycerol (DPPG), 1,2-Dipalmitoyl-sn-glycero-3-phospho-L-serine (DPPS), 1,2-Dipalmitoyl-sn-glycero-3-phosphocholine (DSPC), 1,2-Distearoyl-sn-glycero-3-phosphoethanolamine (DSPE), 1-palmitoyl-2-oleoylphosphatidylcholine (POPC), fatty alcohols, polyoxyethylene-9-lauryl ether, surface active fatty, acids, sorbitan trioleate (Span 85), glycocholate, surfactin, poloxomers, sorbitan fatty acid esters, tyloxapol, phospholipids, and alkylated sugars.

If desired, the dry particles or dry powders described herein can contain an antibiotic. The antibiotic can be suitable for treating any desired bacterial infection. Dry particles or dry powders that contain an antibiotic can be used to reduce the spread of infection, either within a patient or from patient to patient. For example, dry particles or dry powders s for treating bacterial pneumonia or VAT, can further comprise an antibiotic, such as a macrolide (e.g., azithromycin, clarithromycin and erythromycin), a tetracycline (e.g., doxycycline, tigecycline), a fluoroquinolone (e.g., gemifloxacin, levofloxacin, ciprofloxacin and mocifloxacin), a cephalosporin (e.g., ceftriaxone, defotaxime, ceftazidime, cefepime), a penicillin (e.g., amoxicillin, amoxicillin with clavulanate, ampicillin, piperacillin, and ticarcillin) optionally with a β-lactamase inhibitor (e.g., sulbactam, tazobactam and clavulanic acid), such as ampicillin-sulbactam, piperacillin-tazobactam and ticarcillin with clavulanate, an aminoglycoside (e.g., amikacin, arbekacin, gentamicin, kanamycin, neomycin, netilmicin, paromomycin, rhodostreptomycin, streptomycin, tobramycin, and apramycin), a penem or carbapenem (e.g., doripenem, ertapenem, imipenem and meropenem), a monobactam (e.g., aztreonam), an oxazolidinone (e.g., linezolid), vancomycin, glycopeptide antibiotics (e.g., telavancin), tuberculosis-mycobacterium antibiotics and the like.

If desired, the dry particles or dry powders described herein can contain an agent for treating infections with mycobacteria, such as *Mycobacterium tuberculosis*. Suitable agents for treating infections with mycobacteria (e.g., *M. tuberculosis*) include an aminoglycoside (e.g., capreomycin, kanamycin, streptomycin), a fluoroquinolone (e.g., ciprofloxacin, levofloxacin, moxifloxacin), isozianid and isozianid analogs (e.g., ethionamide), aminosalicylate, cycloserine, diarylquinoline, ethambutol, pyrazinamide, protionamide, rifampin, and the like.

If desired, the dry particles or dry powders described herein can contain a suitable antiviral agent, such as oseltamivir, zanamavir, amantidine, rimantadine, ribavirin, gancyclovir, valgancyclovir, foscavir, Cytogam® (Cytomegalovirus Immune Globulin), pleconaril, rupintrivir, palivizumab, motavizumab, cytarabine, docosanol, denotivir, cidofovir, and acyclovir. The dry particles or dry powders can contain a suitable anti-influenza agent, such as zanamivir, oseltamivir, amantadine, or rimantadine.

Suitable antihistamines include clemastine, asalastine, loratadine, fexofenadine and the like.

Suitable cough suppressants include benzonatate, benproperine, clobutinal, diphenhydramine, dextromethorphan, dibunate, fedrilate, glaucine, oxalamine, piperidione, opiods such as codeine and the like.

Suitable brochodilators include short-acting beta2 agonists, long-acting beta2 agonists (LABA), long-acting muscarinic anagonists (LAMA), combinations of LABAs and LAMAs, methylxanthines, short-acting anticholinergic agents (may also be referred to as short acting anti-muscarinic), long-acting bronchodilators and the like.

Suitable short-acting beta$_2$ agonists include albuterol, epinephrine, pirbuterol, levalbuterol, metaproteronol, maxair, and the like.

Examples of albuterol sulfate formulations (also called salbutamol) include Inspiryl (AstraZeneca Plc), Salbutamol SANDOZ (Sanofi-Aventis), Asmasal clickhaler (Vectura Group Plc.), Ventolin® (GlaxoSmithKline Plc), Salbutamol GLAND (GlaxoSmithKline Plc), Airomir® (Teva Pharmaceutical Industries Ltd.), ProAir HFA (Teva Pharmaceutical Industries Ltd.), Salamol (Teva Pharmaceutical Industries Ltd.), Ipramol (Teva Pharmaceutical Industries Ltd), Albuterol sulfate TEVA (Teva Pharmaceutical Industries Ltd), and the like. Examples of epinephrine include Epinephine Mist KING (King Pharmaceuticals, Inc.), and the like. Examples of pirbuterol as pirbuterol acetate include Maxair® (Teva Pharmaceutical Industries Ltd.), and the like. Examples of levalbuterol include Xopenex® (Sepracor), and the like. Examples of metaproteronol formulations as metaproteronol sulfate include Alupent® (Boehringer Ingelheim GmbH), and the like.

Suitable LABAs include salmeterol, formoterol and isomers (e.g., arformoterol), clenbuterol, tulobuterol, vilanterol (Revolair™), indacaterol, carmoterol, isoproterenol, procaterol, bambuterol, milveterol, olodaterol, and the like.

Examples of salmeterol formulations include salmeterol xinafoate as Serevent® (GlaxoSmithKline Plc), salmeterol as Inaspir (Laboratorios Almirall, S.A.), Advair® HFA (GlaxoSmithKline PLC), Advair Diskus® (GlaxoSmithKline PLC, Theravance Inc), Plusvent (Laboratorios Almirall, S.A.), VR315 (Novartis, Vectura Group PLC) and the like. Examples of formoterol and isomers (e.g., arformoterol) include Foster (Chiesi Farmaceutici S.p.A), Atimos (Chiesi Farmaceutici S.p.A, Nycomed Internaional Management), Flutiform® (Abbott Laboratories, SkyePharma PLC), MFF258 (Novartis AG), Formoterol clickhaler (Vectura Group PLC), Formoterol HFA (SkyePharma PLC), Oxis® (Astrazeneca PLC), Oxis pMDI (Astrazeneca), Foradil® Aerolizer (Novartis, Schering-Plough Corp, Merck), Foradil® Certihaler (Novartis, SkyePharma PLC), Symbicort® (AstraZeneca), VR632 (Novartis AG, Sandoz International GmbH), MFF258 (Merck & Co Inc, Novartis AG), Alvesco® Combo (Nycomed International Management GmbH, Sanofi-Aventis, Sepracor Inc), Mometasone furoate (Schering-Plough Corp), and the like. Examples of clenbuterol include Ventipulmin® (Boehringer Ingelheim), and the like. Examples of tulobuterol include Hokunalin Tape (Abbott Japan Co., Ltd., Maruho Co., Ltd.), and the like. Examples of vilanterol include Revolair™ (GlaxoSmithKline PLC), GSK64244 (GlaxoSmithKline PLC), and the like. Examples of indacaterol include QAB 149 (Novartis AG, SkyePharma PLC), QMF149 (Merck & Co Inc) and the like. Examples of carmoterol include CHF4226 (Chiese Farmaceutici S.p.A., Mitsubishi Tanabe Pharma Corporation), CHF5188 (Chiesi Farmaceutici S.p.A), and the like. Examples of isoproterenol sulfate include Aludrin (Boehringer Ingelheim GmbH) and the like. Examples of procaterol include Meptin clickhaler (Vectura Group PLC), and the like. Examples of bambuterol include Bambec (AstraZeneca PLC), and the like. Examples of milveterol include GSK159797C (GlaxoSmithKline PLC), TD3327 (Theravance Inc), and the like. Examples of olodaterol include BI1744CL (Boehringer Ingelheim GmbH) and the like.

Examples of LAMAs include tiotroprium (Spiriva), trospium chloride, glycopyrrolate, aclidinium, ipratropium and the like.

Examples of tiotroprium formulations include Spiriva® (Boehringer-Ingleheim, Pfizer), and the like. Examples of glycopyrrolate include Robinul® (Wyeth-Ayerst), Robinul® Forte (Wyeth-Ayerst), NVA237 (Novartis), and the like. Examples of aclidinium include Eklira® (Forest Labaoratories, Almirall), and the like.

Examples of combinations of LABAs and LAMAs include indacaterol with glycopyrrolate, formoterol with glycopyrrolate, indacaterol with tiotropium, olodaterol and tiotropium, vilanterol with a LAMA, and the like. Examples of combinations of formoterol with glycopyrrolate include PT003 (Pearl Therapeutics) and the like. Examples of combinations of olodaterol with tiotropium include BI1744 with Spirva (Boehringer Ingelheim) and the like. Examples of combinations of vilanterol with a LAMA include GSK573719 with GSK642444 (GlaxoSmithKline PLC), and the like.

Examples of combinations of indacaterol with glycopyrrolate include QVA149A (Novartis), and the like.

Examples of methylxanthine include aminophylline, ephedrine, theophylline, oxtriphylline, and the like.

Examples of aminophylline formulations include Aminophylline BOEHRINGER (Boehringer Ingelheim GmbH) and the like. Examples of ephedrine include Bronkaid® (Bayer AG), Broncholate (Sanofi-Aventis), Primatene® (Wyeth), Tedral SA®, Marax (Pfizer Inc) and the like. Examples of theophylline include Euphyllin (Nycomed International Management GmbH), Theodur (Pfizer Inc, Teva Pharmacetuical Industries Ltd) and the like. Examples of oxtriphylline include Choledyl SA (Pfizer Inc) and the like.

Examples of short-acting anticholinergic agents include ipratropium bromide, and oxitropium bromide.

Examples of ipratropium bromide formulations include Atrovent®/Apovent/Inpratropio (Boehringer Ingelheim GmbH), Ipramol (Teva Pharmaceutical Industries Ltd) and the like. Examples of oxitropium bromide include Oxivent (Boehringer Ingelheim GmbH), and the like.

Suitable anti-inflammatory agents include leukotriene inhibitors, phosphodiesterase 4 (PDE4) inhibitors, other anti-inflammatory agents, and the like.

Suitable leukotriene inhibitors include montelukast formulations (cystinyl leukotriene inhibitors), masilukast, zafirleukast (leukotriene D4 and E4 receptor inhibitors), pranlukast, zileuton (5-lipoxygenase inhibitors), and the like.

Examples of montelukast (cystinyl leukotriene inhibitor) include Singulair® (Merck & Co Inc), Loratadine, montelukast sodium SCHERING (Schering-Plough Corp), MK0476C (Merck & Co Inc), and the like. Examples of masilukast include MCC847 (AstraZeneca PLC), and the like. Examples of zafirlukast (leukotriene D4 and E4 receptor inhibitor) include Accolate® (AstraZeneca PLC), and the like. Examples of pranlukast include Azlaire (Schering-Plough Corp). Examples of zileuton (5-LO) include Zyflo® (Abbott Laboratories), Zyflo CR® (Abbott Laboratories, SkyePharma PLC), Zileuton ABBOTT LABS (Abbott Laboratories), and the like. Suitable PDE4 inhibitors include cilomilast, roflumilast, oglemilast, tofimilast, and the like.

Examples of cilomilast formulations include Ariflo (GlaxoSmithKline PLC), and the like. Examples of roflumilast include Daxas® (Nycomed International Management GmbH, Pfizer Inc), APTA2217 (Mitsubishi Tanabe Pharma Corporation), and the like. Examples of oglemilast include GRC3886 (Forest Laboratories Inc), and the like. Examples of tofimilast include Tofimilast PFIZER INC (Pfizer Inc), and the like.

Other anti-inflammatory agents include omalizumab (anti-IgE immunoglobulin Daiichi Sankyo Company, Limited), Zolair (anti-IgE immunoglobulin, Genentech Inc, Novartis AG, Roche Holding Ltd), Solfa (LTD4 antagonist and phosphodiesterase inhibitor, Takeda Pharmaceutical Company Limited), IL-13 and IL-13 receptor inhibitors (such as AMG-317, MILR1444A, CAT-354, QAX576, IMA-638, Anrukinzumab, IMA-026, MK-6105, DOM-0910, and the like), IL-4 and IL-4 receptor inhibitors (such as Pitrakinra, AER-003, AIR-645, APG-201, DOM-0919, and the like), IL-1 inhibitors such as canakinumab, CRTh2 receptor antagonists such as AZD1981 (CRTh2 receptor antagonist, AstraZeneca), neutrophil elastase inhibitor such as AZD9668 (neutrophil elastase inhibitor, from AstraZeneca), GW856553X Losmapimod (P38 kinase inhibitor, GlaxoSmithKline PLC), Arofylline LAB ALMIRALL (PDE-4 inhibitor, Laboratorios Almirall, S.A.), ABT761 (5-LO inhibitor, Abbott Laboratories), Zyflo® (5-LO inhibitor, Abbott Laboratories), BT061 (anti-CD4 mAb, Boehringer Ingelheim GmbH), Corus (inhaled lidocaine to decrease eosinophils, Gilead Sciences Inc), Prograf® (IL-2-mediated T-cell activation inhibitor, Astellas Pharma), Bimosiamose PFIZER INC (selectin inhibitor, Pfizer Inc), R411 ($\alpha$4 $\beta$1/$\alpha$4 $\beta$7 integrin antagonist, Roche Holdings Ltd), Tilade® (inflammatory mediator inhibitor, Sanofi-Aventis), Orenica® (T-cell co-stimulation inhibitor, Bristol-Myers Squibb Company), Soliris® (anti-CS, Alexion Pharmaceuticals Inc), Entorken® (Farmacija d.o.o.), Excellair® (Syk kinase siRNA, ZaBeCor Pharmaceuticals, Baxter International Inc), KB003 (anti-GMCSF mAb, KaloBios Pharmaceuticals), Cromolyn sodiums (inhibit release of mast cell mediators): Cromolyn sodium BOEHRINGER (Boehringer Ingelheim GmbH), Cromolyn sodium TEVA (Teva Pharmaceutical Industries Ltd), Intal (Sanofi-Aventis), BI1744CL (oldaterol ($\beta$2-adrenoceptor antagonist) and tiotropium, Boehringer Ingelheim GmbH), NF$\kappa$-B inhibitors, CXR2 antagaonists, HLE inhibitors, HMG-CoA reductase inhibitors and the like.

Anti-inflammatory agents also include compounds that inhibit/decrease cell signaling by inflammatory molecules like cytokines (e.g., IL-1, IL-4, IL-5, IL-6, IL-9, IL-13, IL-18 IL-25, IFN-$\alpha$, IFN-$\beta$, and others), CC chemokines CCL-1-CCL28 (some of which are also known as, for example, MCP-1, CCL2, RANTES), CXC chemokines CXCL1-CXCL17 (some of which are also know as, for example, IL-8, MIP-2), growth factors (e.g., GM-CSF, NGF, SCF, TGF-$\beta$, EGF, VEGF and others) and/or their respective receptors.

Some examples of the aforementioned anti-inflammatory antagonists/inhibitors include ABN912 (MCP-1/CCL2, Novartis AG), AMG761 (CCR4, Amgen Inc), Enbrel® (TNF, Amgen Inc, Wyeth), huMAb OX40L GENENTECH (TNF superfamily, Genentech Inc, AstraZeneca PLC), R4930 (TNF superfamily, Roche Holding Ltd), SB683699/Firategrast (VLA4, GlaxoSmithKline PLC), CNT0148 (TNF$\alpha$, Centocor, Inc, Johnson & Johnson, Schering-Plough Corp); Canakinumab (IL-1$\beta$, Novartis); Israpafant MITSUBISHI (PAF/IL-5, Mitsubishi Tanabe Pharma Corporation); IL-4 and IL-4 receptor antagonists/inhibitors: AMG317 (Amgen Inc) and BAY169996 (Bayer AG), AER-003 (Aerovance), APG-201 (Apogenix); IL-5 and IL-5 receptor antagonists/inhibitors: MEDI563 (AstraZeneca PLC, MedImmune, Inc), Bosatria® (GlaxoSmithKline PLC), Cinquil® (Ception Therapeutic), TMC120B (Mitsubishi Tanabe Pharma Corporation), Bosatria (GlaxoSmithKline PLC), Reslizumab SCHERING (Schering-Plough Corp); MEDI528 (IL-9, AstraZeneca, MedImmune, Inc); IL-13 and IL-13 receptor antagonists/inhibitors: TNX650 GENENTECH (Genentech), CAT-354 (AstraZeneca PLC, MedImmune), AMG-317 (Takeda Pharmaceutical Company Limited), MK6105 (Merck & Co Inc), IMA-026 (Wyeth), IMA-638 Anrukinzumab (Wyeth), MILR1444A/Lebrikizumab (Genentech), QAX576 (Novartis), CNTO-607 (Centocor), MK-6105 (Merck, CSL); Dual IL-4 and IL-13 inhibitors: AIR645/ISIS369645 (ISIS Altair), DOM-0910 (GlaxoSmithKline, Domantis), Pitrakinra/AER001/Aerovant™ (Aerovance Inc), AMG-317 (Amgen), and the like.

Suitable steroids include corticosteroids, combinations of corticosteroids and LABAs, combinations of corticosteroids and LAMAs, combinations of corticosteroids, LABAs and LAMAs, and the like.

Suitable corticosteroids include budesonide, fluticasone, flunisolide, triamcinolone, beclomethasone, mometasone, ciclesonide, dexamethasone, and the like.

Examples of budesonide formulations include Captisol-Enabled® Budesonide Solution for Nebulization (AstraZeneca PLC), Pulmicort®(AstraZeneca PLC), Pulmicort® Flexhaler (AstraZeneca Plc), Pulmicort® HFA-MDI (AstraZeneca PLC), Pulmicort Respules® (AstraZeneca PLC), Inflammide (Boehringer Ingelheim GmbH), Pulmicort® HFA-MDI (SkyePharma PLC), Unit Dose Budesonide ASTRAZENECA (AstraZeneca PLC), Budesonide Modulite (Chiesi Farmaceutici S.p.A), CHF5188 (Chiesi Farmaceutici S.p.A), Budesonide ABBOTT LABS (Abbott Laboratories), Budesonide clickhaler (Vestura Group PLC), Miflonide (Novartis AG), Xavin (Teva Pharmaceutical Industries Ltd.), Budesonide TEVA (Teva Pharmaceutical Industries Ltd.), Symbicort® (AstraZeneca K.K., AstraZeneca PLC), VR632 (Novartis AG, Sandoz International GmbH), and the like.

Examples of fluticasone propionate formulations include Flixotide Evohaler (GlaxoSmithKline PLC), Flixotide Nebules (GlaxoSmithKline Plc), Flovent® (GlaxoSmithKline Plc), Flovent® Diskus (GlaxoSmithKline PLC), Flovent® HFA (GlaxoSmithKline PLC), Flovent® Rotadisk (GlaxoSmithKline PLC), Advair® HFA (GlaxoSmithKline PLC, Theravance Inc), Advair Diskus® (GlaxoSmithKline PLC, Theravance Inc.), VR315 (Novartis AG, Vectura Group PLC, Sandoz International GmbH), and the like. Other formulations of fluticasone include fluticasone as Flusonal (Laboratorios Almirall, S.A.), fluticasone furoate as GW685698 (GlaxoSmithKline PLC, Thervance Inc.), Plusvent (Laboratorios Almirall, S.A.), Flutiform® (Abbott Laboratories, SkyePharma PLC), and the like.

Examples of flunisolide formulations include Aerobid® (Forest Laboratories Inc), Aerospan® (Forest Laboratories Inc), and the like. Examples of triamcinolone include Triamcinolone ABBOTT LABS (Abbott Laboratories), Azmacort® (Abbott Laboratories, Sanofi-Aventis), and the like. Examples of beclomethasone dipropionate include Beclovent (GlaxoSmithKline PLC), QVAR® (Johnson & Johnson, Schering-Plough Corp, Teva Pharmacetucial Industries Ltd), Asmabec clickhaler (Vectura Group PLC), Beclomethasone TEVA (Teva Pharmaceutical Industries Ltd), Vanceril (Schering-Plough Corp), BDP Modulite (Chiesi Farmaceutici S.p.A.), Clenil (Chiesi Farmaceutici S.p.A), Beclomethasone dipropionate TEVA (Teva Pharmaceutical Industries Ltd), and the like. Examples of mometasone include QAB 149 Mometasone furoate (Schering-Plough Corp), QMF149 (Novartis AG), Fomoterol fumarate, mometoasone furoate (Schering-Plough Corp), MFF258 (Novartis AG, Merck & Co Inc), Asmanex® Twisthaler (Schering-Plough Corp), and the like. Examples of cirlesonide include Alvesco® (Nycomed International Management GmbH, Sepracor, Sanofi-Aventis, Tejin Pharma Limited), Alvesco® Combo (Nycomed International Management GmbH, Sanofi-Aventis), Alvesco® HFA (Nycomed Intenational Management GmbH, Sepracor Inc), and the like. Examples of dexamethasone include DexPak® (Merck), Decadron® (Merck), Adrenocot, CPC-Cort-D, Decaject-10, Solurex and the like. Other corticosteroids include Etiprednol dicloacetate TEVA (Teva Pharmaceutical Industries Ltd), and the like.

Combinations of corticosteroids and LABAs include salmeterol with fluticasone, formoterol with budesonide, formoterol with fluticasone, formoterol with mometasone, indacaterol with mometasone, and the like.

Examples of salmeterol with fluticasone include Plusvent (Laboratorios Almirall, S.A.), Advair® HFA (GlaxoSmithKline PLC), Advair® Diskus (GlaxoSmithKline PLV, Theravance Inc), VR315 (Novartis AG, Vectura Group PLC, Sandoz International GmbH) and the like. Examples of formoterol with budesonide include Symbicort® (AstraZeneca PLC), VR632 (Novartis AG, Vectura Group PLC), and the like. Examples of vilanterol with fluticasone include GSK642444 with fluticasone and the like. Examples of formoterol with fluticasone include Flutiform® (Abbott Laboratories, SkyePharma PLC), and the like. Examples of formoterol with mometasone include Dulera®/MFF258 (Novartis AG, Merck & Co Inc), and the like. Examples of indacaterol with mometasone include QAB149 Mometasone furoate (Schering-Plough Corp), QMF149 (Novartis AG), and the like. Combinations of corticosteroids with LAMAs include fluticasone with tiotropium, budesonide with tiotropium, mometasone with tiotropium, salmeterol with tiotropium, formoterol with tiotropium, indacaterol with tiotropium, vilanterol with tiotropium, and the like. Combinations of corticosteroids with LAMAs and LABAs include, for example, fluticasone with salmeterol and tiotropium.

Other anti-asthma molecules include: ARD111421 (VIP agonist, AstraZeneca PLC), AVE0547 (anti-inflammatory, Sanofi-Aventis), AVE0675 (TLR agonist, Pfizer, Sanofi-Aventis), AVE0950 (Syk inhibitor, Sanofi-Aventis), AVE5883 (NK1/NK2 antagonist, Sanofi-Aventis), AVE8923 (tryptase beta inhibitor, Sanofi-Aventis), CGS21680 (adenosine A2A receptor agonist, Novartis AG), ATL844 (A2B receptor antagonist, Novartis AG), BAY443428 (tryptase inhibitor, Bayer AG), CHF5407 (M3 receptor inhibitor, Chiesi Farmaceutici S.p.A.), CPLA2 Inhibitor WYETH (CPLA2 inhibitor, Wyeth), IMA-638 (IL-13 antagonist, Wyeth), LAS100977 (LABA, Laboratorios Almirall, S.A.), MABA (M3 and β2 receptor antagonist, Chiesi Farmaceutici S.p.A), R1671 (mAb, Roche Holding Ltd), CS003 (Neurokinin receptor antagonist, Daiichi Sankyo Company, Limited), DPC168 (CCR antagonist, Bristol-Myers Squibb), E26 (anti-IgE, Genentech Inc), HAE1 (Genentech), IgE inhibitor AMGEN (Amgen Inc), AMG853 (CRTH2 and D2 receptor antagonist, Amgen), IPL576092 (LSAID, Sanofi-Aventis), EPI2010 (antisense adenosine 1, Chiesi Farmaceutici S.p.A.), CHF5480 (PDE-4 inhibitor, Chiesi Farmaceutici S.p.A.), KI04204 (corticosteroid, Abbott Laboratories), SVT47060 (Laboratorios Salvat, S.A.), VML530 (leukotriene synthesis inhibitor, Abbott Laboratories), LAS35201 (M3 receptor antagonist, Laboratorios Almirall, S.A.), MCC847 (D4 receptor antagonist, Mitsubishi Tanabe Pharma Corporation), MEM1414 (PDE-4 inhibitor, Roche), TA270 (5-LO inhibitor, Chugai Pharmaceutical Co Ltd), TAK661 (eosinophil chemotaxis inhibitor, Takeda Pharmaceutical Company Limited), TBC4746 (VLA-4 antagonist, Schering-Plough Corp), VR694 (Vectura Group PLC), PLD177 (steroid, Vectura Group PLC), KI03219 (corticosteroid+LABA, Abbott Laboratories), AMG009 (Amgen Inc), AMG853 (D2 receptor antagonist, Amgen Inc);

AstraZeneca PLC: AZD1744 (CCR3/histamine-1 receptor antagonist, AZD1419 (TLR9 agonist), Mast Cell inhibitor ASTRAZENECA, AZD3778 (CCR antagonist), DSP3025 (TLR7 agonist), AZD1981 (CRTh2 receptor antagonist), AZD5985 (CRTh2 antagonist), AZD8075 (CRTh2 antagonist), AZD1678, AZD2098, AZD2392, AZD3825 AZD8848, AZD9215, ZD2138 (5-LO inhibitor), AZD3199 (LABA);

GlaxoSmithKline PLC: GW328267 (adenosine A2 receptor agonist), GW559090 (α4 integrin antagonist), GSK679586 (mAb), GSK597901 (adrenergic β2 agonist), AM103 (5-LO inhibitor), GSK256006 (PDE4 inhibitor), GW842470 (PDE-4 inhibitor), GSK870086 (glucocorticoid agonist), GSK159802 (LABA), GSK256066 (PDE-4 inhibitor), GSK642444 (LABA, adrenergic β2 agonist), GSK64244 and Revolair (fluticasone/vilanterol), GSK799943 (corticosteroid), GSK573719 (mAchR antagonist), and GSK573719;

Pfizer Inc: PF3526299, PF3893787, PF4191834 (FLAP antagonist), PF610355 (adrenergic β2 agonist), CP664511 (α4β1/VCAM-1 interaction inhibitor), CP609643 (inhibitor of α4β1/VCAM-1 interactions), CP690550 (JAK3 inhibitor), SAR21609 (TLR9 agonist), AVE7279 (Th1 switching), TBC4746 (VLA-4 antagonist); R343 (IgE receptor signaling inhibitor), SEP42960 (adenosine A3 antagonist);

Sanofi-Aventis: MLN6095 (CrTH2 inhibitor), SAR137272 (A3 antagonist), SAR21609 (TLR9 agonist), SAR389644 (DP1 receptor antagonist), SAR398171 (CRTH2 antagonist), SSR161421 (adenosine A3 receptor antagonist);

Merck & Co Inc: MK0633, MK0633, MK0591 (5-LO inhibitor), MK886 (leukotriene inhibitor), BIO1211 (VLA-4 antagonist); Novartis AG: QAE397 (long-acting corticosteroid), QAK423, QAN747, QAP642 (CCR3 antagonist), QAX935 (TLR9 agonist), NVA237 (LAMA).

Suitable expectorants include guaifenesin, guaiacolculfonate, ammonium chloride, potassium iodide, tyloxapol, antimony pentasulfide and the like.

Suitable vaccines include nasally inhaled influenza vaccines and the like.

The active agent can also be selected from the group consisting of transient receptor potential (TRP) channel agonists. In certain embodiments, the TRP agonist is a TRPC, TRPV, TRPM and/or TRPA1 subfamily agonist. In some embodiments, the TRP channel agonist is selected from the group consisting of TRPV2, TRPV3, TRPV4, TRPC6, TRPM6, and/or TRPA1 agonist. Suitable TRP channel agonists may be selected from the group consisting of allyl isothiocyanate (AITC), benyzl isothiocyanate (BITC), phenyl isothiocyanate, isopropyl isothiocyanate, methyl isothiocyanate, diallyl disulfide, acrolein (2-propenal), disulfuram (Antabuse®), farnesyl thiosalicylic acid (FTS), farnesyl thioacetic acid (FTA), chlodantoin (Sporostacin®, topical fungicidal), (15-d-PGJ2), 5,8,11,14 eicosatetraynoic acid (ETYA), dibenzoazepine, mefenamic acid, fluribiprofen, keoprofen, diclofenac, indomethacin, SC alkyne (SCA), pentenal, mustard oil alkyne (MOA), iodoacetamine, iodoacetamide alkyne, (2-aminoethyl) methanethiosulphonate (MTSEA), 4-hydroxy-2-noneal (HNE), 4-hydroxy xexenal (HHE), 2-chlorobenzalmalononitrile, N-chloro tosylamide (chloramine-T), formaldehyde, isoflurane, isovelleral, hydrogen peroxide, URB597, thiosulfinate, Allicin (a specific thiosulfinate), flufenamic acid, niflumic acid, carvacrol, eugenol, menthol, gingerol, icilin, methyl salicylate, arachidonic acid, cinnemaldehyde, super sinnemaldehyde, tetrahydrocannabinol (THC or $\Delta^9$-THC), cannabidiol (CBD), cannabichromene (CBC), cannabigerol (CBG), THC acid (THC-A), CBD acid (CBD-A), Compound 1 (AMG5445), 4-methyl-N-[2,2,2-trichloro-1-(4-chlorophenylsulfanyl)ethyl]benzamide, N-[2,2,2-trichloro-1-(4-chlorophenylsulfanyl)ethyl]acetamid, AMG9090, AMG5445, 1-oleoyl-2-acetyl-sn-glycerol (OAG), carbachol, diacylglycerol (DAG), 1,2-Didecanoylglycerol, flufenamate/flufenamic acid, niflumate/niflumic acid, hyperforin, 2-aminoethoxydiphenyl borate (2-APB), diphenylborinic anhydride (DPBA), delta-9-tetrahydrocannabinol ($\Delta^9$-THC or THC), cannabiniol (CBN), 2-APB, O-1821, 11-hydroxy-$\Delta$9-tetrahydrocannabinol, nabilone, CP55940, HU-210, HU-211/dexanabinol, HU-331, HU-308, JWH-015, WIN55, 212-2,2-Arachidonoylglycerol (2-AG), Arvil, PEA, AM404, O-1918, JWH-133, incensole, incensole acetate, menthol, eugenol, dihydrocarveol, carveol, thymol, vanillin, ethyl vanillin, cinnemaldehyde, 2 aminoethoxydiphenyl borate (2-APB), diphenylamine (DPA), diphenylborinic anhydride (DPBA), camphor, (+)-borneol, (−)-isopinocampheol, (−)-fenchone, (−)-trans-pinocarveol, isoborneol, (—O-camphorquinone, (−)-α-thujone, α-pinene oxide, 1,8-cineole/eucalyptol, 6-butyl-m-cresol, carvacrol, p-sylenol, kreosol, propofol, p-cymene, (−)-isoppulegol, (−)-carvone, (+)-dihydrocarvone, (−)-menthone, (+)-linalool, geraniol, 1-isopropyl-4-methylbicyclo[3.1.0]hexan-4-ol, 4αPDD, GSK1016790A, 5'6'Epoxyeicosatrienoic (5'6'-EET), 8'9'Epoxyeicosatrienoic (8'9'-EET), APP44-1, RN1747, Formulation Ib WO200602909, Formulation IIb WO200602909, Formulation IIc WO200602929, Formulation IId WO200602929, Formulation IIb WO200602929, Formulation IIIc WO200602929, arachidonic acid (AA), 12-O-Tetradecanoylphorbol-13-acetate (TPA)/phorbol 12-myristate 13-acetate (PMA), bisandrographalide (BAA), incensole, incensole acetate, Compound IX WO2010015965, Compound X WO2010015965, Compound XI WO2010015965, Compound XII WO2010015965, WO2009004071, WO2006038070, WO2008065666, Formula VII WO2010015965, Formula IV WO2010015965, dibenzoazepine, dibenzooxazepine, Formula I WO2009071631, N-{(1S)-1-[({(4R)-1-[(4-chlorophenyl)sulfonyl]-3-oxohexahydro-1H-azepin-4-yl}amino)carbonyl]-3-methylbutyl}-1-benzothiophen-2-carboxamide, N-{(1S)-1-[({(4R)-1-[(4-fluorophenyl)sulfonyl]-3-oxohexahydro-1H-azepin-4-yl}amino)carbonyl]-3-methylbutyl}-1-benzothiophen-2-carboxamide, N-{(1S)-1-[({(4R)-1-[(2-cyanophenyl)sulfonyl]-3-oxohexahydro-1H-azepin-4-yl}amino)carbonyl]-3-methylbutyl}-1-methyl-1H-indole-2-carboxamide, and N-{(1S)-1-[({(4R)-1-[(2-cyanophenyl)sulfonyl]hexahydro-1H-azepin-4-yl}amino)carbonyl]-3-methylbutyl}-1-methyl-1H-indole-2-carboxamide.

Suitable macromolecules include proteins and large peptides, polysaccharides and oligosaccharides, DNA and RNA nucleic acid molecules and their analogs having therapeutic, prophylactic or diagnostic activities. Proteins can include growth factors, hormones, cytokines (e.g., chemokines) and antibodies. As used herein, antibodies can include: all types of immunoglobulins, e.g., IgG, IgM, IgA, IgE, IgD, etc., from any source, e.g., human, rodent, rabbit, cow, sheep, pig, dog, other mammals, chicken, other avian, aquatic animal species etc., monoclonal and polyclonal antibodies, single chain antibodies (including IgNAR (single-chain antibodies derived from sharks)), chimeric antibodies, bifunctional/bispecific antibodies, humanized antibodies, human antibodies, and complementary determining region (CDR)-grafted antibodies, that are specific for the target protein or fragments thereof, and also include antibody fragments, including Fab, Fab', F(ab')2, scFv, Fv, camelbodies, microantibodies, nanobodies, and small-modular immunopharmaceuticals (SMIPs). Nucleic acid molecules include DNA, e.g., encoding genes or gene fragments, or RNA, including mRNA, antisense molecules, such as antisense RNA, RNA molecules involved in RNA interference (RNAi), such as microRNA (miRNA), small interfering RNA (siRNA) and small hairpin RNA (shRNA), ribozymes or other molecules capable of inhibiting transcription and/or translation. Preferred macromolecules have a molecular weight of at least 800 Da, at least 3000 Da or at least 5000 Da.

In preferred embodiments, the respirable dry powder or respirable dry particle comprises a therapeutic antibody. In certain preferred embodiments, the antibody is a monoclonal antibody. In certain preferred embodiments, the antibody is a single chain antibody, a chimeric antibody, a bifunctional/bispecific antibody, a humanized antibody, or a combination thereof. In preferred embodiments, the antibody is selected from the group consisting of: monoclonal antibodies, e.g., Abciximab (ReoPro®, chimeric), Adalimumab (Humira®, human), Alemtuzumab (Campath®, humanized), Basiliximab (Simulect®, chimeric), Belimumab (Benlysta®, human), Bevacizumab (Avastin®, humanized), Brentuximab vedotin (Adcetris®, chimeric), Canakinumab (Ilaris®, human), Cetuximab (Erbitux®, chimeric), Certolizumab pegol (Cimzia®, humanized), Daclizumab (Zenapax®, humanized), Denosumab (Prolia®, Xgeva®, human), Eculizumab (Soliris®, humanized), Efalizumab (Raptiva®, humanized), Gemtuzumab (Mylotarg®, humanized), Golimumab (Simponi®, human), Ibritumomab tiuxetan (Zevalin®, murin), Infliximab (Remicade®, chimeric), Ipilimumab (MDX-101) (Yervoy®, human), Muromonab-CD3 (Orthoclone OKT3, murine), Natalizumab (Tysabri®, humanized), Ofatumumab (Arzerra®, human), Omalizumab (Xolair®, humanized), Palivizumab (Synagis®, humanized), Panitumumab (Vectibix®, human), Ranibizumab (Lucentis®, humanized), Rituximab (Rituxan®, Mabthera®, chimeric), Tocilizumab (or Atlizumab) (Actemra® and RoActemra®, humanized), Tositumomab (Bexxar®, murine), Trastuzumab (Herceptin®, humanized), and bispecific antibodies, e.g., catumaxomab (Removab®, rat-mouse hybrid monoclonal antibody).

Selected macromolecule active agents for systemic applications include, but are not limited to: Ventavis® (Iloprost), Calcitonin, Erythropoietin (EPO), Factor IX, Granulocyte Colony Stimulating Factor (G-CSF), Granulocyte Macrophage Colony, Stimulating Factor (GM-CSF), Growth Hormone, Insulin, TGF-beta, Interferon Alpha, Interferon Beta, Interferon Gamma, Luteinizing Hormone Releasing Hormone (LHRH), follicle stimulating hormone (FSH), Ciliary Neurotrophic Factor, Growth Hormone Releasing Factor (GRF), Insulin-Like Growth Factor, Insulinotropin, Interleukin-1 Receptor Antagonist, Interleukin-3, Interleukin-4, Interleukin-6, Macrophage Colony Stimulating Factor (M-CSF), Thymosin Alpha 1, IIb/IIIa Inhibitor, Alpha-1 Antitrypsin, Anti-RSV Antibody, palivizumab, motavizumab, and ALN-RSV, Cystic Fibrosis Transmembrane Regulator (CFTR) Gene, Deoxyribonuclease (DNase), Heparin, Bactericidal/Permeability Increasing Protein (BPI), Anti-Cytomegalovirus Receptor Antagonist, and the like, alpha-defensins (e.g., human neutrophil proteins (HNPs): HNP1, 2, 3, and 4; human defensins 5 and 6 (HD5 and HD6)), beta-defensins (HBD1, 2, 3, and 4), or Θ-defensins/retrocyclins, GLP-1 analogs (liraglutide, exenatide, etc.), Domain antibodies (dAbs), Pramlintide acetate (Symlin), Leptin analogs, Synagis (palivizumab, MedImmune) and cisplatin. In certain preferred embodiments, the respirable dry powder or respirable dry particle comprises a macromolecule involved in intra- or inter-cellular signaling, such as a growth factor, a cytokine, a chemokine or a hormone. In preferred embodiments, the respirable dry powder or respirable dry particle comprises a hormone. In certain preferred embodiments, the hormone is insulin.

Selected therapeutics helpful for chronic maintenance of CF include antibiotics/macrolide antibiotics, bronchodilators, inhaled LABAs, and agents to promote airway secretion clearance. Suitable examples of antibiotics/macrolide antibiotics include tobramycin, azithromycin, ciprofloxacin, colistin, aztreonam and the like. Another exemplary antibiotic/macrolide is levofloxacin. Suitable examples of bronchodilators include inhaled short-acting $beta_2$ agonists such as albuterol, and the like. Suitable examples of inhaled LABAs include salmeterol, formoterol, and the like. Suitable examples of agents to promote airway secretion clearance include Pulmozyme (dornase alfa, Genentech) hypertonic saline, DNase, heparin, and the like. Selected therapeutics helpful for the prevention and/or treatment of CF include VX-770 (Vertex Pharmaceuticals) and amiloride.

Selected therapeutics helpful for the treatment of idiopathic pulmonary fibrosis include Metelimumab (CAT-192) (TGF-β1 mAb inhibitor, Genzyme), Aerovant™ (AER001, pitrakinra) (Dual IL-13, IL-4 protein antagonist, Aerovance), Aeroderm™ (PEGylated Aerovant, Aerovance), microRNA, RNAi, and the like.

In preferred embodiments, the respirable dry powder or respirable dry particle comprises an antibiotic, such as a macrolide (e.g., azithromycin, clarithromycin and erythromycin), a tetracycline (e.g., doxycycline, tigecycline), a fluoroquinolone (e.g., gemifloxacin, levofloxacin, ciprofloxacin and mocifloxacin), a cephalosporin (e.g., ceftriaxone, defotaxime, ceftazidime, cefepime), a penicillin (e.g., amoxicillin, amoxicillin with clavulanate, ampicillin, piperacillin, and ticarcillin) optionally with a β-lactamase inhibitor (e.g., sulbactam, tazobactam and clavulanic acid), such as ampicillin-sulbactam, piperacillin-tazobactam and ticarcillin with clavulanate, an aminoglycoside (e.g., amikacin, arbekacin, gentamicin, kanamycin, neomycin, netilmicin, paromomycin, rhodostreptomycin, streptomycin, tobramycin, and apramycin), a penem or carbapenem (e.g., doripenem, ertapenem, imipenem and meropenem), a monobactam (e.g., aztreonam), an oxazolidinone (e.g., linezolid), vancomycin, glycopeptide antibiotics (e.g., telavancin), tuberculosis-mycobacterium antibiotics, tobramycin, azithromycin, ciprofloxacin, colistin, and the like. In a preferred embodiment, the respirable dry powder or respirable dry particle comprises levofloxacin. In another preferred embodiment, the respirable dry powder or respirable dry particle comprises aztreonam (i.e., Cayston®) or a pharmaceutically acceptable salt thereof. In a further preferred embodiment, the respirable dry powder or respirable dry particle does not comprise tobramycin. In another embodiment, the respirable dry powder or respirable dry particle does not comprise levofloxacin. In another embodiment, the respirable dry powder or respirable dry particle does not comprise Cayston®.

In preferred embodiments, the respirable dry powder or respirable dry particle comprises a LABA, such as salmeterol, formoterol and isomers (e.g., arformoterol), clenbuterol, tulobuterol, vilanterol (Revolair™), indacaterol, carmoterol, isoproterenol, procaterol, bambuterol, milveterol, and the like. In a further preferred embodiment, the respirable dry powder or respirable dry particle comprises formoterol. In a further preferred embodiment, the respirable dry powder or respirable dry particle comprises salmeterol. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNase), sodium channel blockers (e.g., amiloride), and combinations thereof.

In preferred embodiments, the respirable dry powder or respirable dry particle comprises a LAMA, such as tiotropium, glycopyrrolate, aclidinium, ipratropium and the like. In a further preferred embodiment, the respirable dry powder or respirable dry particle comprises tiotropium.

In preferred embodiments, the respirable dry powder or respirable dry particle comprises a corticosteroid, such as budesonide, fluticasone, flunisolide, triamcinolone, beclomethasone, mometasone, ciclesonide, dexamethasone, and the like. In a further preferred embodiment, the respirable dry powder or respirable dry particle comprises fluticasone.

Preferred additional therapeutic agents are LABAs (e.g., formoterol, salmeterol), short-acting beta agonists (e.g., albuterol), corticosteroids (e.g., fluticasone), LAMAs (e.g., tiotropium), antibiotics (e.g., levofloxacin, tobramycin), and combinations thereof. When the dry powders are intended for treatment of CF, preferred additional therapeutic agents are short-acting beta agonists (e.g., albuterol), antibiotics (e.g., levofloxacin), recombinant human deoxyribonuclease I (e.g., dornase alfa, also known as DNAse), sodium channel blockers (e.g., amiloride), and combinations thereof.

In preferred embodiments, the respirable dry powder or respirable dry particle comprises a combination of two or more of the following; a LABA, a LAMA, and a corticosteroid. In a further preferred embodiment, the respirable dry powder or respirable dry particle comprises fluticasone and salmeterol. In a further preferred embodiment, the respirable dry powder or respirable dry particle comprises fluticasone, salmeterol, and tiotropium.

When an additional therapeutic agent is administered to a patient with a dry powder or dry particles disclosed herein, the agent and the dry powder or dry particles are administered to provide overlap of the therapeutic effect of the additional therapeutic agent with the administration of the dry powder or dry particles. For example, a LABA such as formoterol, or a short-acting beta agonist such as albuterol can be administered to the patient before a dry powder or dry particle, as described herein, is administered.

Dry Powder and Dry Particle Properties

The dry particles of the invention are small and dispersible, and preferably dense (e.g., active agent dense and/or mass dense). Generally, the dry particles of the invention have a VMGD as measured by HELOS/RODOS at 1.0 bar of about 10 μm or less (e.g., about 0.1 μm to about 10 μm). Preferably, the dry particles of the invention have an VMGD of about 9 μm or less (e.g., about 0.1 μm to about 9 μm), about 8 μm or less (e.g., about 0.1 μm to about 8 μm), about 7 μm or less (e.g., about 0.1 μm to about 7 μm), about 6 μm or less (e.g., about 0.1 μm to about 6 μm), about 5 μm or less (e.g., less than 5 μm, about 0.1 μm to about 5 μm), about 4 μm or less (e.g., 0.1 μm to about 4 μm), about 3 μm or less (e.g., 0.1 μm to about 3 μm), about 2 μm or less (e.g., 0.1 μm to about 2 µm), about 1 µm or less (e.g., 0.1 µm to about 1 µm), about 1 µm to about 6 µm, about 1 µm to about 5 µm, about 1 µm to about 4 µm, about 1 µm to about 3 µm, or about 1 µm to about 2 µm as measured by HELOS/RODOS at 1.0 bar.

In another aspect, the dry particles of the invention are large and preferably dense (e.g., active agent dense), and are dispersible. Generally, the dry particles of the invention have a VMGD as measured by HELOS/RODOS at 1.0 bar of about 30 µm or less (e.g., about 5 µm to about 30 µm). Preferably, the dry particles of the invention have an VMGD of about 25 µm or less (e.g., about 5 µm to about 25 µm), about 20 µm or less (e.g., about 5 µm to about 20 µm), about 15 µm or less (e.g., about 5 µm to about 15 µm), about 12 µm or less (e.g., about 5 µm to about 12 µm), about 10 µm or less (e.g., about 5 µm to about 10 µm), or about 8 µm or less (e.g., 6 µm to about 8 µm) as measured by HELOS/RODOS at 1.0 bar.

The respirable dry powders of the invention can have poor flow properties, such as bulk flow properties, for example as assessed by Hausner Ratio, as described herein. Yet, surprisingly, the powders are highly dispersible. This is surprising because flow properties and dispersibility are both known to be negatively affected by particle agglomeration or aggregation. Thus, it was unexpected that particles that have poor flow characteristics, such as bulk flow characteristics, would be highly dispersible.

Generally, the respirable dry powders can have a Hausner Ratio that is greater than 1.5, and can be 1.6 or higher, 1.7 or higher, 1.8 or higher, 1.9 or higher, 2 or higher, 2.1 or higher, 2.2 or higher, 2.3 or higher, 2.4 or higher, 2.5 or higher, 2.6 or higher or 2.7 or higher, between 2.2 and 2.9, between 2.2 and 2.8, between 2.2 and 2.7, between 2.2 and 2.6, between 2.2 and 2.5, between 2.3 and 2.5, between 2.6 and 2.8, about 2.7, or about 2.4.

The dry particles of the invention are dispersible, and have 1 bar/4 bar and/or 0.5 bar/4 bar of about 2.2 or less (e.g., about 1.0 to about 2.2) or about 2.0 or less (e.g., about 1.0 to about 2.0). Preferably, the dry particles of the invention have 1 bar/4 bar and/or 0.5 bar/4 bar of about 1.9 or less (e.g., about 1.0 to about 1.9), about 1.8 or less (e.g., about 1.0 to about 1.8), about 1.7 or less (e.g., about 1.0 to about 1.7), about 1.6 or less (e.g., about 1.0 to about 1.6), about 1.5 or less (e.g., about 1.0 to about 1.5), about 1.4 or less (e.g., about 1.0 to about 1.4), about 1.3 or less (e.g., less than 1.3, about 1.0 to about 1.3), about 1.2 or less (e.g., 1.0 to about 1.2), about 1.1 or less (e.g., 1.0 to about 1.1 µm) or the dry particles of the invention have 1 bar/4 bar and/or 0.5 bar/4 bar of about 1.0.

Alternatively or in addition, the respirable dry particles of the invention can have an MMAD of about 10 microns or less, such as an MMAD of about 0.5 micron to about 10 microns. Preferably, the dry particles of the invention have an MMAD of about 5 microns or less (e.g., about 0.5 micron to about 5 microns, preferably about 1 micron to about 5 microns), about 4 microns or less (e.g., about 1 micron to about 4 microns), about 3.8 microns or less (e.g., about 1 micron to about 3.8 microns), about 3.5 microns or less (e.g., about 1 micron to about 3.5 microns), about 3.2 microns or less (e.g., about 1 micron to about 3.2 microns), about 3 microns or less (e.g., about 1 micron to about 3.0 microns), about 2.8 microns or less (e.g., about 1 micron to about 2.8 microns), about 2.2 microns or less (e.g., about 1 micron to about 2.2 microns), about 2.0 microns or less (e.g., about 1 micron to about 2.0 microns) or about 1.8 microns or less (e.g., about 1 micron to about 1.8 microns).

Alternatively or in addition, the respirable dry powders and dry particles of the invention can have an FPF of less than about 5.6 microns of the total dose (FPF<5.6 µm) of at least about 20%, at least about 30%, at least about 40%, preferably at least about 45%, at least about 50%, at least about 55%, at least about 60%, at least about 65%, or at least about 70%.

Alternatively or in addition, the dry powders and dry particles of the invention have a FPF of less than 5.0 microns (FPF_TD<5.0 µm) of at least about 20%, at least about 30%, at least about 45%, preferably at least about 40%, at least about 45%, at least about 50%, at least about 60%, at least about 65% or at least about 70%. Alternatively or in addition, the dry powders and dry particles of the invention have a FPF of less than 5.0 microns of the emitted dose (FPF_ED<5.0 µm) of at least about 45%, preferably at least about 50%, at least about 60%, at least about 65%, at least about 70%, at least about 75%, at least about 80%, or at least about 85%. Alternatively or in addition, the dry powders and dry particles of the invention can have an FPF of less than about 3.4 microns (FPF<3.4 µm) of at least about 20%, preferably at least about 25%, at least about 30%, at least about 35%, at least about 40%, at least about 45%, at least about 50%, or at least about 55%.

Alternatively or in addition, the respirable dry powders and dry particles of the invention have a tap density of about 0.1 g/cm$^3$ to about 1.0 g/cm$^3$. For example, the small and dispersible dry particles have a tap density of about 0.1 g/cm$^3$ to about 0.9 g/cm$^3$, about 0.2 g/cm$^3$ to about 0.9 g/cm$^3$, about 0.2 g/cm$^3$ to about 0.9 g/cm$^3$, about 0.3 g/cm$^3$ to about 0.9 g/cm$^3$, about 0.4 g/cm$^3$ to about 0.9 g/cm$^3$, about 0.5 g/cm$^3$ to about 0.9 g/cm$^3$, or about 0.5 g/cm$^3$ to about 0.8 g/cm$^3$, greater than about 0.4 g/cc, greater than about 0.5 g/cc, greater than about 0.6 g/cc, greater than about 0.7 g/cc, about 0.1 g/cm$^3$ to about 0.8 g/cm$^3$, about 0.1 g/cm$^3$ to about 0.7 g/cm$^3$, about 0.1 g/cm$^3$ to about 0.6 g/cm$^3$, about 0.1 g/cm$^3$ to about 0.5 g/cm$^3$, about 0.1 g/cm$^3$ to about 0.4 g/cm$^3$, about 0.1 g/cm$^3$ to about 0.3 g/cm$^3$, less than 0.3 g/cm$^3$. In a preferred embodiment, tap density is greater than about 0.4 g/cc. In another preferred embodiment, tap density is greater than about 0.5 g/cc. Alternatively, tap density is less than about 0.4 g/cc.

Alternatively or in addition, the respirable dry powders and dry particles of the invention can have a water or solvent content of less than about 15% by weight of the respirable dry particle. For example, the respirable dry particles of the invention can have a water or solvent content of less than about 15% by weight, less than about 13% by weight, less than about 11.5% by weight, less than about 10% by weight, less than about 9% by weight, less than about 8% by weight, less than about 7% by weight, less than about 6% by weight, less than about 5% by weight, less than about 4% by weight, less than about 3% by weight, less than about 2% by weight, less than about 1% by weight or be anhydrous. The respirable dry particles of the invention can have a water or solvent content of less than about 6% and greater than about 1%, less than about 5.5% and greater than about 1.5%, less than about 5% and greater than about 2%, about 2%, about 2.5%, about 3%, about 3.5%, about 4%, about 4.5% about 5%.

The respirable dry particles can be characterized by the crystalline and amorphous content of the particles. The respirable dry particles can comprise a mixture of amorphous and crystalline content, in which the divalent metal cation salt, e.g., calcium salt and/or magnesium salt, is substantially in the amorphous phase. If a monovalent salt is present, e.g., a sodium salt, it can be substantially in the crystalline phase. As described herein, the respirable dry particles can further comprise an excipient, such as leucine, maltodextrin or mannitol, and/or a pharmaceutically active agent. The excipient and pharmaceutically active agent can independently be crystalline or amorphous or present in a combination of these forms. In some embodiments, the excipient is amorphous or predominately amorphous.

This provides several advantages. For example, the crystalline phase (e.g., crystalline sodium chloride) can contribute to the stability of the dry particle in the dry state and to the dispersibility characteristics, whereas the amorphous phase (e.g., amorphous active agent and/or excipient) can facilitate rapid water uptake and dissolution of the particle upon deposition in the respiratory tract. It is particularly advantageous when salts with relatively high aqueous solubilities (such as sodium chloride) that are present in the dry particles are in a crystalline state and when salts with relatively low aqueous solubilities (such as calcium citrate) are present in the dry particles in an amorphous state.

The amorphous phase can be characterized by a high glass transition temperature ($T_g$), such as a $T_g$ of at least 90° C., at least 100° C., at least 105° C., at least 110° C., at least 115° C., 120° C., at least 125° C., at least 130° C., at least 135° C., at least 140° C., between 120° C. and 200° C., between 125° C. and 200° C., between 130° C. and 200° C., between 120° C. and 190° C., between 125° C. and 190° C., between 130° C. and 190° C., between 120° C. and 180° C., between 125° C. and 180° C., or between 130° C. and 180° C. Alternatively, the amorphous phase can be characterized by a high $T_g$ such as at least 80° C. or at least 90° C.

In some embodiments, the respirable dry particles contain an excipient and or active agent rich amorphous phase and a monovalent salt (sodium salt, potassium salt) crystalline phase and the ratio of amorphous phase to crystalline phase (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain an amorphous phase and a monovalent salt crystalline phase and the ratio of amorphous phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5. In other embodiments, the respirable dry particles contain an amorphous phase and a monovalent salt crystalline phase and the ratio of crystalline phase to particle by weight (w:w) is about 5:95 to about 95:5, about 5:95 to about 10:90, about 10:90 to about 20:80, about 20:80 to about 30:70, about 30:70 to about 40:60, about 40:60 to about 50:50; about 50:50 to about 60:40, about 60:40 to about 70:30, about 70:30 to about 80:20, or about 90:10 to about 95:5.

In addition to any of the features and properties described herein, in any combination, the respirable dry particles can have a heat of solution that is not highly exothermic. Preferably, the heat of solution is determined using the ionic liquid of a simulated lung fluid (e.g., as described in Moss, O.R. 1979. Simulants of lung interstitial fluid. Health Phys. 36, 447-448; or in Sun, G. 2001. Oxidative interactions of synthetic lung epithelial lining fluid with metal-containing particulate matter. Am J Physiol Lung Cell Mol. Physiol. 281, L807-L815) at pH 7.4 and 37° C. in an isothermal calorimeter. For example, the respirable dry particles can have a heat of solution that is less exothermic than the heat of solution of calcium chloride dihydrate, e.g., have a heat of solution that is greater than about −10 kcal/mol, greater than about −9 kcal/mol, greater than about −8 kcal/mol, greater than about −7 kcal/mol, greater than about −6 kcal/mol, greater than about −5 kcal/mol, greater than about −4 kcal/mol, greater than about −3 kcal/mol, greater than about −2 kcal/mol, greater than about −1 kcal/mol or about −10 kcal/mol to about 10 kcal/mol. Alternatively, a preferred ΔH is between about −9 kcal/mol and about 9 kcal/mol, between about −8 kcal/mol and about 8 kcal/mol, between about −7 kcal/mol and about 7 kcal/mol, between about −6 kcal/mol and about 6 kcal/mol, between about −5 kcal/mol and about 5 kcal/mol, between about −4 kcal/mol and about 4 kcal/mol, between about −3 kcal/mol and about 3 kcal/mol, between about −2 kcal/mol and about 2 kcal/mol, between about −1 kcal/mol and about 1 kcal/mol, or about 0 kcal/mol.

The respirable dry powders and dry particles are characterized by a high emitted dose (e.g., CEPM of at least 40%, at least 45%, at least 50%, at least 55%, at least 60%, at least 65%, at least 70%, at least 75%, at least 80%, at least 85%, at least 90%, at least 95%) from a dry powder inhaler when a total inhalation energy of less than about 2 Joules or less than about 1 Joule, or less than about 0.8 Joule, or less than about 0.5 Joule, or less than about 0.3 Joule is applied to the dry powder inhaler. For example, an emitted dose of at at least 75%, at least 80%, at least 85%, at least 90%, at least 95% CEPM of respirable dry powder contained in a unit dose container, containing about 50 mg of the appropriate formulation, in a dry powder inhaler can be achieved when a total inhalation energy of less than about 1 Joule (e.g., less than about 0.8 Joule, less than about 0.5 Joule, less than about 0.3 Joule) is applied to the dry powder inhaler. An emitted dose of at least about 70% CEPM of Formulation I or Formulation II contained in a unit dose container, containing about 50 mg of the appropriate formulation, in a dry powder inhaler can be achieved when a total inhalation energy of less than about 0.28 Joule is applied to the dry powder inhaler. The dry powder can fill the unit dose container, or the unit dose container can be at least 40% full, at least 50% full, at least 60% full, at least 70% full, at least 80% full, or at least 90% full. The unit dose container can be a capsule (e.g., size 000, 00, 0E, 0, 1, 2, 3, and 4, with respective volumetric capacities of 1.37 ml, 950 µl, 770 µl, 680 µl, 480 µl, 360 µl, 270 µl, and 200 µl).

Healthy adult populations are predicted to be able to achieve inhalation energies ranging from 2.9 Joules for comfortable inhalations to 22 Joules for maximum inhalations by using values of peak inspiratory flow rate (PIFR) measured by Clarke et al. (Journal of Aerosol Med, 6(2), p. 99-110, 1993) for the flow rate Q from two inhaler resistances of 0.02 and 0.055 kPa1/2/LPM, with a inhalation volume of 2 L based on both FDA guidance documents for dry powder inhalers and on the work of Tiddens et al. (Journal of Aerosol Med, 19, (4), p. 456-465, 2006) who found adults averaging 2.2 L inhaled volume through a variety of DPIs.

Mild, moderate and severe adult COPD patients are predicted to be able to achieve maximum inhalation energies of 5.1 to 21 Joules, 5.2 to 19 Joules, and 2.3 to 18 Joules respectively. This is again based on using measured PIFR values for the flow rate Q in the equation for inhalation energy. The PIFR achievable for each group is a function of the inhaler resistance that is being inhaled through. The work of Broeders et al. (Eur Respir J, 18, p. 780-'783, 2001)

was used to predict maximum and minimum achievable PIFR through 2 dry powder inhalers of resistances 0.021 and 0.032 kPa1/2/LPM for each.

Similarly, adult asthmatic patients are predicted to be able to achieve maximum inhalation energies of 7.4 to 21 Joules based on the same assumptions as the COPD population and PIFR data from Broeders et al.

Healthy adults and children, COPD patients, asthmatic patients ages 5 and above, and CF patients, for example, are capable of providing sufficient inhalation energy to empty and disperse the dry powder formulations of the invention.

An advantage of aspects of the invention is the production of powders that disperse well across a wide range of flow rates and are relatively flow rate independent. In certain aspects, the dry particles and powders of the invention enable the use of a simple, passive DPI for a wide patient population.

Preferably, the respirable dry particles have a 1 bar/4 bar or 0.5 bar/4 bar of 2 or less, as described herein. For example, a 1 bar/4 bar or 0.5 bar/4 bar of 1.9 or less, 1.8 or less, 1.7 or less, 1.6 or less, 1.5 or less, 1.4 or less, 1.3 or less, 1.2 or less, 1.1 or less or about 1.0. Alternatively or in addition, the respirable dry particles have an MMAD of about 5 microns or less. Alternatively or in addition, the respirable dry particles can have a VMGD between about 0.5 microns and about 5 microns, or a VMGD between about 5 microns and about 20 microns. Alternatively or in addition, the respirable dry particles can have a heat of solution that not is greater than about −10 kcal/mol (e.g., between −10 kcal/mol and 10 kcal/mol or between −7 kcal/mol and 7 kcal/mol).

In preferred aspects, the respirable dry powder comprises respirable dry particles that characterized by:
1. VMGD at 1 bar as measured using a HELOS/RODOS system between 0.5 microns and 10 microns, preferably between 1 microns and 7 microns, between 1 microns and 5 microns, or between 1 microns and 3 microns;
2. 1 bar/4 bar of 1.6 or less, preferably less than 1.5, less than 1.4, less than 1.3, less than 1.2 or less than 1.1; and
3. tap density of about 0.4 g/cm$^3$ to about 1.2 g/cm$^3$, 0.5 g/cm$^3$ to about 1.0 g/cm$^3$, preferably between about 0.6 g/cm$^3$ and about 0.9 g/cm$^3$.

In other preferred aspects, the respirable dry powder comprises respirable dry particles that characterized by:
1. VMGD at 1 bar as measured using a HELOS/RODOS system between 0.5 microns and 10 microns, preferably between 1 microns and 7 microns, between 1 microns and 5 microns, or between 1 microns and 3 microns;
2. 1 bar/4 bar of 1.6 or less, preferably less than 1.5, less than 1.4, less than 1.3, less than 1.2 or less than 1.1; and
3. MMAD between 0.5 and 6.0, between 1.0 and 5.0 or between 1.0 and 3.0.

In other preferred aspects, the respirable dry powder comprises respirable dry particles that are characterized by:
1. VMGD at 1 bar as measured using a HELOS/RODOS system between 0.5 microns and 10 microns, preferably between 1 microns and 7 microns, between 1 microns and 5 microns, or between 1 microns and 3 microns;
2. 1 bar/4 bar of 1.6 or less, preferably less than 1.5, less than 1.4, less than 1.3, less than 1.2 or less than 1.1; and
3. FPF_TD<5.0 μm of at least 30%, at least 40%, at least 50% or at least 60%.

In a further preferred aspect, the respirable dry powder comprises respirable dry particles that characterized by:
1. VMGD at 1 bar as measured using a HELOS/RODOS system between 0.5 microns and 10 microns, preferably between 1 microns and 7 microns, between 1 microns and 5 microns, or between 1 microns and 3 microns;
2. 1 bar/4 bar of 1.6 or less, preferably less than 1.5, less than 1.4, less than 1.3, less than 1.2 or less than 1.1; and
3. Hausner Ratio greater than 1.5, greater than 1.8, or greater than 2.1.

In other preferred aspects, the respirable dry powder comprises respirable dry particles that are characterized by:
1. tap density of about 0.4 g/cm$^3$ to about 1.2 g/cm$^3$, 0.5 g/cm$^3$ to about 1.0 g/cm$^3$, preferably between about 0.6 g/cm$^3$ and about 0.9 g/cm$^3$.
2. FPF_TD<5.0 μm of at least 30%, at least 40%, at least 50% or at least 60%.
3. Hausner Ratio greater than 1.5, greater than 1.8, or greater than 2.1.

The respirable dry particles and dry powders described herein are suitable for inhalation therapies. The respirable dry particles may be fabricated with the appropriate material, surface roughness, diameter, magnetic properties and tap density for localized delivery to selected regions of the respiratory system such as the deep lung or upper or central airways. For example, higher density or larger respirable dry particles may be used for upper airway delivery, or a mixture of varying size respirable dry particles in a sample, provided with the same or a different formulation, may be administered to target different regions of the lung in one administration. In one aspect, the magnetic properties refer to particle to particle charge properties.

Because the respirable dry powders and respirable dry particles described herein contain salts, they may be hygroscopic. Accordingly it is desirable to store or maintain the respirable dry powders and respirable dry particles under conditions to prevent hydration of the powders. For example, if it is desirable to prevent hydration, the relative humidity of the storage environment should be less than 75%, less than 60%, less than 50%, less than 40%, less than 30%, less than 25%, less than 20%, less than 15%, less than 10%, or less than 5% humidity. The respirable dry powders and respirable dry particles can be packaged (e.g., in sealed capsules, blisters, vials) under these conditions.

In preferred embodiments, the respirable dry powders or respirable dry particles of the invention possess aerosol characteristics that permit effective delivery of the respirable dry particles to the respiratory system without the use of propellants.

The dry particles of the invention can be blended with an active ingredient or co-formulated with an active ingredient to maintain characteristic high dispersibility of the dry particles and dry powders of the invention.

Methods for Preparing Dry Powders and Dry Particles

The respirable dry particles and dry powders can be prepared using any suitable method. Many suitable methods for preparing respirable dry powders and particles are conventional in the art, and include single and double emulsion solvent evaporation, spray drying, milling (e.g., jet milling), blending, solvent extraction, solvent evaporation, phase separation, simple and complex coacervation, interfacial polymerization, suitable methods that involve the use of supercritical carbon dioxide ($CO_2$), sonocrystallization, nanoparticle aggregate formation and other suitable methods. Respirable dry particles can be made using methods for making microspheres or microcapsules known in the art. These methods can be employed under conditions that result in the formation of respirable dry particles with desired aerodynamic properties (e.g., aerodynamic diameter and geometric diameter). If desired, respirable dry particles with desired properties, such as size and density, can be selected using suitable methods, such as sieving.

The respirable dry particles are preferably spray dried. Suitable spray-drying techniques are described, for example, by K. Masters in "Spray Drying Handbook", John Wiley & Sons, New York (1984). Generally, during spray-drying, heat from a hot gas such as heated air or nitrogen is used to evaporate a solvent from droplets formed by atomizing a continuous liquid feed. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. For example, a rotary atomizer having a 4- or 24-vaned wheel may be used. Examples of suitable spray dryers that can be outfitted with either a rotary atomizer or a nozzle, include, Mobile Minor Spray Dryer or the Model PSD-1, both manufactured by GEA Group (Niro, Inc.; Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 90° C. to about 300° C., and preferably is about 220° C. to about 285° C. The spray dryer outlet temperature will vary depending upon such factors as the feed temperature and the properties of the materials being dried. Generally, the outlet temperature is about 50° C. to about 150° C., preferably about 90° C. to about 120° C., or about 98° C. to about 108° C.

In another aspect, the inlet temperature to the spray dryer is about 90° C. to about 300° C., and preferably is about 150° C. to about 220° C. The spray dryer outlet temperature will vary depending upon such factors as the feed temperature and the properties of the materials being dried. Generally, the outlet temperature is about 50° C. to about 150° C., preferably about 50° C. to about 90° C.

If desired, the respirable dry particles that are produced can be fractionated by volumetric size, for example, using a sieve, or fractioned by aerodynamic size, for example, using a cyclone, and/or further separated according to density using techniques known to those of skill in the art.

To prepare the respirable dry particles of the invention, generally, a solution, emulsion or suspension that contains the desired components of the dry powder (i.e., a feed stock) is prepared and spray dried under suitable conditions. Preferably, the dissolved or suspended solids concentration in the feed stock is at least about 1 g/L, at least about 2 g/L, at least about 5 g/L, at least about 10 g/L, at least about 15 g/L, at least about 20 g/L, at least about 30 g/L, at least about 40 g/L, at least about 50 g/L, at least about 60 g/L, at least about 70 g/L, at least about 80 g/L, at least about 90 g/L, or at least about 100 g/L. The feed stock can be provided by preparing a single solution or suspension by dissolving or suspending suitable components (e.g., salts, excipients, other active ingredients) in a suitable solvent. The solvent, emulsion or suspension can be prepared using any suitable methods, such as bulk mixing of dry and/or liquid components or static mixing of liquid components to form a combination. For example, a hydrophilic component (e.g., an aqueous solution) and a hydrophobic component (e.g., an organic solution) can be combined using a static mixer to form a combination. The combination can then be atomized to produce droplets, which are dried to form respirable dry particles. Preferably, the atomizing step is performed immediately after the components are combined in the static mixer.

The feed stock, or components of the feed stock, can be prepared using any suitable solvent, such as an organic solvent, an aqueous solvent or mixtures thereof. Suitable organic solvents that can be employed include but are not limited to alcohols such as, for example, ethanol, methanol, propanol, isopropanol, butanols, and others. Other organic solvents include but are not limited to perfluorocarbons, dichloromethane, chloroform, ether, ethyl acetate, methyl tert-butyl ether and others. Co-solvents that can be employed include an aqueous solvent and an organic solvent, such as, but not limited to, the organic solvents as described above. Aqueous solvents include water and buffered solutions.

The feed stock or components of the feed stock can have any desired pH, viscosity or other properties. If desired, a pH buffer can be added to the solvent or co-solvent or to the formed mixture. Generally, the pH of the mixture ranges from about 3 to about 8.

Respirable dry particles and dry powders can be fabricated and then separated, for example, by filtration or centrifugation by means of a cyclone, to provide a particle sample with a preselected size distribution. For example, greater than about 30%, greater than about 40%, greater than about 50%, greater than about 60%, greater than about 70%, greater than about 80%, or greater than about 90% of the respirable dry particles in a sample can have a diameter within a selected range. The selected range within which a certain percentage of the respirable dry particles fall can be, for example, any of the size ranges described herein, such as between about 0.1 to about 3 microns VMGD.

The invention also relates to respirable dry powders or respirable dry particles produced by preparing a feedstock solution, emulsion or suspension and spray drying the feedstock according to the methods described herein. The feedstock can be prepared using (a) e.g., a calcium salt, such as calcium lactate or calcium chloride, or a magnesium salt that provide divalent metal cation in an amount of less than 3% by weight and (b) a sodium salt, such as sodium citrate, sodium chloride or sodium sulfate, in an amount of at least about 1% to 99.9% by weight of the resulting dry particle. If desired, an excipient, such as leucine can be added to the feedstock in an amount of about 0% to 99% by weight of the resulting dry particle, and optionally a pharmaceutically active agent in an amount of about 0.001% to 99% by weight of the resulting dry particle and one or more suitable solvents for dissolution of the solutes and formulations of the feedstock.

Any suitable method can be used for mixing the solutes and solvents to prepare feedstocks (e.g., static mixing, bulk mixing). If desired, additional components that cause or facilitate the mixing can be included in the feedstock. For example, carbon dioxide produces fizzing or effervescence and thus can serve to promote physical mixing of the solute and solvents. Various salts of carbonate or bicarbonate can promote the same effect that carbon dioxide produces and, therefore, can be used in preparation of the feedstocks of the invention.

In an embodiment, the respirable dry powders or respirable dry particles of the invention can be produced through an ion exchange reaction. In certain embodiments of the invention, two saturated or sub-saturated solutions are fed into a static mixer in order to obtain a saturated or supersaturated solution post-static mixing. Preferably, the post-mixed solution is supersaturated. The two solutions may be aqueous or organic, but are preferably substantially aqueous. The post-static mixing solution is then fed into the atomizing unit of a spray dryer. In a preferable embodiment, the post-static mixing solution is immediately fed into the atomizer unit. Some examples of an atomizer unit include a two-fluid nozzle, a rotary atomizer, or a pressure nozzle. Preferably, the atomizer unit is a two-fluid nozzle. In one embodiment, the two-fluid nozzle is an internally mixing nozzle, meaning that the gas impinges on the liquid feed before exiting to most outward orifice. In another embodiment, the two-fluid nozzle is an externally mixing nozzle, meaning that the gas impinges on the liquid feed after exiting the most outward orifice.

The diameter of the respirable dry particles, for example, their VMGD, can be measured using an electrical zone sensing instrument such as a Multisizer IIe, (Coulter Electronic, Luton, Beds, England), or a laser diffraction instrument such as a HELOS system (Sympatec, Princeton, N.J.) or a Mastersizer system (Malvern, Worcestershire, UK). Other instruments for measuring particle geometric diameter are well known in the art. The diameter of respirable dry particles in a sample will range depending upon factors such as particle composition and methods of synthesis. The distribution of size of respirable dry particles in a sample can be selected to permit optimal deposition within targeted sites within the respiratory system.

Experimentally, aerodynamic diameter can be determined using time of flight (TOF) measurements. For example, an instrument such as the Aerosol Particle Sizer (APS) Spectrometer (TSI Inc., Shoreview, MN can be used to measure aerodynamic diameter. The APS measures the time taken for individual respirable dry particles to pass between two fixed laser beams.

Aerodynamic diameter also can be experimentally determined directly using conventional gravitational settling methods, in which the time required for a sample of respirable dry particles to settle a certain distance is measured. Indirect methods for measuring the mass median aerodynamic diameter include the Andersen Cascade Impactor and the multi-stage liquid impinger (MSLI) methods. The methods and instruments for measuring particle aerodynamic diameter are well known in the art.

Tap density is a measure of the envelope mass density characterizing a particle. The envelope mass density of a particle of a statistically isotropic shape is defined as the mass of the particle divided by the minimum sphere envelope volume within which it can be enclosed. Features which can contribute to low tap density include irregular surface texture, high particle cohesiveness and porous structure. Tap density can be measured by using instruments known to those skilled in the art such as the Dual Platform Microprocessor Controlled Tap Density Tester (Vankel, N.C.), a GeoPyc™ instrument (Micrometrics Instrument Corp., Norcross, Ga.), or SOTAX Tap Density Tester model TD2 (SOTAX Corp., Horsham, Pa.). Tap density can be determined using the method of USP Bulk Density and Tapped Density, United States Pharmacopeia convention, Rockville, Md., $10^{th}$ Supplement, 4950-4951, 1999.

Fine particle fraction can be used as one way to characterize the aerosol performance of a dispersed powder. Fine particle fraction describes the size distribution of airborne respirable dry particles. Gravimetric analysis, using a Cascade impactor, is one method of measuring the size distribution, or fine particle fraction, of airborne respirable dry particles. The Andersen Cascade Impactor (ACI) is an eight-stage impactor that can separate aerosols into nine distinct fractions based on aerodynamic size. The size cut-offs of each stage are dependent upon the flow rate at which the ACI is operated. The ACI is made up of multiple stages consisting of a series of nozzles (i.e., a jet plate) and an impaction surface (i.e., an impaction disc). At each stage an aerosol stream passes through the nozzles and impinges upon the surface. Respirable dry particles in the aerosol stream with a large enough inertia will impact upon the plate. Smaller respirable dry particles that do not have enough inertia to impact on the plate will remain in the aerosol stream and be carried to the next stage. Each successive stage of the ACI has a higher aerosol velocity in the nozzles so that smaller respirable dry particles can be collected at each successive stage.

If desired, a two-stage collapsed ACI can also be used to measure fine particle fraction. The two-stage collapsed ACI consists of only the top two stages 0 and 2 of the eight-stage ACI, as well as the final collection filter, and allows for the collection of two separate powder fractions. Specifically, a two-stage collapsed ACI is calibrated so that the fraction of powder that is collected on stage two is composed of respirable dry particles that have an aerodynamic diameter of less than 5.6 microns and greater than 3.4 microns. The fraction of powder passing stage two and depositing on the final collection filter is thus composed of respirable dry particles having an aerodynamic diameter of less than 3.4 microns. The airflow at such a calibration is approximately 60 L/min. The FPF(<5.6) has been demonstrated to correlate to the fraction of the powder that is able to reach the lungs of the patient, while the FPF(<3.4) has been demonstrated to correlate to the fraction of the powder that reaches the deep lung of a patient. These correlations provide a quantitative indicator that can be used for particle optimization.

The FPF(<5.6) has been demonstrated to correlate to the fraction of the powder that is able to make it into the lung of the patient, while the FPF(<3.4) has been demonstrated to correlate to the fraction of the powder that reaches the deep lung of a patient. These correlations provide a quantitative indicator that can be used for particle optimization.

An ACI can be used to approximate the emitted dose, which herein is called gravimetric recovered dose and analytical recovered dose. "Gravimetric recovered dose" is defined as the ratio of the powder weighed on all stage filters of the ACI to the nominal dose. "Analytical recovered dose" is defined as the ratio of the powder recovered from rinsing all stages, all stage filters, and the induction port of the ACI to the nominal dose. The FPF_TD(<5.0) is the ratio of the interpolated amount of powder depositing below 5.0 μm on the ACI to the nominal dose. The FPF_RD(<5.0) is the ratio of the interpolated amount of powder depositing below 5.0 μm on the ACI to either the gravimetric recovered dose or the analytical recovered dose.

Another way to approximate emitted dose is to determine how much powder leaves its container, e.g., capture or blister, upon actuation of a dry powder inhaler (DPI). This takes into account the percentage leaving the capsule, but does not take into account any powder depositing on the DPI. The emitted powder mass is the difference in the weight of the capsule with the dose before inhaler actuation and the weight of the capsule after inhaler actuation. This measurement can also be called the capsule emitted powder mass (CEPM) or sometimes termed "shot-weight".

A Multi-Stage Liquid Impinger (MSLI) is another device that can be used to measure fine particle fraction. The Multi-Stage Liquid Impinger operates on the same principles as the ACI, although instead of eight stages, MSLI has five. Additionally, each MSLI stage consists of an ethanol-wetted glass frit instead of a solid plate. The wetted stage is used to prevent particle bounce and re-entrainment, which can occur when using the ACI.

The geometric particle size distribution can be measured for the respirable dry powder after being emitted from a dry powder inhaler (DPI) by use of a laser diffraction instrument such as the Malvern Spraytec. With the inhaler adapter in the closed-bench configuration, an airtight seal is made to the DPI, causing the outlet aerosol to pass perpendicularly through the laser beam as an internal flow. In this way, known flow rates can be drawn through the DPI by vacuum pressure to empty the DPI. The resulting geometric particle size distribution of the aerosol is measured by the photodetectors with samples typically taken at 1000 Hz for the duration of the inhalation and the DV50, GSD, FPF<5.0 µm measured and averaged over the duration of the inhalation.

The invention also relates to a respirable dry powder or respirable dry particles produced using any of the methods described herein.

The respirable dry particles of the invention can also be characterized by the chemical stability of the salts or the excipients that the respirable dry particles comprise. The chemical stability of the constituent salts can affect important characteristics of the respirable particles including shelf-life, proper storage conditions, acceptable environments for administration, biological compatibility, and effectiveness of the salts. Chemical stability can be assessed using techniques well known in the art. One example of a technique that can be used to assess chemical stability is reverse phase high performance liquid chromatography (RP-HPLC). Respirable dry particles of the invention include salts that are generally stable over a long period of time.

If desired, the respirable dry particles and dry powders described herein can be further processed to increase stability. An important characteristic of pharmaceutical dry powders is whether they are stable at different temperature and humidity conditions. Unstable powders will absorb moisture from the environment and agglomerate, thus altering particle size distribution of the powder.

Excipients, such as maltodextrin, may be used to create more stable particles and powders. For example, maltodextrin may act as an amorphous phase stabilizer and inhibit the components from converting from an amorphous to crystalline state. Alternatively, a post-processing step to help the particles through the crystallization process in a controlled way (e.g., on the baghouse at elevated humidity) can be employed with the resultant powder potentially being further processed to restore their dispersibility if agglomerates formed during the crystallization process, such as by passing the particles through a cyclone to break apart the agglomerates. In an aspect of the example, the baghouse is a product filter. Another possible approach is to optimize around process conditions that lead to manufacturing particles that are more crystalline and therefore more stable. Another approach is to use different excipients, or different levels of current excipients to attempt to manufacture more stable forms of the salts.

Therapeutic Use and Methods

Preferably, the divalent metal cation of the dry powder formulations described herein does not produce prophylactic and/or therapeutic efficacy. Preferably, the prophylactic and/or therapeutic effect is a biological activity selected from anti-bacterial activity, anti-viral activity, anti-inflammatory activity, mucociliary clearance, and combinations thereof. Whether a metal cation, on its own, has such a prophylactic and/or therapeutic effect can be evaluated using one or more in vivo models described herein or well known in the art.

For example, as used herein, a divalent metal cation does not have anti-bacterial activity when it results in less than 50% reduction in colony forming units recovered from the lung in the mouse model of bacterial pneumonia (in vivo pneumonia mouse model). As used herein, a divalent metal cation does not have anti-viral activity when it results in less than 50% reduction in nasal wash viral titer in a ferret model of influenza infection (in vivo influenza ferret model). As used herein, a divalent metal cation does not have anti-inflammatory activity when it results in less than 15% reduction in neutrophils recovered from the lung in the tobacco smoke mouse model of COPD (in vivo pneumonia mouse model). As used herein, a divalent metal cation does not have mucociliary clearance (MCC) activity when a formulation administered to a sheep results in less than 12% of mucus at the one hour point in comparison to baseline measurements. The models and tests are run substantially as described herein or known in the art.

In Vivo Pneumonia Mouse Model

*S. pneumoniae* can be prepared by growing cultures on tryptic soy agar (TSA) blood plates overnight at 37° C. plus 5% CO2. Single colonies are resuspended to an OD600~0.3 in sterile PBS and subsequently diluted 1:4 in sterile PBS (~2×107 Colony forming units (CFU)/mL). Mice can be infected with 50 μL of bacterial suspension (~1×106 CFU) by intratracheal instillation while under anesthesia. Mice (e.g., C57BL6) may be exposed to aerosolized liquid formulations in a whole-body exposure system e.g., using either a high output nebulizer or Pari LC Sprint nebulizer connected to a pie chamber cage that individually holds up to 11 animals. Mice can be treated with dry powder formulations described herein before infection with *S. pneumoniae*. As a control, animals may be exposed to a similar amount of placebo (e.g., 100% leucine powder). Twenty-four hours after infection mice are euthanized e.g., by pentobarbital injection and lungs are collected and homogenized in sterile PBS. Lung homogenate samples are serially diluted in sterile PBS and plated on TSA blood agar plates. CFU are enumerated the following day.

In Vivo COPD Mouse Model

Chronic obstructive pulmonary disease (COPD) is a progressive disease associated with impaired pulmonary function and it primarily occurs as a result of cigarette smoking COPD subjects are further susceptible to exacerbations that are often associated with an infectious agent and acute inflammation. These exacerbations lead to further decline in lung function, which in turn drives the increased frequency and severity of subsequent exacerbations. Animal models for COPD have been developed, e.g., a model of tobacco smoke (TS) exposure leading to acute airway inflammation. (Churg, A. et al. Am J Physiol Lung Cell Mol Physiol 294(4):L612-631, 2008; Churg, A. and J. L. Wright, Proc Am Thorac Soc 6(6):550-552, 2009; Fox, J. C. and Fitzgerald M. R., Curr Opin Pharmacol 9(3):231-242, 2009). The inflammation characteristic of the model is marked by increases in macrophages and neutrophils, with modest increases observed in lymphocytes and epithelial cells.

For example, a 4-day TS exposure model may be employed as shown in Schematic 1.

Schematic 1. TS exposure model protocol.

```
                TS exposure
                 45'/day          BAL
                  ↓  ↓  ↓  ↓       ↓
              ┌───┼──┼──┼──┼───────
              │   ↑  ↑  ↑  ↑
Study day     0   1  2  3  4

Formulation
                      BID
```

Mice (e.g., C57BL6/J) are exposed to TS for up to 45 minutes per day on four successive days by whole body exposure. On each day of TS exposure, mice may be treated with dry powder formulations described herein 1 hour before and 6 hours after TS exposure or with placebo control (e.g., 100% leucine). Dosing may be performed using a whole body exposure system and a capsule based delivery system. A p38 MAP kinase inhibitor ADS110836 may be used as a reference agent (positive control) (see, PCT Publ. No. WO2009/098612) that can be administered by an intra-nasal route. Animals may be euthanized by intra-peritoneal barbiturate anaesthetic overdose 24 hours after the final exposure to either air (sham) or TS on day 5. A bronchoalveolar lavage (BAL) can be performed using 0.4 mL of phosphate buffered saline (PBS). Cells recovered from the BAL are enumerated and differential cell counts carried out using cytospin prepared slides. Inflammatory cell counts in the BAL fluid of animals exposed to TS for 4 days are determined. Dosing may be calculated by collecting samples from the pie cage system onto a glass fiber filter at 1 LPM. The aerosol collected onto the filter is recovered and the cation concentration is determined by HPLC to determine the aerosol concentration of cation (Ec). The estimated dose level (DL) is given by the equation: $DL=Ec \cdot RMV \cdot T/BW$, where RMV is the respiratory minute volume of the animal (0.21 LPM), T is the exposure time, and BW is the body weight of the animal in kg. The resulting estimated dose is then adjusted for the respirable fraction of the aerosol, which is determined based on the fine particle fraction (FPF; % mass less than 5.6 µm).

In Vivo Influenza Ferret Model

Ferrets infected with influenza typically show increases in body temperature within 2 days of infection, drop body weight over the course of the study and show clinical signs of infection such as lethargy and sneezing. These changes coincide with an increase in influenza viral titers shed from the nasal cavity and increases in nasal inflammation. Dry powder formulations described herein and placebo control powders are aerosolized, e.g., using a Palas Rotating Brush Generator 1000 solid particle disperser (RBG, Palas GmbH, Karlsruhe, Germany). Ferrets are exposed to the dry powder formulations described herein and the severity of infection is evaluated over time. Each formulation may be dispersed in a nose-only exposure system 1 hour before infection, 4 hours after infection and then BID for 4 days (d1-4). The study may be terminated on day 10. Body temperatures are determined, e.g., twice a day, beginning on day 0 of the study. On study day −4, ferrets can be implanted with a microchip subcutaneously, e.g., in the right rear flank and another in the shoulder for redundancy. The transponder chip (e.g., IPTT-300 Implantable Programmable Temperature and Identification Transponder; Bio Medic Data Systems, Inc, Seaford, Delaware 19973) allows for ferret identification and provides subcutaneous body temperature data throughout the study using e.g., a BMDS electronic proximity reader wand (WRS-6007; Biomedic Data Systems Inc, Seaford, Delaware). Subcutaneous body temperatures taken on day −3 to −1 are used as baseline temperatures and used to calculate the change from baseline for each animal over the course of the study.

In Vivo Mucociliary Clearance (MCC) Sheep Model

Mucociliary clearance (MCC) can be evaluated in healthy sheep by measurement of the clearance of pulmonary Tc99m-labeled sulfur colloid aerosols that is delivered by inhalation. Immediately following the exposure to the test-formulation (the formulation that is tested for activity), the radio-labeled sulfur colloid aerosol is delivered to the sheep via the same aerosol delivery system and MCC is determined via the collection of serial images. The sheep mucociliary clearance model is a well established model with vehicle clearance typically measuring approximately 5-10% at 60 minutes after delivery of the radioactive aerosol (see, for example, Coote et al., 2009, JEPT 329:769-774). It is known in the art that average clearance measurements greater than about 10% at 60 minutes post baseline indicate enhanced clearance in the model.

For example, a Pari LC jet nebulizer exposure system may be used to deliver the test-formulation. The nebulizer is connected to a dosimeter system consisting of a solenoid valve and a source of compressed air (20 psi). The output of the nebulizer is connected to a T-piece, with one end attached to a respirator (Harvard Apparatus Inc., Holliston, Mass.). The system is activated for 1 second at the onset of the inspiratory cycle of the respirator, which is set at an inspiratory/expiratory ratio of 1:1 and a rate of 20 breaths/minute. A tidal volume of 300 ml is used to deliver the nebulized formulation. The nebulizer was filled with the test-formulation and run to dryness. Alternatively, the test-formulation can be delivered with a rotating brush generator (RBG1000, Palas) instead of the nebulizer to generate the dry powder aerosol. Aerosolized technetium labeled sulfur colloid (99 mTC-SC) is delivered immediately after the test-formulation. Animals are conscious, supported in a mobile restraint, intubated with a cuffed endotracheal tube and maintained conscious for the duration of the study.

After 99m TC-SC nebulization, the animals are immediately extubated and positioned in their natural upright position underneath a gamma camera (Dyna Cam, Picker Corp., Nothford, Conn.) so that the field of image is perpendicular to the animals' spinal cord. After acquisition of a baseline image, serial images are obtained at 5 min intervals for the first hour. All images are obtained and stored in the computer for analysis. An area of interest is traced over the image corresponding to the right lung of the animals, and counts are recorded. The left lung is excluded from analysis because its corresponding image is superimposed over the stomach and counts could be affected by swallowed radio-labeled mucus. The counts are corrected for decay and clearance expressed as the percentage reduction of radioactivity present from the baseline image.

The dose delivered for test-formulations is measured in-vitro with a breathing simulator system drawing the inspiratory flow through filter samples collected at the distal end of a tracheal tube. For example, 10 filter samples of 1.5 minutes each are assayed for deposited divalent metal cation by HPLC and the average rate of divalent metal cation deposition was determined. From this the dose delivered in 15 minutes to a 50 kg sheep is calculated. These measured doses correspond to the dose delivered from the distal end of the tracheal tube to the sheep during treatment.

The respirable dry powders and respirable dry particles of the present invention are for administration to the respiratory tract. Administration to the respiratory tract can be for local activity of the delivered pharmaceutically active agent or for systemic activity. For example, the respirable dry powders can be administered to the nasal cavity or upper airway to provide, for example, anti-inflammatory, anti-viral, or anti-bacterial activity to the nasal cavity or upper airway. The respirable dry powders can be administered to the deep lung to provide local activity in the lung or for absorption into the systemic circulation. Systemic delivery of certain pharmaceutically active agents via the lung is particularly advantageous for agents that undergo substantial first pass metabolism (e.g., in the liver) following oral administration.

The respirable dry powders and respirable dry particles of the present invention may also be administered to the buccal cavity. Administration to the buccal cavity can be for local activity of the delivered pharmaceutically active agent or for systemic activity. For exaple, the respirable dry powders can be administered to the buccal cavity to provide, for example, anti-inflammatory, anti-viral, or anti-bacterial activity to the buccal cavity.

The dry powders and dry particles of the invention can be administered to a subject in need thereof for systemic delivery of a pharmaceutically active agent, such as to treat an infectious disease or metabolic disease.

The dry powders and dry particles of the invention can be administered to a subject in need thereof for the treatment of respiratory (e.g., pulmonary) diseases, such as respiratory syncytial virus infection, idiopathic fibrosis, alpha-1 antitrypsin deficiency, asthma, airway hyperresponsiveness, seasonal allergic allergy, brochiectasis, chronic bronchitis, emphysema, chronic obstructive pulmonary disease, cystic fibrosis and the like, and for the treatment and/or prevention of acute exacerbations of these chronic diseases, such as exacerbations caused by viral infections (e.g., influenza virus, parainfluenza virus, respiratory syncytial virus, rhinovirus, adenovirus, metapneumovirus, coxsackie virus, echo virus, corona virus, herpes virus, cytomegalovirus, and the like), bacterial infections (e.g., *Streptococcus pneumoniae*, which is commonly referred to as pneumococcus, *Staphylococcus aureus, Burkholderis* ssp., *Streptococcus agalactiae, Haemophilus influenzae, Haemophilus parainfluenzae, Klebsiella pneumoniae, Escherichia coli, Pseudomonas aeruginosa, Moraxella catarrhalis, Chlamydophila pneumoniae, Mycoplasma pneumoniae, Legionella pneumophila, Serratia marcescens, Mycobacterium tuberculosis, Bordetella pertussis*, and the like), fungal infections (e.g., *Histoplasma capsulatum, Cryptococcus neoformans, Pneumocystis jiroveci, Coccidioides immitis*, and the like) or parasitic infections (e.g., *Toxoplasma gondii, Strongyloides stercoralis*, and the like), or environmental allergens and irritants (e.g., aeroallergens, including pollen and cat dander, airborne particulates, and the like).

The dry powders and dry particles of the invention can be administered to a subject in need thereof for the treatment and/or prevention and/or reducing contagion of infectious diseases of the respiratory tract, such as pneumonia (including community-acquired pneumonia, nosocomial pneumonia (hospital-acquired pneumonia, HAP; health-care associated pneumonia, HCAP), ventilator-associated pneumonia (VAP)), ventilator-associated tracheobronchitis (VAT), bronchitis, croup (e.g., postintubation croup, and infectious croup), tuberculosis, influenza, common cold, and viral infections (e.g., influenza virus, parainfluenza virus, respiratory syncytial virus, rhinovirus, adenovirus, metapneumovirus, coxsackie virus, echo virus, corona virus, herpes virus, cytomegalovirus, and the like), bacterial infections (e.g., *Streptococcus pneumoniae*, which is commonly referred to as pneumococcus, *Staphylococcus aureus, Streptococcus agalactiae, Haemophilus influenzae, Haemophilus parainfluenzae, Klebsiella pneumoniae, Escherichia coli, Pseudomonas aeruginosa, Moraxella catarrhalis, Chlamydophila pneumoniae, Mycoplasma pneumoniae, Legionella pneumophila, Serratia marcescens, Mycobacterium tuberculosis, Bordetella pertussis*, and the like), fungal infections (e.g., *Histoplasma capsulatum, Cryptococcus neoformans, Pneumocystis jiroveci, Coccidioides immitis*, and the like) or parasitic infections (e.g., *Toxoplasma gondii, Strongyloides stercoralis*, and the like), or environmental allergens and irritants (e.g., aeroallergens, airborne particulates, and the like).

In some aspects, the invention provides a method for treating a pulmonary disease, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of respirable dry particles or dry powder, as described herein.

In other aspects, the invention provides a method for the treatment or prevention of acute exacerbations of a chronic pulmonary disease, such as asthma, airway hyperresponsiveness, seasonal allergic allergy, bronchiectasis, chronic bronchitis, emphysema, chronic obstructive pulmonary disease, cystic fibrosis and the like, comprising administering to the respiratory tract of a subject in need thereof an effective amount of respirable dry particles or dry powder, as described herein.

In other aspects, the invention provides a method for treating, preventing and/or reducing contagion of an infectious disease of the respiratory tract, comprising administering to the respiratory tract of a subject in need thereof an effective amount of respirable dry particles or dry powder, as described herein.

In some aspects, the invention provides a method for the treatment or prevention of cardiovascular disease, autoimmune disorders, transplant rejections, autoimmune disorders, allergy-related asthma, infections, and cancer. For example, the invention provides a method for the treatment or prevention of postmenopausal osteoporosis, cryopyrin-associated periodic syndromes (CAPS), paroxysmal nocturnal hemoglobinuria, psoriasis, rheumatoid arthritis, psoriatic arthritis, ankylosing spondylitis, multiple sclerosis, and macular degeneration. For example, dry powders or dry particles of the invention are co-formulated or blended with therapeutic antibodies as described herein. The co-formulated or blended dry powders may then be administered to a subject in need of therapy or prevention.

In certain aspects, the invention provides a method for the treatment or prevention of cancer such as acute myeloid leukemia, B cell leukemia, non-Hodgkin's lymphoma, breast cancer (e.g., with HER2/neu overexpression), glioma, squamous cell carcinomas, colorectal carcinoma, anaplastic large cell lymphoma (ALCL), Hodgkin lymphoma, head and neck cancer, acute myelogenous leukemia (AML), melanoma, and chronic lymphocytic leukemia (CLL). Alternatively or in addition, the invention provides a method for the treatment or prevention of cancer by anti-angiogenic cancer therapy. For example, dry powders or dry particles of the invention are co-formulated or blended with therapeutic antibodies as described herein. Therapeutic antibodies can be cancer-specific antibodies, such as a humanized monoclonal antibody, e.g., gemtuzumab, alemtuzumab, trastuzumab, nimotuzumab, bevacizumab, or a chimeric monoclonal antibody, e.g., rituximab and cetuximab. The co-formulated or blended dry powders may then be administered to a subject in need of therapy or prevention.

In certain aspects, the invention provides a method for the treatment or prevention of inflammation such as rheumatoid arthritis, Crohn's disease, ulcerative Colitis, acute rejection of kidney transplants, moderate-to-severe allergic asthma. For example, dry powders or dry particles of the invention are co-formulated or blended with therapeutic antibodies as described herein. Therapeutic antibodies can be inflammation-specific antibodies, such as chimeric monoclonal antibodies, e.g., infliximab, basiliximab, humanized monoclonal antibodies, e.g., daclizumab, omalizumab, or human antibodies, e.g., adalimumab. The co-formulated or blended dry powders may then be administered to a subject in need of therapy or prevention.

In certain aspects, the invention provides a method for the treatment or prevention of RSV infections in children. For example, dry powders or dry particles of the invention are co-formulated or blended with therapeutic antibodies as described herein. Therapeutic antibodies can be RSV infection-specific antibodies, such as the humanized monoclonal antibody palivizumab which inhibits an RSV fusion (F) protein. The co-formulated or blended dry powders may then be administered to a subject in need of RSV infection therapy or prevention.

In certain aspects, the invention provides a method for the treatment or prevention of diabetes. For example, dry powders or dry particles of the invention are co-formulated or blended with insulin as described herein. The co-formulated or blended dry powders may then be administered to a subject in need of insulin therapy or prevention.

The respirable dry particles and dry powders can be administered to the respiratory tract of a subject in need thereof using any suitable method, such as instillation techniques, and/or an inhalation device, such as a dry powder inhaler (DPI) or metered dose inhaler (MDI). A number of DPIs are available, such as, the inhalers disclosed is U.S. Pat. Nos. 4,995,385 and 4,069,819, Spinhaler® (Fisons, Loughborough, U.K.), Rotahalers®, Diskhaler® and Diskus® (GlaxoSmithKline, Research Triangle Technology Park, North Carolina), FlowCapss® (Hovione, Loures, Portugal), Inhalators® (Boehringer-Ingelheim, Germany), Aerolizer® (Novartis, Switzerland), RS-01 (Plastiape, Italy) and others known to those skilled in the art.

Generally, inhalation devices (e.g., DPIs) are able to deliver a maximum amount of dry powder or dry particles in a single inhalation, which is related to the capacity of the blisters, capsules (e.g., size 000, 00, 0E, 0, 1, 2, 3, and 4, with respective volumetric capacities of 1.37 ml, 950 µl, 770 µl, 680 µl, 480 µl, 360 µl, 270 µl, and 200 µl) or other means that contain the dry particles or dry powders within the inhaler. Accordingly, delivery of a desired dose or effective amount may require two or more inhalations. Preferably, each dose that is administered to a subject in need thereof contains an effective amount of respirable dry particles or dry powder and is administered using no more than about 4 inhalations. For example, each dose of respirable dry particles or dry powder can be administered in a single inhalation or 2, 3, or 4 inhalations. The respirable dry particles and dry powders are preferably administered in a single, breath-activated step using a breath-activated DPI. When this type of device is used, the energy of the subject's inhalation both disperses the respirable dry particles and draws them into the respiratory tract.

The respirable dry particles or dry powders can be delivered by inhalation to a desired area within the respiratory tract, as desired. It is well-known that particles with an aerodynamic diameter of about 1 micron to about 3 microns, can be delivered to the deep lung. Larger aerodynamic diameters, for example, from about 3 microns to about 5 microns can be delivered to the central and upper airways.

For dry powder inhalers, oral cavity deposition is dominated by inertial impaction and so characterized by the aerosol's Stokes number (DeHaan et al. Journal of Aerosol Science, 35 (3), 309-331, 2003). For equivalent inhaler geometry, breathing pattern and oral cavity geometry, the Stokes number, and so the oral cavity deposition, is primarily affected by the aerodynamic size of the inhaled powder. Hence, factors which contribute to oral deposition of a powder include the size distribution of the individual particles and the dispersibility of the powder. If the MMAD of the individual particles is too large, e.g., above 5 µm, then an increasing percentage of powder will deposit in the oral cavity. Likewise, if a powder has poor dispersibility, it is an indication that the particles will leave the dry powder inhaler and enter the oral cavity as agglomerates. Agglomerated powder will perform aerodynamically like an individual particle as large as the agglomerate, therefore even if the individual particles are small (e.g., MMAD of 5 microns or less), the size distribution of the inhaled powder may have an MMAD of greater than 5 µm, leading to enhanced oral cavity deposition.

Therefore, it is desirable to have a powder in which the particles are small (e.g., MMAD of 5 microns or less, e.g., between 1 to 5 microns), and are highly dispersible (e.g., 1/4 bar or alternatively, 0.5/4 bar of 2.0, and preferably less than 1.5). More preferably, the respirable dry powder is comprised of respirable dry particles with an MMAD between 1 to 4 microns or 1 to 3 microns, and have a 1/4 bar less than 1.4, or less than 1.3, and more preferably less than 1.2.

The absolute geometric diameter of the particles measured at 1 bar using the HELOS system is not critical provided that the particle's envelope density is sufficient such that the MMAD is in one of the ranges listed above, wherein MMAD is VMGD times the square root of the envelope density (MMAD=VMGD*sqrt(envelope density)). If it is desired to deliver a high unit dose of salt using a fixed volume dosing container, then, particles of higher envelop density are desired. High envelope density allows for more mass of powder to be contained within the fixed volume dosing container. Preferable envelope densities are greater than 0.1 g/cc, greater than 0.25 g/cc, greater than 0.4 g/cc, greater than 0.5 g/cc, and greater than 0.6 g/cc.

The respirable dry powders and particles of the invention can be employed in compositions suitable for drug delivery via the respiratory system. For example, such compositions can include blends of the respirable dry particles of the invention and one or more other dry particles or powders, such as dry particles or powders that contain an active agent, or that consist of or consist essentially of one or more pharmaceutically acceptable excipients.

Respirable dry powders and dry particles suitable for use in the methods of the invention can travel through the upper airways (i.e., the oropharynx and larynx), the lower airways, which include the trachea followed by bifurcations into the bronchi and bronchioli, and through the terminal bronchioli which in turn divide into respiratory bronchioli leading then to the ultimate respiratory zone, the alveoli or the deep lung. In one embodiment of the invention, most of the mass of respirable dry powders or particles deposit in the deep lung. In another embodiment of the invention, delivery is primarily to the central airways. In another embodiment, delivery is to the upper airways.

The respirable dry particles or dry powders of the invention can be delivered by inhalation at various parts of the breathing cycle (e.g., laminar flow at mid-breath). An advantage of the high dispersibility of the dry powders and dry particles of the invention is the ability to target deposition in the respiratory tract. For example, breath controlled delivery of nebulized solutions is a recent development in liquid aerosol delivery (Dalby et al. in Inhalation Aerosols, edited by Hickey 2007, p. 437). In this case, nebulized droplets are released only during certain portions of the breathing cycle. For deep lung delivery, droplets are released in the beginning of the inhalation cycle, while for central airway deposition, they they are released later in the inhalation.

The highly dispersible powders of the invention can provide advantages for targeting the timing of drug delivery in the breathing cycle and also location in the human lung. Because the respirable dry powders of the invention can be dispersed rapidly, such as within a fraction of a typical inhalation maneuver, the timing of the powder dispersal can be controlled to deliver an aerosol at specific times within the inhalation.

With a highly dispersible powder, the complete dose of aerosol can be dispersed at the beginning portion of the inhalation. While the patient's inhalation flow rate ramps up to the peak inspiratory flow rate, a highly dispersible powder will begin to disperse already at the beginning of the ramp up and could completely disperse a dose in the first portion of the inhalation. Since the air that is inhaled at the beginning of the inhalation will ventilate deepest into the lungs, dispersing the most aerosol into the first part of the inhalation is preferable for deep lung deposition. Similarly, for central deposition, dispersing the aerosol at a high concentration into the air which will ventilate the central airways can be achieved by rapid dispersion of the dose near the mid to end of the inhalation. This can be accomplished by a number of mechanical and other means such as a switch operated by time, pressure or flow rate which diverts the patient's inhaled air to the powder to be dispersed only after the switch conditions are met.

Aerosol dosage, formulations and delivery systems may be selected for a particular therapeutic application, as described, for example, in Gonda, I. "Aerosols for delivery of therapeutic and diagnostic agents to the respiratory tract," in Critical Reviews in Therapeutic Drug Carrier Systems, 6: 273-313 (1990); and in Moren, "Aerosol Dosage Forms and Formulations," in Aerosols in Medicine, Principles, Diagnosis and Therapy, Moren, et al., Eds., Esevier, Amsterdam (1985).

Suitable dosing to provide the desired therapeutic effect can be determined by a clinician based on the severity of the condition (e.g., infection), overall well being of the subject and the subject's tolerance to respirable dry particles and dry powders and other considerations. Based on these and other considerations, a clinician can determine appropriate doses and intervals between doses. Generally, respirable dry particles and dry powders are administered once, twice or three times a day, as needed.

If desired or indicated, the respirable dry particles and dry powders described herein can be administered with one or more other therapeutic agents. The other therapeutic agents can be administered by any suitable route, such as orally, parenterally (e.g., intravenous, intraarterial, intramuscular, or subcutaneous injection), topically, by inhalation (e.g., intrabronchial, intranasal or oral inhalation, intranasal drops), rectally, vaginally, and the like. The respirable dry particles and dry powders can be administered before, substantially concurrently with, or subsequent to administration of the other therapeutic agent. Preferably, the respirable dry particles and dry powders and the other therapeutic agent are administered so as to provide substantial overlap of their pharmacologic activities.

Another advantage provided by the respirable dry powders and respirable dry particles described herein, is that dosing efficiency can be increased as a result of hygroscopic growth of particles inside the lungs, due to particle moisture growth. The propensity of the partially amorphous compositions of the invention to take up water at elevated humidities can also be advantageous with respect to their deposition profiles in vivo. Due to their rapid water uptake at high humidities, these powder formulations can undergo hygroscopic growth due to the absorbance of water from the humid air in the respiratory tract as they transit into the lungs. This can result in an increase in their effective aerodynamic diameters during transit into the lungs, which will further facilitate their deposition in the airways.

EXEMPLIFICATION

Methods:

Geometric or Volume Diameter. Volume median diameter ($\times 50$), which may also be referred to as volume median geometric diameter (VMGD), was determined using a laser diffraction technique. The equipment consisted of a HELOS diffractometer and a RODOS dry powder disperser (Sympatec, Inc., Princeton, N.J.). The RODOS disperser applies a shear force to a sample of particles, controlled by the regulator pressure (typically set at 1.0 bar with maximum orifice ring pressure) of the incoming compressed dry air. The pressure settings may be varied to vary the amount of energy used to disperse the powder. For example, the regulator pressure may be varied from 0.2 bar to 4.0 bar. Powder sample is dispensed from a microspatula into the RODOS funnel. The dispersed particles travel through a laser beam where the resulting diffracted light pattern produced is collected, typically using an R1 lens, by a series of detectors. The ensemble diffraction pattern is then translated into a volume-based particle size distribution using the Fraunhofer diffraction model, on the basis that smaller particles diffract light at larger angles. Using this method geometric standard deviation (GSD) for the volume mean geometric diameter was also determined.

Fine Particle Fraction. The aerodynamic properties of the powders dispersed from an inhaler device were assessed with a Mk-II 1 ACFM Andersen Cascade Impactor (Copley Scientific Limited, Nottingham, UK). The instrument was run in controlled environmental conditions of 18 to 25° C. and relative humidity (RH) between 25 and 35%. The instrument consists of eight stages that separate aerosol particles based on inertial impaction. At each stage, the aerosol stream passes through a set of nozzles and impinges on a corresponding impaction plate. Particles having small enough inertia will continue with the aerosol stream to the next stage, while the remaining particles will impact upon the plate. At each successive stage, the aerosol passes through nozzles at a higher velocity and aerodynamically smaller particles are collected on the plate. After the aerosol passes through the final stage, a filter collects the smallest particles that remain. Gravimetric or analytic analysis can then be performed to determine the particle size distribution.

The impaction technique utilized allowed for the collection of eight separate powder fractions. The capsules (Capsugel, Greenwood, S.C.) were half-filled with approximately 20 or 50 mg powder and placed in a hand-held, breath-activated dry powder inhaler (DPI) device, the high resistance RS-01 DPI (Plastiape, Osnago, Italy). In some instances, the capsules were filled as much as necessary to fit the desired mass of powder into the capsule. The capsule was punctured and the powder was drawn through the cascade impactor operated at a flow rate of 60.0 L/min for 2.0 s. At this flow rate, the calibrated cut-off diameters for the eight stages are 8.6, 6.5, 4.4, 3.3, 2.0, 1.1, 0.5 and 0.3 microns. The fractions were collected by placing filters in the apparatus and determining the amount of powder that impinged on them by gravimetric measurements. The fine particle fraction of the total dose of powder (FPF_TD) less than or equal to an effective cut-off aerodynamic diameter was calculated by dividing the powder mass recovered from the desired stages of the impactor by the total particle mass in the capsule. Results are reported as the fine particle fraction of less than 4.4 microns (FPF<4.4 microns), as well as mass median aerodynamic diameter (MMAD) and GSD calculated from the FPF trend across stages. The fine particle fraction can alternatively be calculated relative to the recovered or emitted dose of powder by dividing the powder mass recovered from the desired stages of the impactor by the total powder mass recovered.

Tap Density. Tap density was measured using a modified method requiring smaller powder quantities, following USP <616> with the substitution of a 1.5 cc microcentrifuge tube (Eppendorf AG, Hamburg, Germany) or a 0.3 cc section of a disposable serological polystyrene micropipette (Grenier Bio-One, Monroe, N.C.) with polyethylene caps (Kimble Chase, Vineland, N.J.) to cap both ends and hold the powder. Instruments for measuring tap density, known to those skilled in the art, include but are not limited to the Dual Platform Microprocessor Controlled Tap Density Tester (Vankel, Cary, N.C.) or a SOTAX Tap Density Tester model TD2 (Horsham, Pa.). Tap density is a standard measure of the envelope mass density. The envelope mass density of an isotropic particle is defined as the mass of the particle divided by the minimum spherical envelope volume within which it can be enclosed.

Bulk Density. Bulk density was estimated prior to tap density measurement by dividing the weight of the powder by the volume of the powder, as estimated using the volumetric measuring device.

Example 1

Production and Characterication of Divalent Cationic Powders

Several powders of the invention were produced by spray drying homogenous particles. The composition of these powders is shown in Table 1.

TABLE 1

Composition of divalent cation dry powders.

| Form | Salt | % Salt load (w/w) | Excipient | % Excipient load (w/w) | Additional component (e.g., drug, $2^{nd}$ salt) | % Additional component load (w/w) |
|---|---|---|---|---|---|---|
| I | Magnesium sulfate | 5 | N/A | 0 | albuterol | 95 |
| II | Calcium sulfate | 7 | Maltodextrin | 43 | ciprofloxacin | 50 |
| III | Magnesium sulfate | 15 | Maltodextrin | 35 | tobramycin | 50 |
| IV | Calcium sulfate | 40 | Maltodextrin | 10 | ciprofloxacin | 50 |
| V | Magnesium lactate | 58.3 | Leucine | 37.5 | Sodium chloride | 4.2 |
| VI | Magnesium lactate | 9 | Maltodextrin | 90.9 | Tiotropium bromide (TioB) | .113 |
| VII | Magnesium lactate | 10 | Mannitol | 90 | N/A | N/A |
| VIII | Magnesium lactate | 10 | Maltodextrin | 90 | N/A | N/A |
| IX | Magnesium sulfate | 10 | Leucine | 90 | N/A | N/A |
| X | Magnesium lactate | 10 | Leucine | 90 | N/A | N/A |

Materials used in the following Examples and their sources are listed below. Calcium sulfate dihydrate, magnesium lactate, magnesium sulfate, sodium chloride, L-leucine, maltodextrin, albuterol sulfate, ciprofloxacin hydrochloride and tobramycin were obtained from Sigma-Aldrich Co. (St. Louis, MO.) or Spectrum Chemicals (Gardena, CA.). Ultrapure water was from a water purification system (Millipore Corp., Billerica, MA.).

Spray drying homogenous particles requires that the ingredients of interest be solubilized in solution or suspended in a uniform and stable suspension. Most of the materials mentioned above are sufficiently water-soluble to prepare suitable spray drying solutions (see Table 2). However, calcium sulfate dihydrate has a low solubility in water. As a result of this low solubility, formulation feedstock development work was necessary to prepare solutions or suspensions that could be spray dried. These solutions or suspensions included combinations of salts and antibiotic, steroid or beta agonist in an appropriate solvent, typically water.

TABLE 2

Mono- and divalent cation salt solubilities

| Salt | Water solubility at 20-30° C., 1 bar |
|---|---|
| Magnesium carbonate | 4.5 in 100 parts[2] |
| Magnesium carbonate hydroxide | Soluble in 3300 parts of $CO_2$ free water[1] |
| Magnesium chloride | Hexahydrate, 1 g/0.6 mL[1] |
| Magnesium citrate | Partially soluble in cold water[3] |
| Magnesium sulfate | Heptahydrate, 71 g/100 mL[1] |
| Potassium chloride | 1 g/2.8 mL[1] |
| Potassium citrate | Monohydrate, 1 g/0.65 mL[1] |
| Sodium ascorbate | 62 g/100 mL[1] |
| Sodium bicarbonate | Soluble in 10 parts[1] |
| Sodium carbonate | Soluble in 3.5 parts[1] |
| Sodium chloride | 1 g/2.8 mL[1] |
| Sodium citrate | Dihydrate, soluble in 1.3 parts[1] |
| Sodium lactate | Commercially available as 70-80% in water[1] |
| Dibasic sodium phosphate | Soluble in ~8 parts[1] |
| Sodium propionate | 1 g/~1 mL[1] |
| Sodium sulfate | Soluble in 3.6 parts[1] |

[1]O'Neil, Maryadele J. *The Merck Index: an Encyclopedia of Chemicals, Drugs, and Biologicals.* 14th ed. Whitehouse Station, N.J.: Merck, 2006.

For the spray drying process, the salts, excipients and other drugs were dissolved or suspended in a solvent (e.g., water). The solids concentration (w/v) was chosen dependent on the solubility of the different components. For the calcium sulfate formulation, a concentration of 4 mg/mL was appropriate, given the limited solubility of calcium sulfate: 2 mg/mL. In addition, when preparing spray drying solutions, the water weight of the hydrated starting material must be accounted for. The ratios used for formulations were based on the molecular weight of the anhydrous salts. For calcium sulfate, the dihydrate form is more readily available than the anhydrous form. This required an adjustment in the ratios originally calculated, using a multiplier to correlate the molecular weight of the anhydrous salt with the molecular weight of the hydrate. For example, the molecular weight of anhydrous calcium sulfate is 136.14 g/mol and the dihydrate molecular weight is 172.172 g/mol, so a multiplier of 1.26 will be used to calculate the amount of calcium sulfate dihydrate weighed. For a 5 g total solids concentration where 40% is calcium sulfate, the anhydrous weighed amount of calcium sulfate would be 2 g; instead using the multiplier, a weighed amount of 2.529 g was targeted.

Dry powders were prepared by spray drying on a Büchi B-290 Mini Spray Dryer (BüUCHI Labortechnik AG, Flawil, Switzerland) with powder collection from either a standard or High Performance cyclone. The system used the Büchi B-296 dehumidifier to ensure stable temperature and humidity of the air used to spray dry. Furthermore, when the relative humidity in the room exceeded 30% RH, an external LG dehumidifier (model 49007903, LG Electronics, Englewood Cliffs, N.J.) was run constantly. Atomization of the liquid feed utilized a Büchi two-fluid nozzle with a 1.5 mm diameter. Inlet temperature of the process gas can range from 100° C. to 220° C. and outlet temperature from 80° C. to 120° C. with a liquid feedstock flowrate of 3 mL/min to 10 mL/min. Outlet temperatures can range from 50° C. to 80° C. The two-fluid atomizing gas ranges from 25 mm to 45 mm (355 LPH to 831 LPH) and the aspirator rate ranges from 70% to 100% (28 $m^3$/hr to 38 $m^3$/hr).

The feedstock was prepared as a batch by dissolving the specific salt in ultrapure water, then the excipient, and finally the drug component. The solution was kept agitated throughout the process until the materials were completely dissolved in the water at room temperature.

Formulation I dry powders were produced by spray drying on the Büchi B-290 Mini Spray Dryer (BÜCHI Labortechnik AG, Flawil, Switzerland) with powder collection on a 60 mL glass vessel from a High Performance cyclone. The system used the Büchi B-296 dehumidifier and an external LG dehumidifier (model 49007903, LG Electronics, Englewood Cliffs, N.J.) was run constantly. Atomization of the liquid feed utilized a Büchi two-fluid nozzle with a 1.5 mm diameter. The two-fluid atomizing gas was set at 40 mm. Aspirator rate varied between 80% and 90% (32 and 35 $m^3$h). Room air was used as the drying gas. Inlet temperature of the process gas was 180° C. and outlet temperature at 85° C. with a liquid feedstock flow rate of 6 mL/min to 7 mL/min. The solids concentration was 4.2 g/L in ultrapure water.

Formulation II was produced using the same equipment and settings. Inlet temperature of the process gas was 180° C. and outlet temperature from 85° C. to 86° C. with a liquid feedstock flow rate of 6 mL/min to 7 mL/min. Aspirator rate was 90% (35 $m^3$h). The solids concentration was 5 g/L in ultrapure water.

Formulation III was produced using the same equipment and settings. Inlet temperature of the process gas was 180° C. and outlet temperature from 83° C. to 84° C. with a liquid feedstock flow rate of 6 mL/min to 7 mL/min. Aspirator rate was 90% (35 $m^3$h). The solids concentration was 5 g/L in ultrapure water.

Formulation IV was produced using the same equipment and settings. Inlet temperature of the process gas was 180° C. and outlet temperature from 83° C. to 84° C. with a liquid feedstock flow rate of 5 mL/min to 6 mL/min. Aspirator rate was 90% (35 $m^3$h). The solids concentration was 4 g/L in ultrapure water.

Formulation V was produced using the same equipment and settings. Inlet temperature of the process gas was 180° C. and outlet temperature from 76° C. to 77° C. with a liquid feedstock flow rate of 6 mL/min. Aspirator rate was 90% (35 $m^3$h). The solids concentration was 10 g/L in ultrapure water.

The powders produced were characterized with regard to density and dispersibility ratio. Bulk and tapped densities were determined using a SOTAX Tap Density Tester model TD1 (Horsham, PA.). For any given run, the entire sample was introduced to a tared 0.3 cc section of a disposable serological polystyrene micropipette (Grenier Bio-One, Monroe, N.C.) using a funnel made with weighing paper (VWR International, West Chester, Pa.) and the pipette section was plugged with polyethylene caps (Kimble Chase, Vineland, N.J.) to hold the powder. The powder mass and initial volume ($V_O$) were recorded and the pipette was attached to the anvil and run according to the USP I method. For the first pass, the pippette was tapped using Tap Count 1 (500 taps) and the resulting volume $V_a$ was recorded. For the second pass, Tap Count 2 was used (750 taps) resulting in the new volume $V_{b1}$. If $V_{b1} > 98\%$ of $V_a$, the test was complete, otherwise Tap Count 3 was used (1250 taps) iteratively until $V_{bn} > 98\%$ of $V_{bn-1}$. Bulk density was estimated prior to tap density measurement by dividing the weight of the powder by the volume of the powder, as estimated using the volumetric measuring device. Calculations were made to determine the powder bulk density ($d_B$), tap density ($d_T$), and Hausner Ratio (H), which is the tap density divided by the bulk density.

Volume median diameter was determined using a HELOS laser diffractometer and a RODOS dry powder disperser (Sympatec, Inc., Princeton, N.J.). A microspatula of material (approximately 5 milligrams) was introduced into the RODOS funnel, where a shear force is applied to a sample of particles as controlled by the regulator pressure of the incoming compressed dry air. The pressure settings were varied to use different amounts of energy to disperse the powder. The regulator pressure was set at 0.2 bar, 0.5 bar, 1.0 bar, 2.0 bar and 4.0 bar, with maximum orifice ring pressure at each pressure. The dispersed particles traveled through a laser beam where the resulting diffracted light pattern produced is collected, using an R1 or R3 lens, by a series of detectors. The ensemble diffraction pattern is then translated into a volume-based particle size distribution using the Fraunhofer diffraction model, on the basis that smaller particles diffract light at larger angles. 1/4 bar, 0.5/4 bar, 0.2/4 bar ratios were obtained by dividing average volume median diameter values obtained at each of 0.2 bar, 0.5 bar and 1.0 bar by the volume median diameter value obtained at 4.0 bar.

Results for the density tests for Formulations I, II, III, IV and V are shown in Table 3. The tap densities for all formulations are relatively high, especially for Formulation V. The bulk densities are such that the Hausner ratios are rather high for all formulations, particularly Formulation II and Formulation V. All five of the powders tested possess Hausner Ratios that are described in the art as being characteristic of powders with extremely poor flow properties (See, e.g., USP <1174>). USP <1174> notes that dry powders with a Hausner ratio greater than 1.35 are poor flowing powders. Flow properties and dispersibility are both negatively affected by particle agglomeration or aggregation. It is therefore unexpected that powders with Hasuner Ratios of 1.4 to 2.8 would be highly dispersible. This strengthens the counter-intuitiveness of these formulations being highly dispersible and possessing good aerosolization properties. In particular, Formulation V has a high tap density (0.78 g/cc) and a high Hausner ratio (2.79).

TABLE 3

Divalent cationic dry powder characteristics.

| Formulation | Density | | | HELOS/RODOS | | |
|---|---|---|---|---|---|---|
| | Bulk Density (g/cc) | Tap Density (g/cc) | Hausner Ratio | 1/4 bar | 0.5/4 bar | 0.2/4 bar |
| I MgSul: Albu | 0.34 ± 0.06 | 0.47 ± 0.03 | 1.38 | 1.00 | 1.09 | 1.10 |
| II CaSul: Malto: Cipro | 0.22 ± 0.02 | 0.46 ± 0.01 | 2.09 | 1.04 | 1.11 | 1.28 |
| III MgSul: Malto: Tobra | 0.34 ± 0.09 | 0.52 ± 0.02 | 1.53 | 1.05 | 1.10 | 1.20 |
| IV CaSul: Malto: Cipro | 0.30 ± 0.10 | 0.58 ± 0.03 | 1.93 | 1.09 | 1.17 | 1.29 |
| V MgLact: Leu | 0.28 ± 0.00 | 0.78 ± 0.02 | 2.79 | 1.00 | 1.00 | 1.06 |

Table 3 also shows that all five formulations have a HELOS/RODOS dispersibility ratio at 1/4 bar between 1.00 and 1.09, at 0.5/4 bar between 1.00 and 1.17, and at 0.2/4 bar between 1.06 and 1.29. Values that are close to 1.0, as these values are, are considered indicative that powders are highly dispersible. In particular, Formulations I and V displayed highly dispersible behavior with all dispersive pressure ratios less than 1.1. Specifically, Formulation I contained a very high load of drug (95 percent by weight) with a relatively small amount of divalent salt (5 weight percent of magnesium sulfate or 1 weight percent of magnesium ion).

Example 2

Dispersibility of Divalent Cationic Dry Powder

This example demonstrates the dispersibility of dry powder formulations when delivered from a dry powder inhaler over a range of inhalation flow rates and volumes.

The dispersibility of various powder formulations was investigated by measuring the geometric particle size distribution and the percentage of powder emitted from capsules when inhaling on a dry powder inhaler with flow rates representative of patient use. The particle size distribution and weight change of the filled capsules were measured for multiple powder formulations as a function of flow rate and inhaled volume in a passive dry powder inhaler.

Powder formulations were filled into size 3 HPMC capsules (V-Caps, Capsugel) by hand with the fill weight measured gravimetrically using an analytical balance (Mettler Toledo X5205). Fill weights of 20 mg were filled for Formulations I and V. A capsule-based passive dry powder inhaler (RS-01 Model 7, High Resistance, Plastiape S.p.A.) was used which had specific resistance of 0.036 $kPa^{1/2}LPM^{-1}$. Flow rate and inhaled volume were set using a timer controlled solenoid valve and flow control valve with an inline mass flow meter (TSI model 3063). Capsules were placed in the dry powder inhaler, punctured and the inhaler sealed inside a cylinder, exposing the air jet exiting from the DPI to the laser diffraction particle sizer (Spraytec, Malvern) in its open bench configuration. The steady air flow rate through the system was initiated using the solenoid valve and the particle size distribution was measured via the Spraytec at 1kHz for the duration of the single inhalation maneuver with a minimum of 2 seconds. Particle size distribution parameters calculated included the volume median diameter (Dv50) and the geometric standard deviation (GSD). At the completion of the inhalation duration, the dry powder inhaler was opened, the capsule removed and re-weighed to calculate the mass of powder that had been emitted from the capsule during the inhalation duration. Four inhalation conditions were used for each powder including 60 LPM and 2 L for the highest inhalation energy condition; 30 LPM and 1 L; 20 LPM and 1 L; and 15 LPM and 1 L for the lowest inhalation energy condition. At each testing condition, 5 replicate capsules were measured and the results of Dv50, GSD and capsule emitted powder mass (CEPM) were averaged.

In order to relate the dispersion of powders at different flow rates, volumes, and from inhalers of different resistances, the energy required to perform the inhalation maneuver was calculated Inhalation energy was calculated as $E=R^2Q^2V$ where E is the inhalation energy in Joules, R is the inhaler resistance in $kPa^{1/2}$/LPM, Q is the steady flow rate in L/min and V is the inhaled air volume in L. For the example described here, the inhalation energy for the case of 60 LPM and 2 L was 9.2 Joules while for the lowest case of 15 LPM and 1 L, the inhalation energy was 0.29 Joules.

Table 4 shows the dose emitted from a capsule (CEPM), and the particle size distribution parameters of the power emitted (Dv50 and GSD) for Formulations I and V at a capsule fill weight of 20 mg using the high resistance RS-01 dry powder inhaler. For Formulation V, the CEPM remained primarily unchanged as a function of decreased inhalation energy while the Dv50 increased only slightly from 2.33 to 3.24 micrometers, demonstrating excellent flow rate independence of both the amount of powder output and the size of the powder that exited the DPI. For Formulation I, while the CEPM decreased with decreasing inhalation energy, at least 25% of the filled dose is able to be emitted even down to the very low inhalation energies tested. The Dv50 increased with decreasing inhalation energy, but the Dv50 remained below 6 micrometers for all tested conditions.

TABLE 4

Dispersibility of divalent cationic dry powders.

|  | Flow Rate: (LPM) | 60 | 30 | 20 | 15 |
|---|---|---|---|---|---|
| Formulation I MgSul:Albu | Dv(50) (μm): | 1.48 ± 0.06 | 1.77 ± 0.06 | 2.35 ± 0.32 | 5.31 ± 2.62 |
|  | GSD (μm): | 3.71 ± 0.46 | 4.27 ± 1.07 | 5.19 ± 1.82 | 7.63 ± 1.00 |
|  | CEPM (%): | 73% | 44% | 25% | 33% |
| Formulation V MgLact:Leu | Dv(50) (μm): | 2.33 ± 0.17 | 2.14 ± 0.15 | 2.69 ± 0.15 | 3.24 ± 0.12 |
|  | GSD (μm): | 6.26 ± 0.40 | 4.28 ± 0.65 | 3.53 ± 0.57 | 2.55 ± 0.41 |
|  | CEPM (%): | 94% | 93% | 80% | 93% |

Example 3

Aerodynamic Particle Size

This example demonstrates that the aerodynamic size distribution of dry powder formulations comprised in part of divalent cationic salts, when delivered from a dry powder inhaler, is in a range appropriate for deposition in the respiratory tract.

Figure 1B:
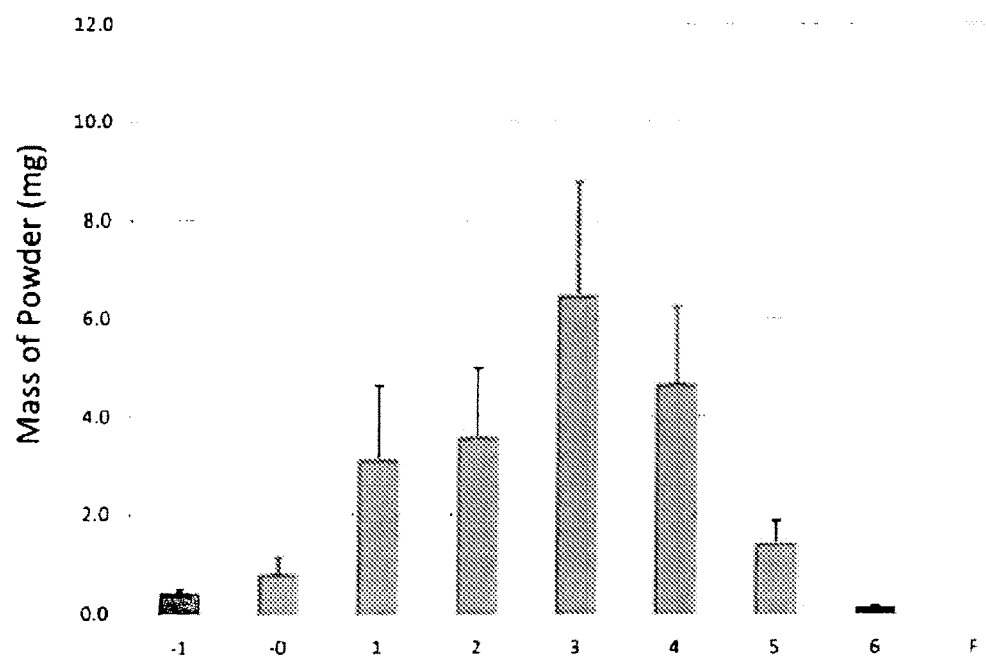
Figure 1C:
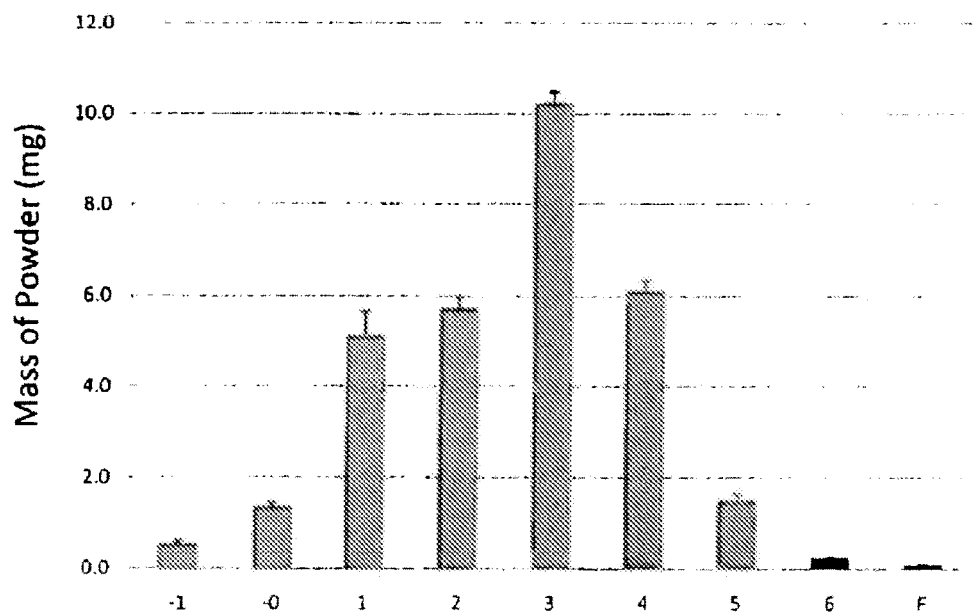
Figure 1D:
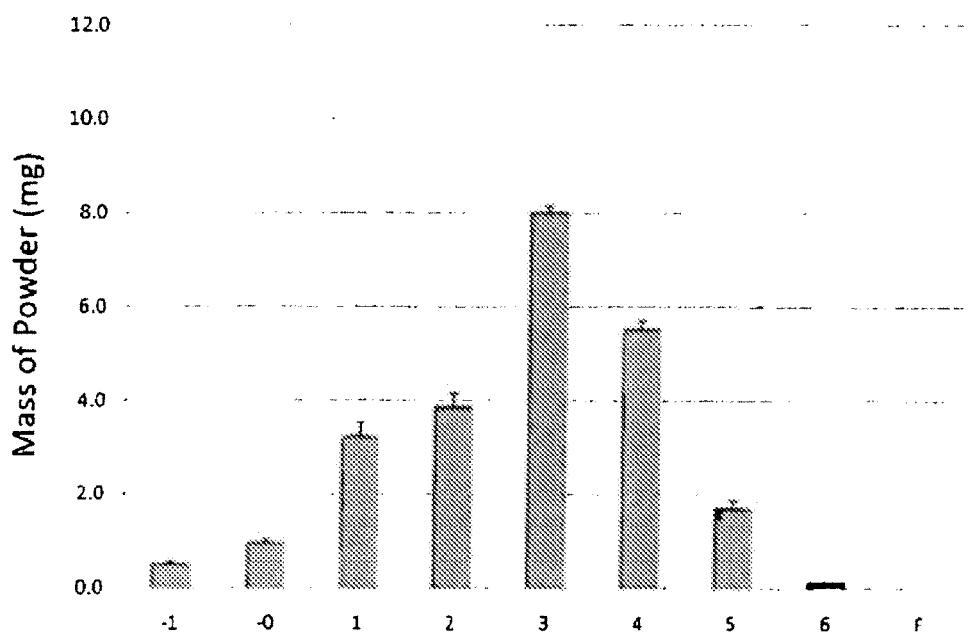
Figure 1E:
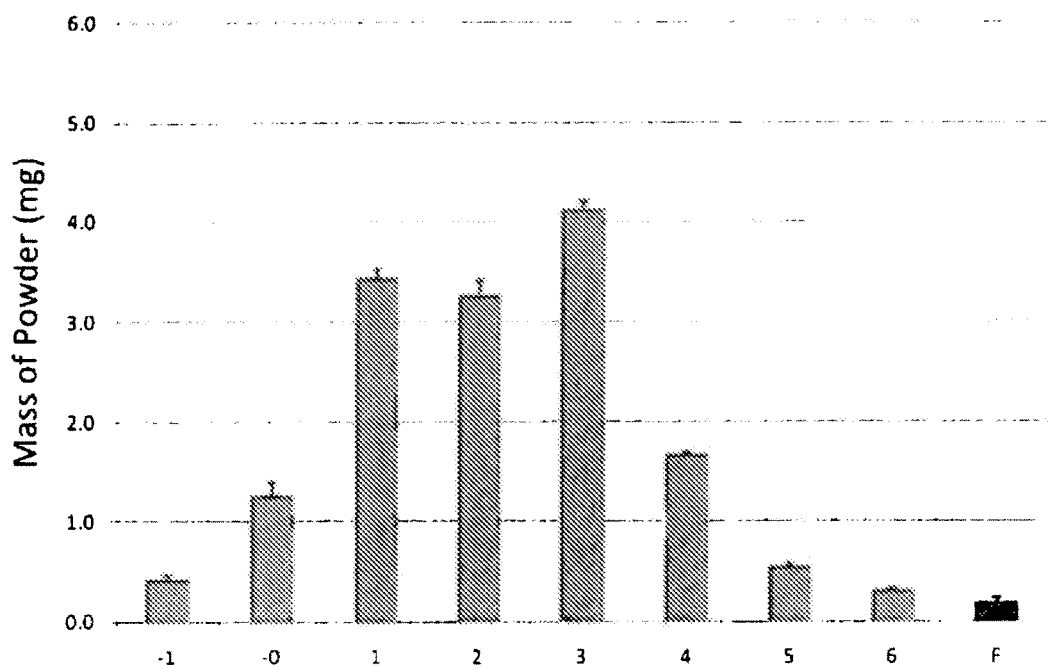
Figure 2:
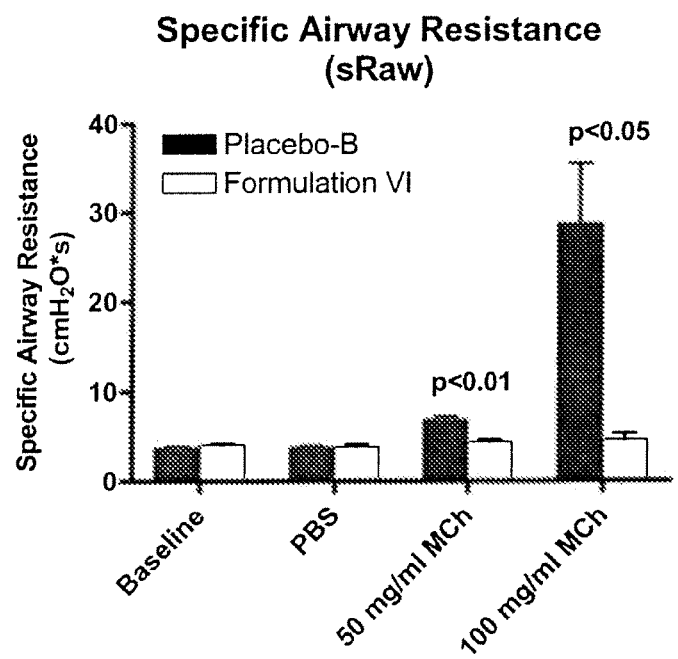
FIG. 2 is a graph illustrating the efficacy of a divalent cation-based dry powder formulation of tiotroprium bromide (TioB) in reducing airway hyperreactivity in an ovalbumin (OVA) mouse model of allergic asthma. The graph indicates that the spray dried drug (TioB) remained effective in treating airway hyperreactivity.

The aerodynamic particle size distributions of five powder formulations were measured by characterizing the powders with an eight stage Anderson cascade impactor (ACI). Powder formulations were filled into size 3 HPMC capsules (V-Caps, Capsugel) by hand with the fill weight measured gravimetrically using an analytical balance (Mettler Toledo XS205). Fill weights of 20 mg were filled for Formulations I and V, and fill weights of 50 mg were filled for Formulations II, III and IV. A reloadable, capsule-based passive dry powder inhaler (RS-01 Model 7, High Resistance, Plastiape, Osnago, Italy) was used to disperse the powder into the cascade impactor. One capsule was used for each measurement, with two actuations of 2 L of air at 60 LPM drawn through the dry powder inhaler (DPI). The flow rate and inhaled volume were set using a timer controlled solenoid valve with flow control valve (TPK2000, Copley Scientific). Three replicate ACI measurements were performed for each formulation. The impactor stage plates were inverted and pre-weighed 81 mm glass fiber filters (1820-6537, Whatman) were placed on them. After the inhalation maneuver, the impactor was disassembled and the glass fiber filters were weighed to determine the mass of powder deposited on each stage and on the final filter. The size distribution of the emitted powder was averaged across the replicates and the average mass of powder delivered to each of the stages (−1, −0, 1, 2, 3, 4, 5, 6, and F) are shown for each formulation in FIGS. 1A to 1E with error bars giving the standard deviation of the 3 replicates. The mass median aerodynamic diameter (MMAD), geometric standard deviation (GSD), and fine particle dose (FPD<4.4 μm) of the emitted powder were calculated and averaged across the replicates and the tabulation is shown in Table 5.

All five formulations were found to have repeatable size distributions as illustrated by the low standard deviations for all the stages and calculated values. All five formulations had respirable size distributions with all five formulations having MMADs of less than 5 micrometers. With a maximum GSD of 1.88 for the five formulations, the polydispersity of the size distributions was relatively small compared to typical dry powder formulations for inhalation. The fine particle dose shown in Table 5 for the five powder formulations demonstrated that a significant mass of the powder dose was contained in small diameter particles, listed here as less than 4.4 micrometers in diameter; dry particles of this size would be expected to deposit in the lung. Table 5 further demonstrates the delivery of fine particle doses of up to 24 mg of drug formulation from a single size 3 capsule.

TABLE 5

Aerodynamic particle size of divalent cationic dry powders.

| | aPSD (ACI-8) | | |
|---|---|---|---|
| Formulation Number | MMAD (μm) | GSD (μm) | FPD < 4.4 μm (mg) |
| I MgSul:Albu | 2.52 ± 0.16 | 1.83 ± 0.04 | 8.9 ± 2.1 |
| II CaSul:Malto:Cipro | 2.80 ± 0.10 | 1.88 ± 0.01 | 16.3 ± 5.7 |
| III MgSul:Malto:Tobra | 2.96 ± 0.07 | 1.84 ± 0.01 | 23.9 ± 0.7 |
| IV CaSul:Malto:Cipro | 2.75 ± 0.07 | 1.87 ± 0.01 | 19.3 ± 0.3 |
| V MgLact:Leu | 3.56 ± 0.02 | 1.82 ± 0.01 | 10.1 ± 0.2 |

Table 6 lists multiple calcium and magnesium salts. The table shows their chemical formula, the molecular weights (MW) of each salt, and the relative percentage of the divalent cation (e.g., $Ca^{2+}$, $Mg^{2+}$) in the salt. The divalent cation can comprise a large, relative percentage of the weight of the salt either because of the divalent cation's relative weight in comparison to the other components of the salt, e.g., calcium or magnesium chloride and/or the salt contains multiple of the divalent cation, e.g., calcium or magnesium citrate.

TABLE 6

Weight Percent of $Ca^{2+}$ in Salt Molecules

Weight % of Calcium ion in Salt Molecule

| Salt | Formula | MW (g/mol) | Weight % of $Ca^{2+}$ in molecule |
|---|---|---|---|
| Calcium carbonate | $CaCO_3$ | 100.09 | 40.0 |
| Calcium chloride | $CaCl_2$ | 110.98 | 36.0 |
| Calcium phosphate dibasic | $CaHPO_4$ | 136.06 | 29.4 |
| Calcium sulfate | $CaSO_4$ | 136.14 | 29.4 |
| Calcium acetate | $Ca(C_2H_3O_2)_2$ | 158.17 | 25.3 |
| Calcium citrate | $Ca_3(C_6H_5O_7)_2$ | 498.46 | 24.1 |
| Calcium lactate | $Ca(C_3H_5O_3)_2$ | 218.218 | 18.3 |
| Calcium sorbate | $CaC_{12}H_{14}O_4$ | 262.33 | 15.2 |
| Calcium gluconate | $CaC_{12}H_{22}O_{14}$ | 430.373 | 9.3 |
| Calcium stearate | $CaC_{36}H_{70}O_4$ | 607.02 | 6.6 |
| Calcium alginate | $[Ca(C_6H_7O_6)_2]_n$ | NA | NA |

TABLE 6-continued

Weight Percent of $Ca^{2+}$ in Salt Molecules

Weight % of Magnesium ion in Salt Molecule

| Salt | Formula | MW (g/mol) | Weight % of $Mg^{2+}$ in molecule |
|---|---|---|---|
| Magnesium carbonate | $MgCO_3$ | 84.31 | 28.8 |
| Magnesium carbonate hydroxide | $(MgCO_3)_4 \cdot Mg(OH)_2$ | 395.61 | 30.7 |
| Magnesium chloride | $MgCl_2$ | 95.21 | 25.5 |
| Magnesium citrate tribasic | $Mg_3(C_6H_5O_7)_2$ | 451.11 | 16.2 |
| Magnesium lactate | $Mg(C_3H_5O_3)_2$ | 202.45 | 12.0 |
| Magnesium sulfate | $MgSO_4$ | 120.37 | 20.2 |

Weight % of Monovalent ion in Salt Molecule

| Salt | Molecular Formula | MW (g/mol) | Weight % of cation in molecule |
|---|---|---|---|
| Potassium chloride | KCl | 74.55 | 52.4 |
| Potassium citrate | $C_6H_5K_3O_7$ | 306.39 | 38.3 |
| Sodium ascorbate | $C_6H_7NaO_6$ | 198.11 | 11.6 |
| Sodium bicarbonate | $CHNaO_3$ | 84.01 | 27.4 |
| Sodium carbonate | $CNa_2O_3$ | 105.99 | 43.4 |
| Sodium chloride | NaCl | 58.44 | 39.3 |
| Sodium citrate | $C_6H_5Na_3O_7$ | 258.07 | 26.7 |
| Sodium lactate | $C_3H_5NaO_3$ | 112.06 | 20.5 |
| Dibasic sodium phosphate | $HNa_2O_4P$ | 141.96 | 32.4 |
| Sodium propionate | $C_3H_5NaO_2$ | 96.06 | 23.9 |
| Sodium sulfate | $Na_2O_4S$ | 142.04 | 32.4 |

Example 4

Magnesium Salt-Containing Dry Powders, Optionally Combined with Active Pharmaceutical Agents A. Powder Preparation.

Feedstock solutions were prepared in order to manufacture dry powders comprised of dry particles containing a magnesium salt, a non-salt excipient, and optionally, at least one pharmaceutical active agent. Table 7 lists the components of the feedstock formulations used in preparation of the dry powders comprised of dry particles. Weight percentages are given on a dry basis.

TABLE 7

Feedstock compositions of magnesium-salt with excipient, and optionally, with a pharmaceutically active agents

| Formulation | Salt | % Salt load (w/w) | Excipient | % Excipient load (w/w) | Drug | % Drug load (w/w) |
|---|---|---|---|---|---|---|
| VI | Magnesium lactate | 9 | Maltodextrin | 90.9 | Tiotropium bromide (TioB) | .113 |
| VII | Magnesium lactate | 10 | Mannitol | 90 | N/A | N/A |
| VIII | Magnesium lactate | 10 | Maltodextrin | 90 | N/A | N/A |
| IX | Magnesium sulfate | 10 | Leucine | 90 | N/A | N/A |
| X | Magnesium lactate | 10 | Leucine | 90 | N/A | N/A |

N/A = not applicable

The feedstock solutions were made according to the parameters in Table 8.

TABLE 8

Formulation Conditions

| Formulation: | VI | VII | VIII | IX | X |
|---|---|---|---|---|---|
| Total solids (g) | 4 | 3 | 3 | 3 | 3 |
| Total volume water (L) | 0.4 | 0.3 | 0.3 | 0.3 | 0.3 |
| Total solids concentration (g/L) | 10 | 10 | 10 | 10 | 10 |
| Amount of magnesium lactate in 1 L (g) | 0.9 | 1.0 | 1.0 | 1.0 | 1.0 |
| Amount of magnesium sulfate in 1 L (g) | 0 | 0 | 0 | 0 | 0 |
| Amount of maltodextrin in 1 L (g) | 9.09 | 0 | 9.0 | 0 | 0 |
| Amount of mannitol in 1 L (g) | 0 | 9.0 | 0 | 0 | 0 |
| Amount of leucine in 1 L (g) | 0 | 0 | 0 | 9.0 | 9.0 |
| Amount TioB in 1 L (g) | 0.0113 | 0 | 0 | 0 | 0 |

For all formulations, the liquid feedstock was batch mixed

Formulation VI through X dry powders were produced by spray drying on the Büchi B-290 Mini Spray Dryer (BÜCHI Labortechnik AG, Flawil, Switzerland) with powder collection from a High Performance cyclone in a 60 mL glass vessel. The system used the Büchi B-296 dehumidifier and an external LG dehumidifier (model 49007903, LG Electronics, Englewood Cliffs, N.J.) was run constantly. Atomization of the liquid feed utilized a Büchi two-fluid nozzle with a 1.5 mm diameter. The two-fluid atomizing gas was set at 40 mm (667 LPH) and the aspirator rate to 80% (32 cubic meters per hour). Air was used as the drying gas and the atomization gas. Table 9 below includes details about the spray drying conditions.

TABLE 9

Spray Drying Process Conditions

| Process Parameters | Formulation | | | | |
|---|---|---|---|---|---|
| | VI | VII | VIII | IX | X |
| Liquid feedstock solids concentration (g/L) | 10 | 10 | 10 | 10 | 10 |
| Process gas inlet temperature (° C.) | 100 | 100 | 100 | 115 | 115 |
| Process gas outlet temperature (° C.) | 54-59 | 55-56 | 56-60 | 63-66 | 65 |

TABLE 9-continued

Spray Drying Process Conditions

| Process Parameters | Formulation | | | | |
|---|---|---|---|---|---|
| | VI | VII | VIII | IX | X |
| Process gas flowrate (liter/hr, LPH) | 667 | 667 | 667 | 667 | 667 |
| Atomization gas flowrate (meters$^3$/hr) | 32 | 32 | 32 | 32 | 32 |
| Liquid feedstock flowrate (mL/min) | 2.8 | 2.6 | 2.6 | 2.5 | 2.6 |

B. Powder Characterization.

Powder physical and aerosol properties are summarized in Tables 10 to 14 below. Values with ±indicate standard deviation of the value reported. Two-stage ACI-2 results are reported in Table 10 for $FPF_{TD}$<3.4 μm and $FPF_{TD}$<5.6 μm. Formulations VI, VIII, IX and X all had a $FPF_{TD}$<3.4 μm greater than 20%. Formulations VIII, IX and X had a $FPF_{TD}$<3.4 μm greater than 30%. Formulations VI, VIII, IX and X all had a $FPF_{TD}$<5.6 μm greater than 35%. Formulations VIII, IX and X had a $FPF_{TD}$<5.6 μm greater than 55%.

TABLE 10

Aerodynamic properties

| | ACI-2 | |
|---|---|---|
| Formulation | $FPF_{TD}$ < 3.4 μm % | $FPF_{TD}$ < 5.6 μm % |
| VI | 22.99% ± 0.12% | 37.99% ± 2.00% |
| VII | 14.05% ± 0.88% | 26.72% ± 1.32% |
| VIII | 33.67% ± 5.83% | 57.57% ± 5.31% |
| IX | 40.46% ± 3.54% | 69.63% ± 4.02% |
| X | 46.45% ± 0.99% | 71.99% ± 0.90% |

Density-related measurements are listed in Table 11. Formulations VI, VII and VIII had a tapped density greater than 0.60 g/cc. All formulations had a Hausner Ratio greater than 1.4. Formulations VII, VIII, IX and X had Hausner Ratios greater than 2.2.

TABLE 11

Density properties of the magnesium salts

| | Density | | |
|---|---|---|---|
| Formulation | Bulk g/cc | Tapped g/cc | Hausner Ratio |
| VI | 0.44 ± 0.04 | 0.64 ± 0.01 | 1.46 |
| VII | 0.32 ± 0.04 | 0.79 ± 0.09 | 2.47 |
| VIII | 0.30 ± 0.01 | 0.75 ± 0.11 | 2.52 |
| IX | 0.11 ± 0.00 | 0.35 ± 0.03 | 3.17 |
| X | 0.14 ± 0.04 | 0.33 ± 0.06 | 2.34 |

Table 12 shows that formulations VIII, IX and X had geometric diameters (Dv50) of less than 2.2 microns when emitted from a dry powder inhaler at a flowrate of 60 LPM. Formulations IX and X had a Dv50 just under 2.0 microns. Formulations VIII, IX and X had a Dv50 of less than 6.5 microns at 15 LPM. Formulation VIII had a Dv50 at 15 LPM of 2.47 microns.

TABLE 12

Geometric Diameters

| | Dispersibility - Spraytec | | | |
|---|---|---|---|---|
| | @ 60 LPM | | @ 15 LPM | |
| Formulation | Dv50 (μm) | GSD | Dv50 (μm) | GSD |
| VII | 6.83 ± 0.63 | 3.47 ± 0.11 | 17.32 ± 6.99 | 4.63 ± 0.50 |
| VIII | 2.17 ± 0.05 | 5.91 ± 0.16 | 2.47 ± 0.14 | 3.10 ± 0.64 |
| IX | 1.98 ± 0.06 | 3.62 ± 0.06 | 5.64 ± 0.36 | 3.04 ± 0.13 |
| X | 1.99 ± 0.09 | 3.66 ± 0.20 | 6.05 ± 0.15 | 3.05 ± 0.16 |

Table 13 shows that all formulations had a capsule emitted particle mass (CEPM) of greater than 97% at 60 LPM. All formulations had a CEPM of greater than 80% at 15 LPM. Formulations XXI, XXII, and XXIII each had a CEPM of greater than 92% at 15 LPM. Formulations XXII and XXIII each had a CEPM of greater than 97% at 15 LPM. Formulation VI was not tested for Dv50 or CEPM across varing inspiratory flow rate.

TABLE 13

Dispersitibilty properties

| | Dispersibility - CEPM | |
|---|---|---|
| Formulation | @ 60 LPM CEPM | @ 15 LPM CEPM |
| VII | 99.13% ± 0.29% | 87.79% ± 17.84% |
| VIII | 97.54% ± 0.56% | 94.33% ± 0.34% |
| IX | 100.24% ± 0.19% | 98.97% ± 0.32% |
| X | 99.22% ± 0.32% | 98.33% ± 0.24% |

Table 14 shows that all formulations had a Dv50 of about 3.0 microns or less using the RODOS at a 1.0 bar setting. Formulations VI, VIII, IX and X each had a Dv50 of less than 2.4 microns. Formulations IX and X each had a Dv50 of about 2.0 microns or less. All measured formulations had a RODOS Ratio for 0.5 bar/4 bar of less than 1.1. All measured formulations had a RODOS Ratio for 1 bar/4 bar of less than 1.05, with Formulation VII giving an odd result of less than 1.

TABLE 14

Dispersitibilty properties (Geometric diameter using RODOS)

| | RODOS | | | | | | | |
|---|---|---|---|---|---|---|---|---|
| | 0.5 bar | | 1.0 bar | | 4.0 bar | | | |
| Form. | Dv50 (μm) | GSD | Dv50 (μm) | GSD | Dv50 (μm) | GSD | 0.5/4 bar | 1/4 bar |
| VI | 2.16 | 2.09 | 2.13 | 2.09 | 2.08 | 2.11 | 1.04 | 1.02 |
| VII | 3.67 | 2.74 | 3.02 | 2.60 | 3.59 | 2.61 | 1.02 | 0.84 |
| VIII | 2.41 | 2.08 | 2.37 | 2.09 | 2.36 | 2.08 | 1.02 | 1.00 |
| IX | 2.09 | 1.85 | 1.97 | 1.81 | 1.91 | 1.80 | 1.09 | 1.03 |
| X | 1.85 | 1.64 | 1.79 | 1.67 | 1.74 | 1.65 | 1.06 | 1.03 |

Example 5

Effect of a Divalent Metal Cation-Based Dry Powder Formulation Containing Tiotropium Bromide on Airway Hyperreactivity in an Ovalbumin Mouse Model of Allergic Asthma A mouse model of allergic asthma was established using ovalbumin (OVA). Balb-c mice were sensitized to ovalbumin (OVA) over a period of two weeks and subsequently challenged via aerosol with OVA as indicated in Schematic 2 below. Sensitizations were performed by intraperotineal injection of OVA plus Alum. Challenges were performed by whole body exposure to nebulized 1% OVA solution for 20 minutes. As presented in Table 15 below, mice were treated with a dry powder comprised of 90.9% maltodextrin, 9% magnesium lactate, 0.113% tiotropium bromide (Formulation VI) or a placebo dry powder of 98% Leucine, 2% sodium chloride, w/w on a dry basis (Placebo-B). 1 hour before pulmonary function testingon day 30. Treatments were made in a whole body exposure chamber using a capsule based dry powder inhaler system. It was known from the literature that tiotropium bromide (TioB) enhances pulmonary function, resulting in lower sRaw values, for animals and human beings challenged with methacholine chloride (MCh) in 0.9% sodium chloride for inhalation. Data depict the mean±SEM of 5 mice per group. Data were analyzed by Student's t-test, and asterics presented in FIGS. 3A and 3B represent a p-value of p<0.05. (Ohta, S. et al. (2010), "Effect of tiotropium bromide on airway inflammation and remodeling in a mouse model of asthma", Clinical and Experimental Allergy 40:1266-1275).

Schematic 2. OVA process of sensitization, challenge, treatment and testing.

TABLE 15

Divalent metal cation salt-based tiotropium dry powder formulation

| Formulation | Salt | % Salt load (w/w) | Excipient | % Excipient load (w/w) | Drug | % Drug load (w/w) |
|---|---|---|---|---|---|---|
| Placebo-B | Sodium chloride | 2 | Leucine | 98 | N/A | N/A |
| VI | Magnesium lactate | 9 | Maltodextrin | 90.9 | Tiotropium bromide (TioB) | .113 |

While the effects of TioB on sRaw were known from the literature, the effect of co-formulating the TioB formulation with a magnesium salt was unknown. The effect of Formulation VI was tested, and compared to Placebo-B. Results from pulmonary function testing are shown in FIG XYZ. These data show that Formulation VI significantly reduced sRaw during MCh challenge compared to Placebo-B (p<0.00001).

The content of each of the patents, patent applications, patent publications and published articles cited in this specification are herein incorporated by reference in their entirety.

What is claimed is:

1. A respirable dry powder comprising respirable dry particles that comprise
   a) magnesium lactate; wherein the magnesium lactate provides magnesium ion in an amount between about 0.1% and 2.9% by weight of the dry particle,
   b) a pharmaceutical agent, and
   c) a pharmaceutically acceptable excipient,
   wherein the respirable dry powder does not contain a phospholipid, and wherein the respirable dry particles have a volume median geometric diameter (VMGD) of 5 microns or less when measured at a dispersion pressure of 1 bar and a dispersibility ratio (1 bar/4 bar) of less than about 1.5 as measured by laser diffraction (RODOS/HELOS system), and wherein the respirable dry particles have a tap density of greater than 0.4 g/cc.

2. The respirable dry powder of claim 1, wherein the respirable dry particles have a tap density of about 0.45 g/cc or greater.

3. The respirable dry powder of claim 1, wherein the respirable dry powder has a Fine Particle Fraction (FPF) of less than 5.6 microns of at least 45%.

4. The respirable dry powder of claim 1, wherein the respirable dry powder has a mass median aerodynamic diameter (MMAD) of about 5 microns or less.

5. The respirable dry powder of claim 1, wherein the excipient is present in an amount of about ≤20% by weight and comprises leucine.

6. The respirable dry powder of claim 1, wherein the excipient is present in an amount of about ≤20% by weight and comprises maltodextrin or mannitol.

7. The respirable dry powder of claim 1, wherein the pharmaceutically active agent is an antibiotic, a long-acting beta2 agonist (LABA), long-acting muscarinic antagonist (LAMA), a corticosteroid, or any combination thereof.

8. The respirable dry powder of claim 1, wherein the pharmaceutically active agent is a macromolecule.

9. The respirable dry powder of claim 1, wherein the pharmaceutically active agent is an antibody.

10. The respirable dry powder of claim 1, wherein the therapeutic agent is an antibiotic.

11. The respirable dry powder of claim 10, wherein the antibiotic is levofloxacin.

12. The respirable dry powder of claim 1, wherein the therapeutic agent is a muscarinic antagonist and beta-2 agonist (MABA).

13. The respirable dry powder of claim 1, wherein the respirable dry particles are further characterized by a capsule emitted powder mass (CEPM) of at least 80% when emitted from a passive dry powder inhaler that has a resistance of about 0.036 sqrt(kPa)/liters per minute (LPM) under the following conditions: an inhalation flowrate of 30 LPM, an inhalation volume of 1 liter using a size 3 capsule that contains a total mass of 20 mg, said total mass consisting of the respirable dry particles.

14. The respirable dry powder of claim 1, wherein the respirable dry particles are further characterized by a geometric size (Dv50) of below 6 micrometers when emitted from a passive dry powder inhaler that has a resistance of about 0.036 sqrt(kPa)/liters per minute (LPM) under the following conditions: an inhalation flowrate of 30 LPM, an inhalation volume of 1 liter using a size 3 capsule that contains a total mass of 20 mg, said total mass consisting of the respirable dry particles.

15. A method for treating a respiratory disease comprising administering to the respiratory tract of a patient in need thereof an effective amount of a respirable dry powder of claim 1, wherein the respiratory disease is asthma, airway hyperresponsiveness, seasonal allergic allergy, bronchiectasis, chronic bronchitis, emphysema, chronic obstructive pulmonary disease, or cystic fibrosis.

16. A method for treating an acute exacerbation of a respiratory disease comprising administering to the respiratory tract of a patient in need thereof an effective amount of a respirable dry powder of claim 1, wherein the respiratory disease is asthma, airway hyperresponsiveness, seasonal allergic allergy, bronchiectasis, chronic bronchitis, emphysema, chronic obstructive pulmonary disease, or cystic fibrosis.

17. A method for treating an infectious disease of the respiratory tract comprising administering to the respiratory tract of a patient in need thereof an effective amount of a respirable dry powder of claim 1.

18. A respirable dry powder comprising respirable dry particles that comprise
a) a calcium salt; wherein the calcium salt provides divalent metal cation in an amount between about 0.1% and 2.9% by weight of the dry particle, and
b) a pharmaceutical agent,
wherein the respirable dry powder does not contain phospholipid, and wherein the respirable dry particles have a volume median geometric diameter (VMGD) of 5 microns or less when measured at a dispersion pressure of 1 bar and a dispersibility ratio (1 bar/4 bar) of less than about 1.5 as measured by laser diffraction (RODOS/HELOS system), and wherein the respirable dry particles have a tap density of greater than 4 g/cc.

19. The respirable dry powder of claim 18, wherein the calcium salt is calcium lactate.

* * * * *